(12) United States Patent
Woge et al.

(10) Patent No.: US 11,969,364 B2
(45) Date of Patent: Apr. 30, 2024

(54) DEVICE FOR MOVING AN ARM AND A METHOD OF OPERATING THE DEVICE

(71) Applicant: TENDO AB, Lund (SE)

(72) Inventors: Sofie Woge, Lund (SE); Robin Gustafsson, Lund (SE); Pontus Renmarker, Malmö (SE); Sarawut Nielsen, Fredericia (DK)

(73) Assignee: Tendo AB, Lund (SE)

( * ) Notice: Subject to any disclaimer, the term of this patent is extended or adjusted under 35 U.S.C. 154(b) by 420 days.

(21) Appl. No.: 16/621,672

(22) PCT Filed: Jun. 19, 2018

(86) PCT No.: PCT/SE2018/050656
§ 371 (c)(1),
(2) Date: Dec. 11, 2019

(87) PCT Pub. No.: WO2018/236279
PCT Pub. Date: Dec. 27, 2018

(65) Prior Publication Data
US 2020/0121478 A1    Apr. 23, 2020

(30) Foreign Application Priority Data
Jun. 19, 2017    (SE) .................... 1750781-5

(51) Int. Cl.
*A61F 2/70*    (2006.01)
*A61F 2/68*    (2006.01)
(Continued)

(52) U.S. Cl.
CPC ............... *A61F 2/70* (2013.01); *A61F 5/013* (2013.01); *A61H 1/0285* (2013.01);
(Continued)

(58) Field of Classification Search
CPC ....................................... A61F 5/013
See application file for complete search history.

(56) References Cited

U.S. PATENT DOCUMENTS

| 4,644,938 A | 2/1987 | Yates et al. |
| 4,843,921 A | 7/1989 | Kremer |

(Continued)

FOREIGN PATENT DOCUMENTS

| JP | 2008-212652 | 9/2008 |
| JP | 2009-022577 | 2/2009 |

(Continued)

OTHER PUBLICATIONS

International Search Report for International App. No. PCT/SE2018/050656, dated Sep. 19, 2018, in 3 pages.
(Continued)

*Primary Examiner* — Jacqueline Wozznicki
(74) *Attorney, Agent, or Firm* — Knobbe, Martens, Olson & Bear LLP

(57) ABSTRACT

The invention relates to a device (10) for pivoting an arm (2) relative a joint (1). The device comprises at least one artificial tendon (20, 21) attached to a distal end (3) of the arm and a driving mechanism (30), the driving mechanism being connected to and adapted to pull the tendon and the distal end of the arm, and a method of operating the device.

19 Claims, 41 Drawing Sheets

(51) Int. Cl.
  *A61F 5/01*  (2006.01)
  *A61H 1/02*  (2006.01)
  *B25J 9/00*  (2006.01)
  *B25J 9/10*  (2006.01)
  *B25J 9/16*  (2006.01)
  *B25J 13/08* (2006.01)

(52) U.S. Cl.
  CPC ........... *B25J 9/0006* (2013.01); *B25J 9/1045* (2013.01); *B25J 9/1633* (2013.01); *B25J 13/085* (2013.01); *A61F 2002/6854* (2013.01); *A61F 2210/0057* (2013.01); *A61H 2201/1207* (2013.01)

(56) References Cited

U.S. PATENT DOCUMENTS

| | | | | |
|---|---|---|---|---|
| 5,167,612 | A * | 12/1992 | Bonutti | A61F 5/0123 602/5 |
| 5,184,319 | A | 2/1993 | Kramer | |
| 5,213,094 | A * | 5/1993 | Bonutti | A61F 5/0123 601/33 |
| 5,335,649 | A * | 8/1994 | Randall | A61H 1/02 601/24 |
| 7,873,477 | B1 * | 1/2011 | Gustafsson | G16B 35/00 702/19 |
| 10,231,859 | B1 * | 3/2019 | Thorne | A61H 1/024 |
| 2003/0223844 | A1 * | 12/2003 | Schiele | A63B 23/12 414/5 |
| 2005/0070834 | A1 * | 3/2005 | Herr | A61F 2/70 602/28 |
| 2008/0009771 | A1 * | 1/2008 | Perry | A61H 1/0281 600/587 |
| 2008/0288088 | A1 | 11/2008 | Langenfeld et al. | |
| 2009/0240184 | A1 * | 9/2009 | Tadman | A61F 5/013 602/22 |
| 2010/0041521 | A1 | 2/2010 | Ingvast et al. | |
| 2011/0214524 | A1 * | 9/2011 | Jacobsen | A61H 1/0266 901/21 |
| 2012/0029399 | A1 * | 2/2012 | Sankai | A61H 1/0288 601/40 |
| 2014/0100492 | A1 * | 4/2014 | Nagasaka | A61H 3/061 601/34 |
| 2014/0260950 | A1 * | 9/2014 | Cook | A61H 3/00 91/418 |
| 2014/0315695 | A1 * | 10/2014 | Scott | A63B 21/00178 482/91 |
| 2014/0342822 | A1 * | 11/2014 | Nordenstam | A63F 13/812 463/30 |
| 2015/0297367 | A1 * | 10/2015 | Baba | A61F 2/70 623/64 |
| 2017/0042704 | A1 | 2/2017 | Ryu et al. | |
| 2017/0049583 | A1 * | 2/2017 | Belter | A61F 2/5044 |
| 2017/0319421 | A1 * | 11/2017 | Julin | B25J 9/104 |
| 2018/0085277 | A1 * | 3/2018 | Julin | A61H 1/0262 |
| 2018/0238439 | A1 * | 8/2018 | Aulin | F16H 3/54 |
| 2019/0193551 | A1 * | 6/2019 | Aulin | B60K 6/405 |
| 2019/0202051 | A1 * | 7/2019 | Baldoni | F16H 7/06 |
| 2019/0343707 | A1 * | 11/2019 | Riener | A61H 3/00 |
| 2020/0121478 | A1 * | 4/2020 | Woge | B25J 9/1633 |
| 2021/0030575 | A1 * | 2/2021 | Bichler | A61F 5/013 |
| 2021/0282956 | A1 * | 9/2021 | Di Pardo | A61B 5/6812 |
| 2022/0023133 | A1 * | 1/2022 | Woge | A61H 1/0285 |
| 2022/0160521 | A1 * | 5/2022 | Benning | A61F 2/70 |

FOREIGN PATENT DOCUMENTS

| | | |
|---|---|---|
| JP | 2010-082342 A | 4/2010 |
| JP | 2010-240285 | 10/2010 |
| WO | WO2016/012480 | 1/2016 |
| WO | WO 2016/012480 | 1/2016 |
| WO | WO 2017/026943 | 2/2017 |
| WO | WO 2017/026943 A1 | 2/2017 |

OTHER PUBLICATIONS

International Preliminary Report on Patentability for International App. No. PCT/SE2018/050656, dated May 29, 2019, in 19 pages.
International Search Report for International App. No. PCT/SE2018/050656, dated Sep. 28, 2018, in 17 pages.
Notice from Swedish Patent and Registration Office for Swedish Patent App. No. 1750781-5, dated Jan. 30, 2019, in 4 pages.
Decision to Grant in Japanese Patent Application No. 2019-571223 dated Dec. 6, 2022, in 3 pages.

* cited by examiner

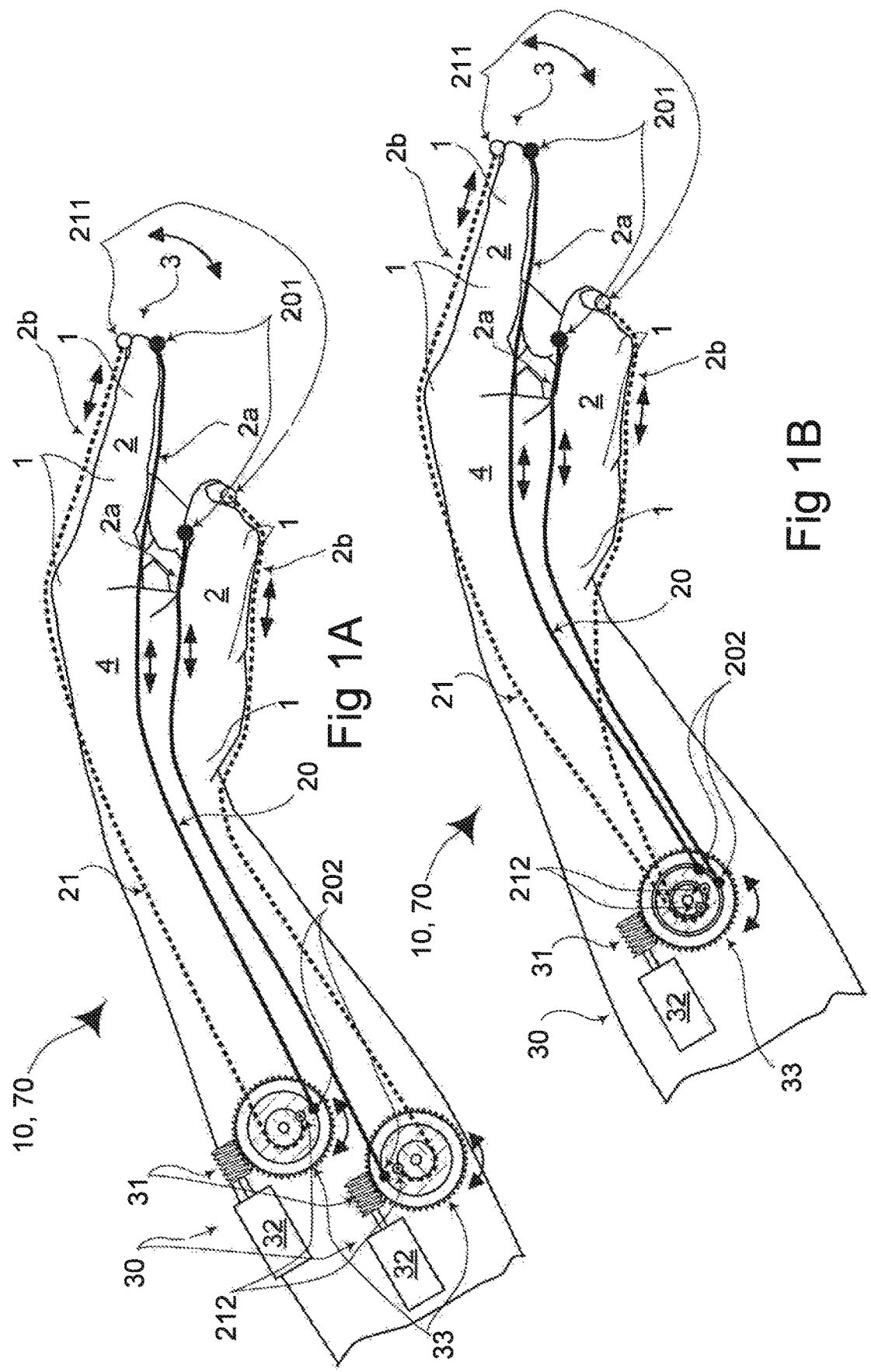

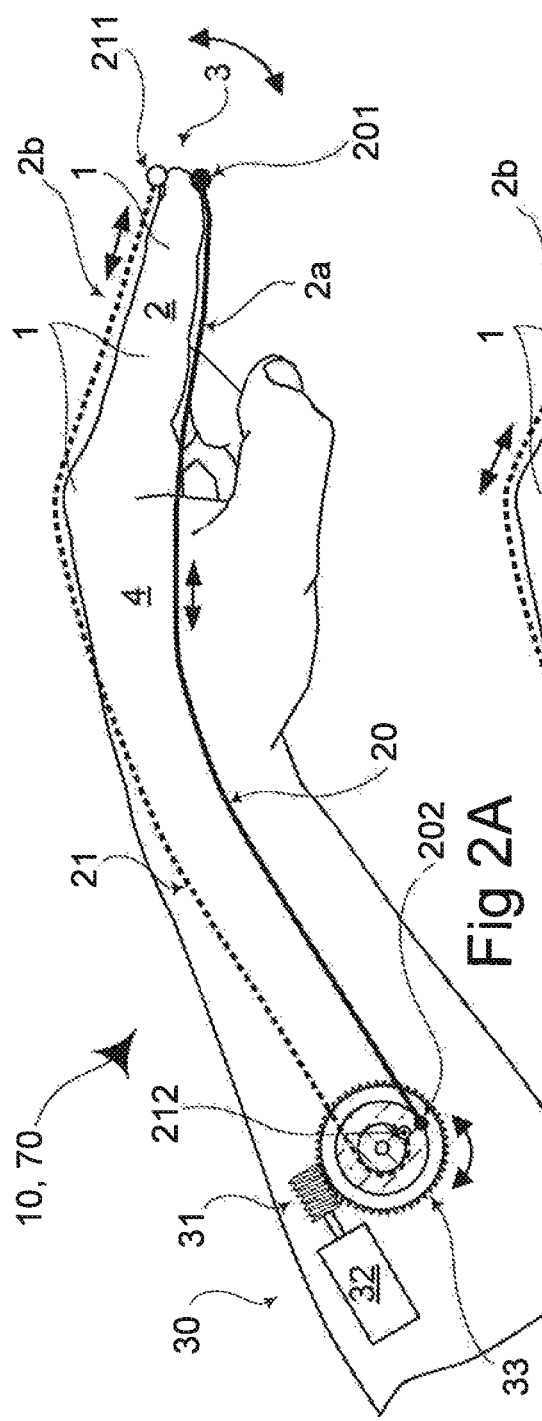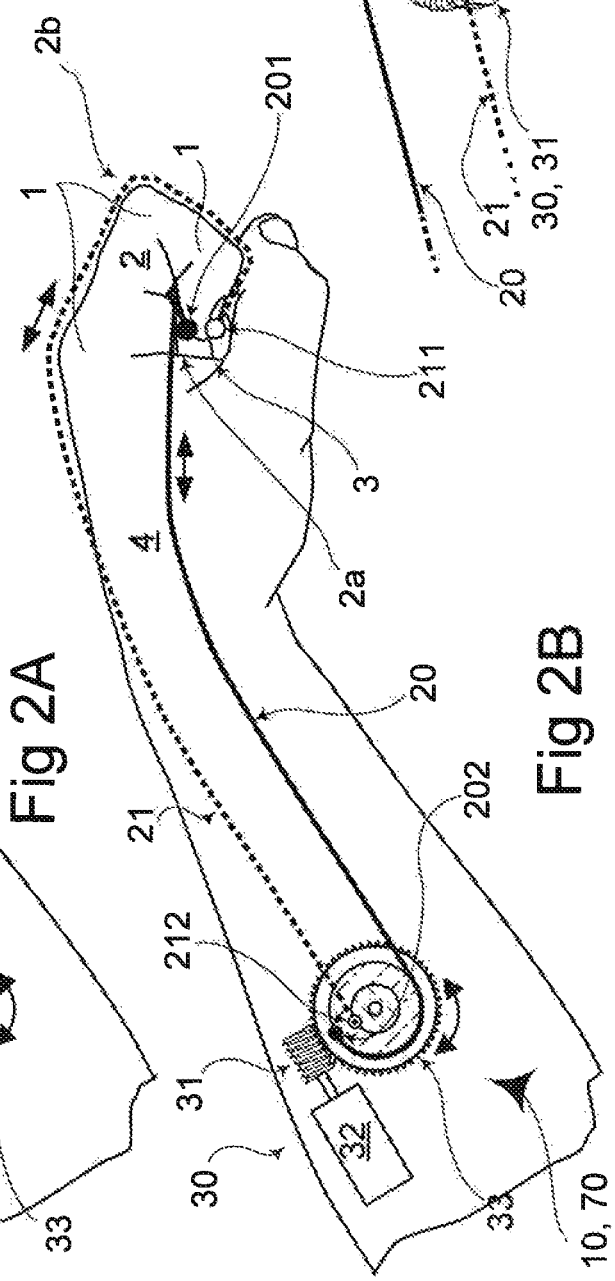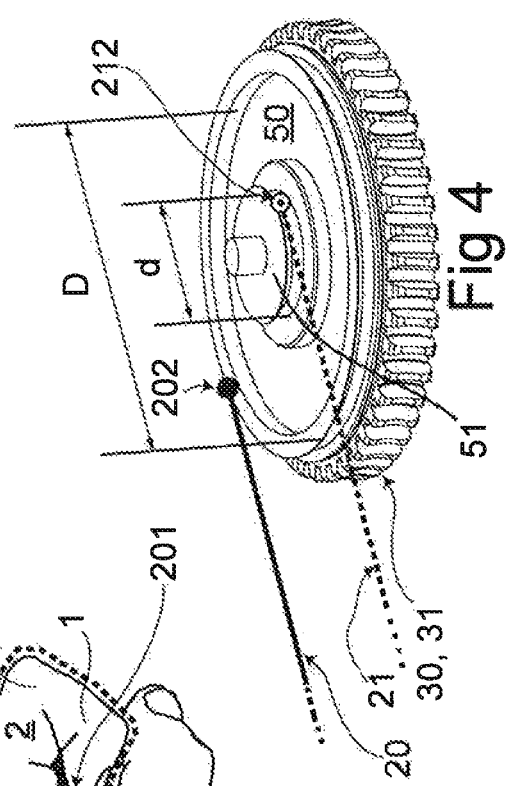

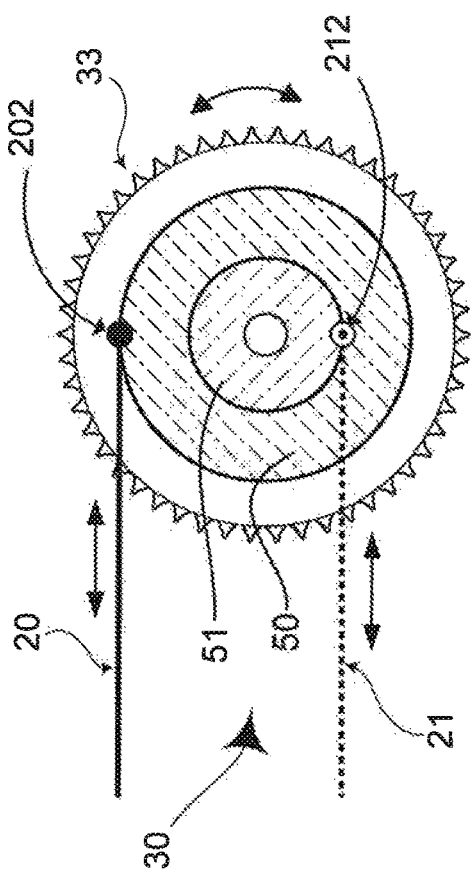
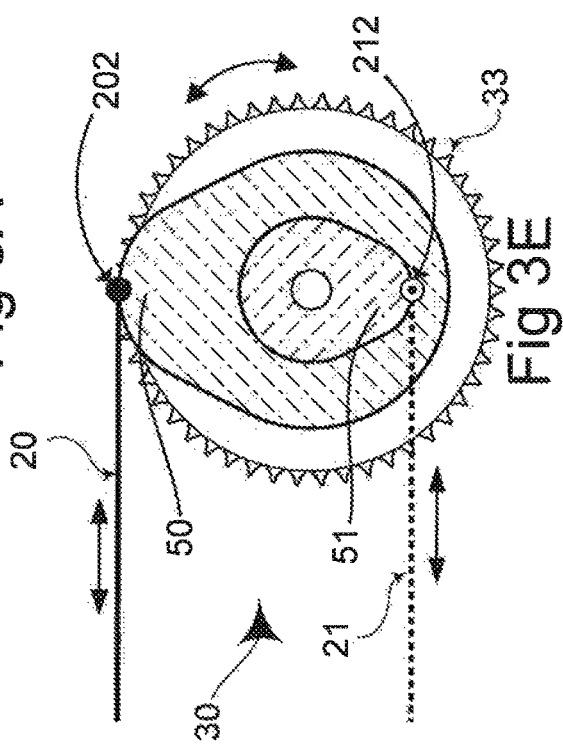
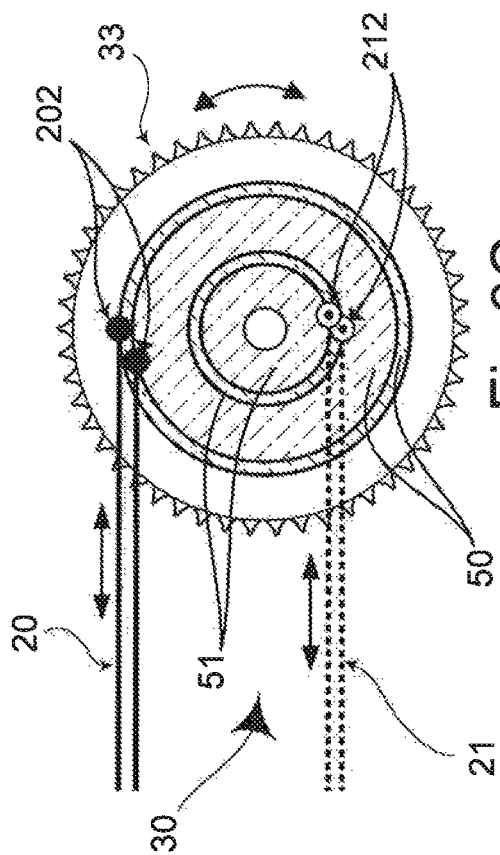
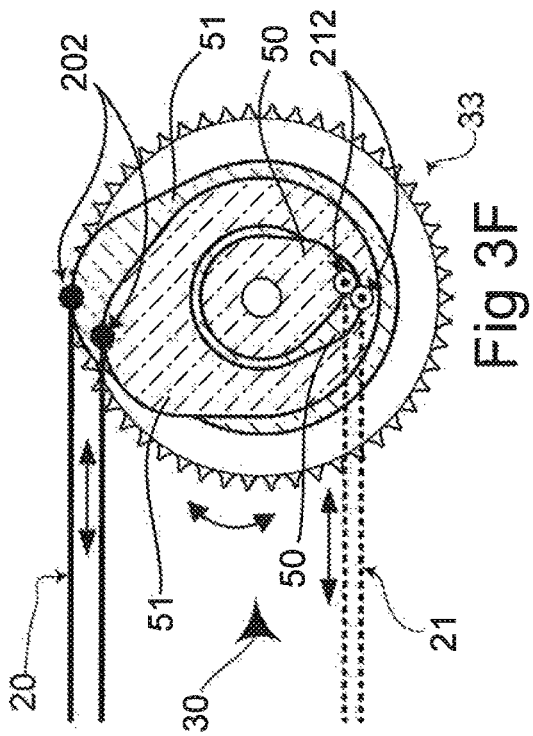

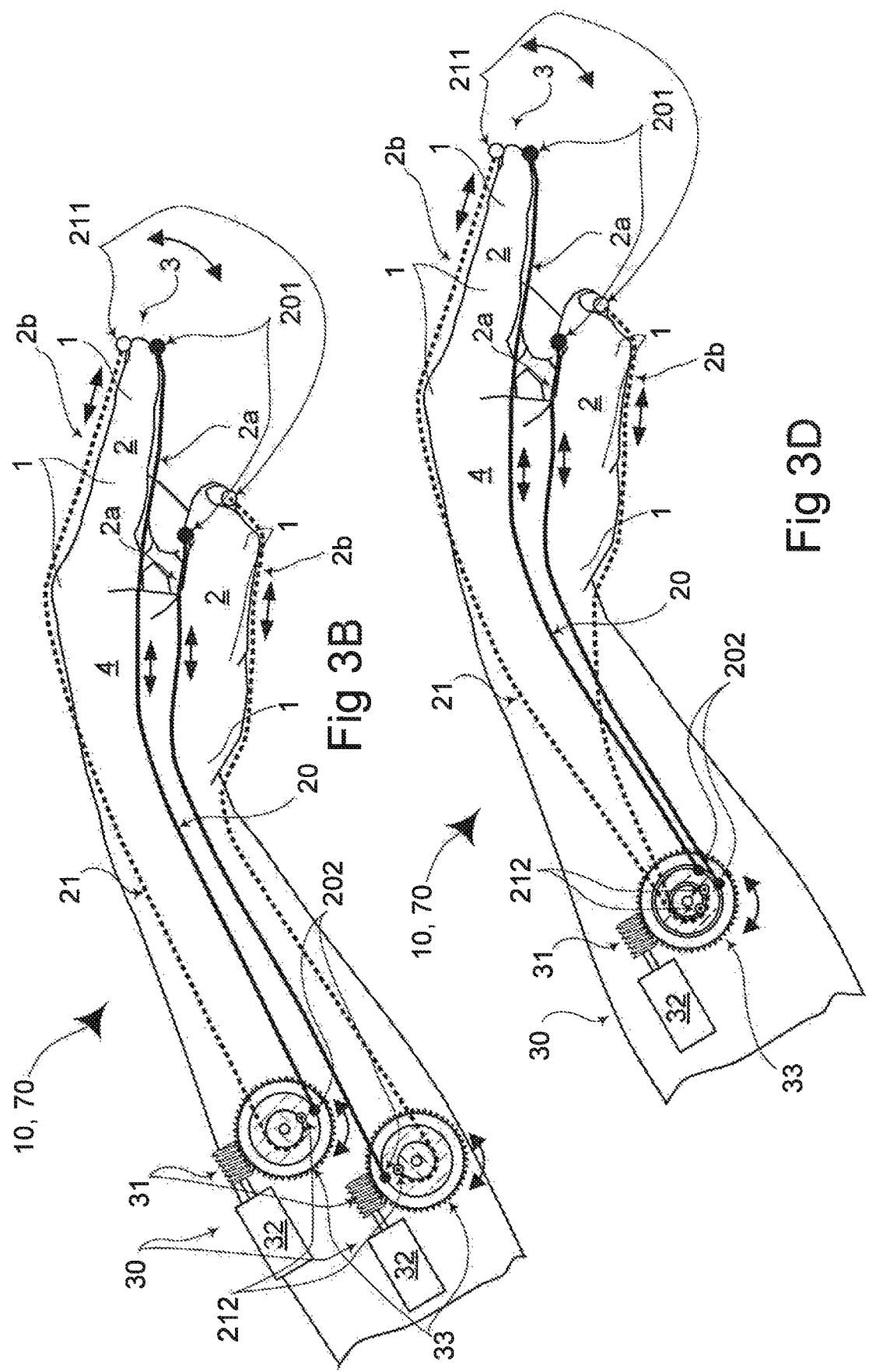

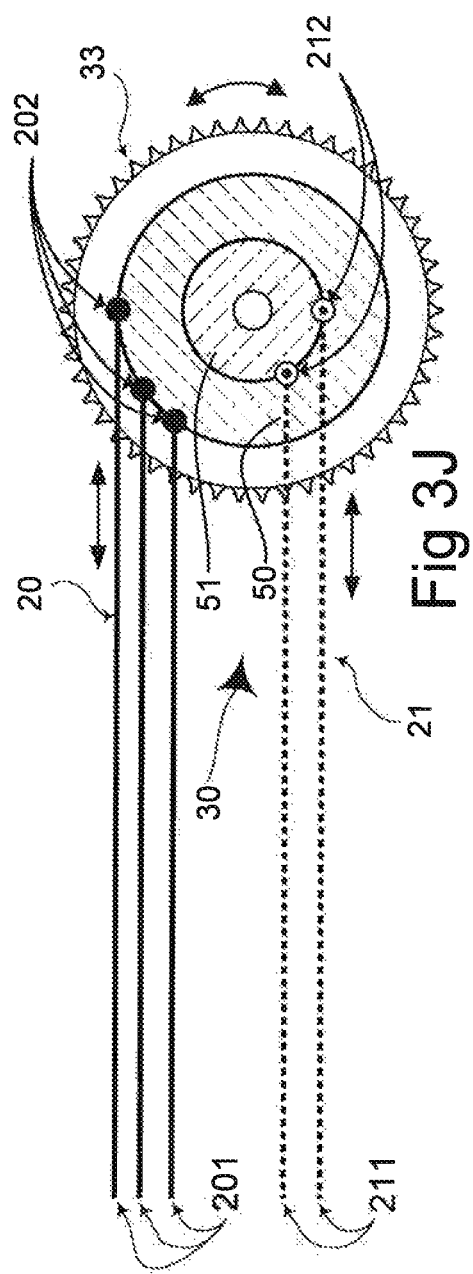
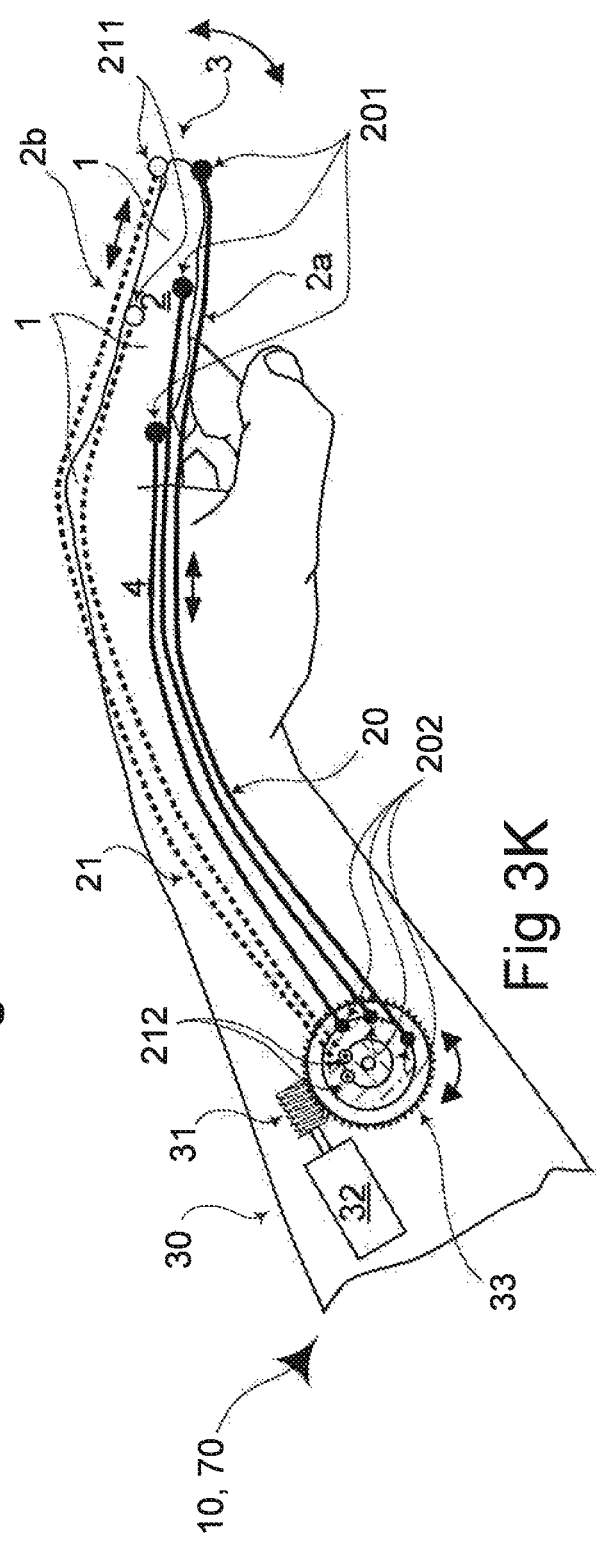

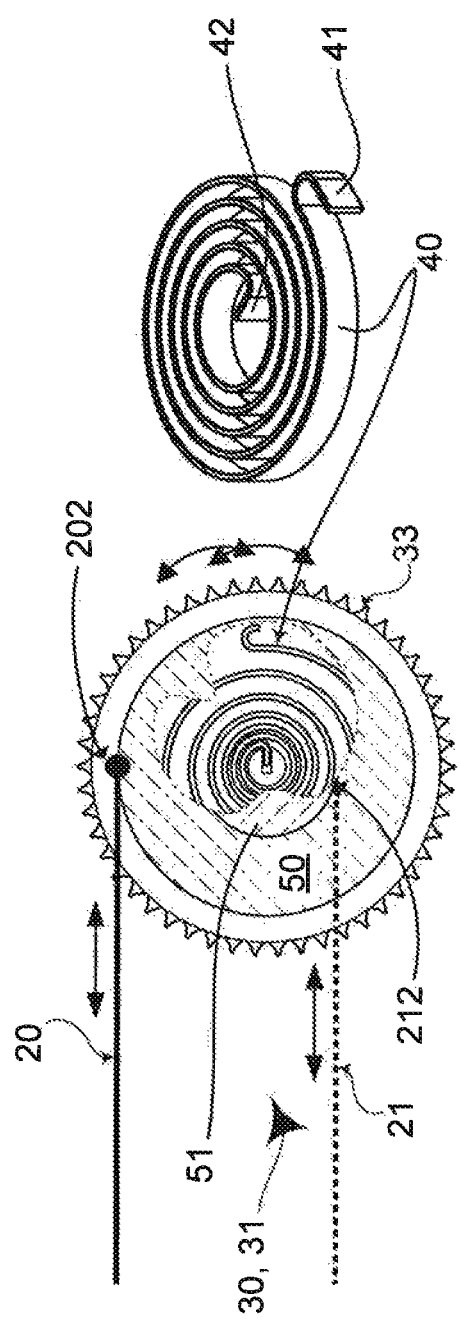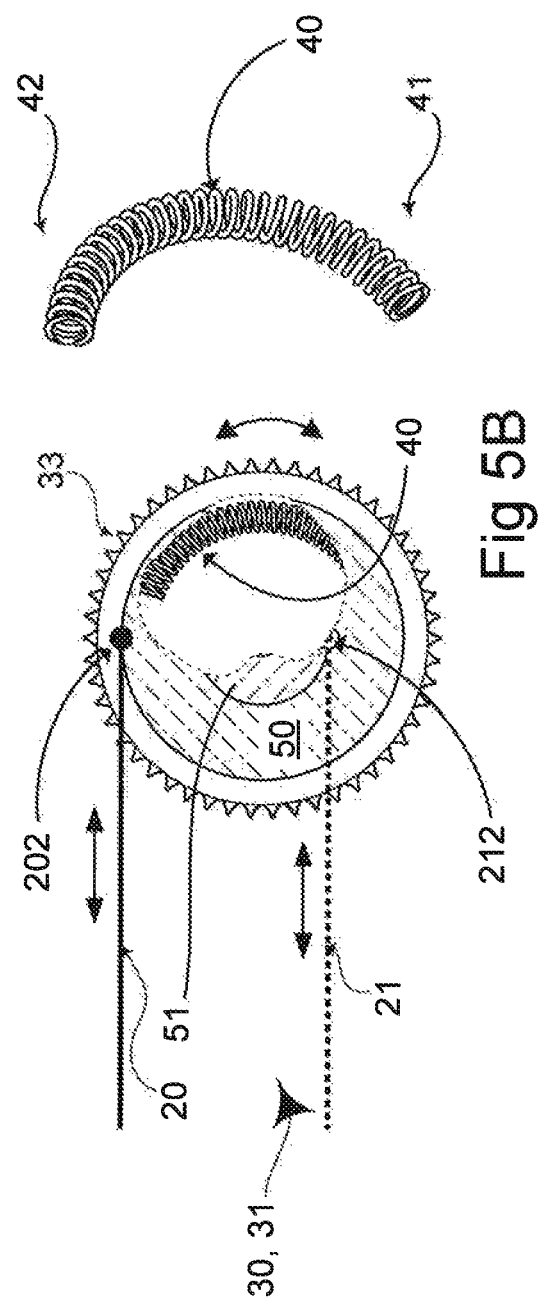

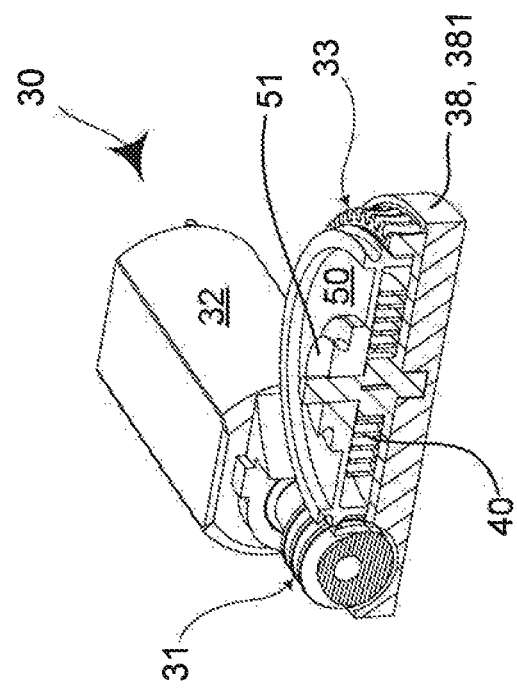
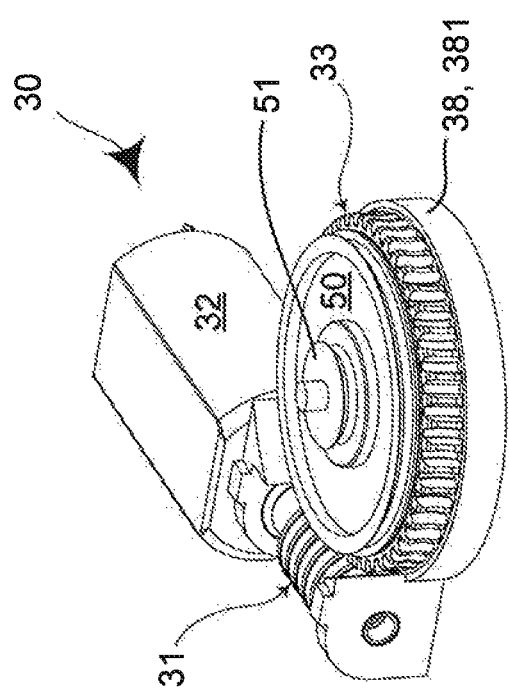
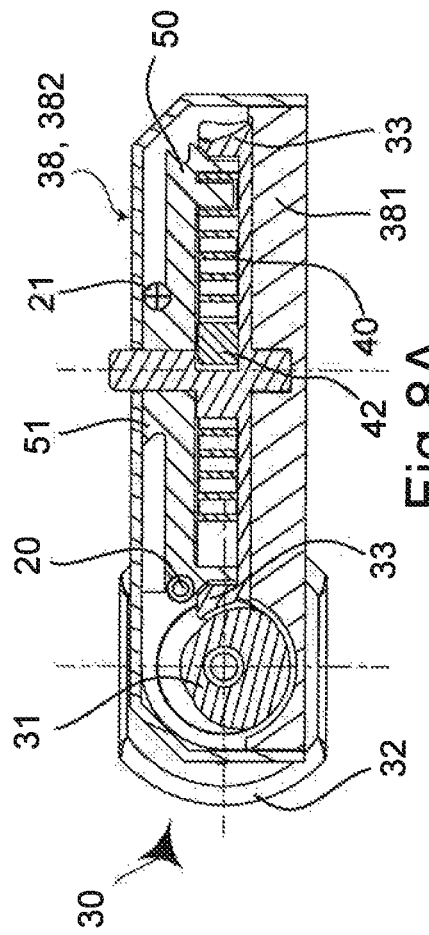
Fig 6A
Fig 6B
Fig 8A

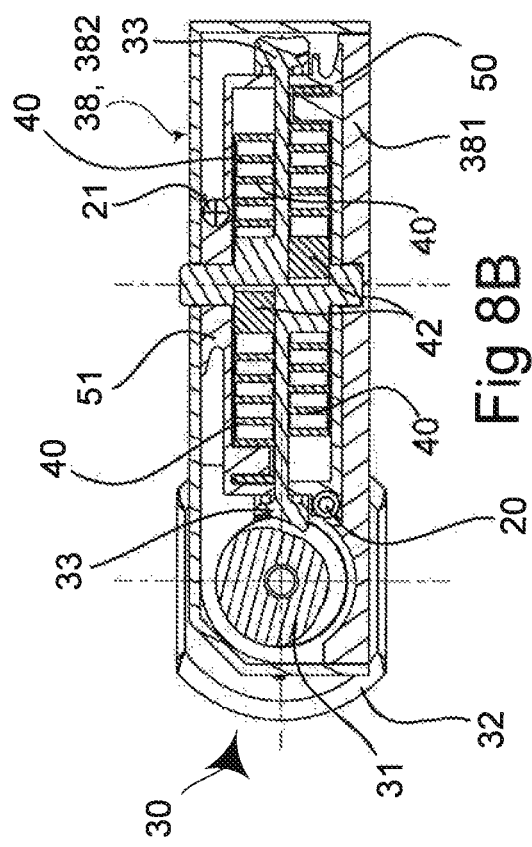
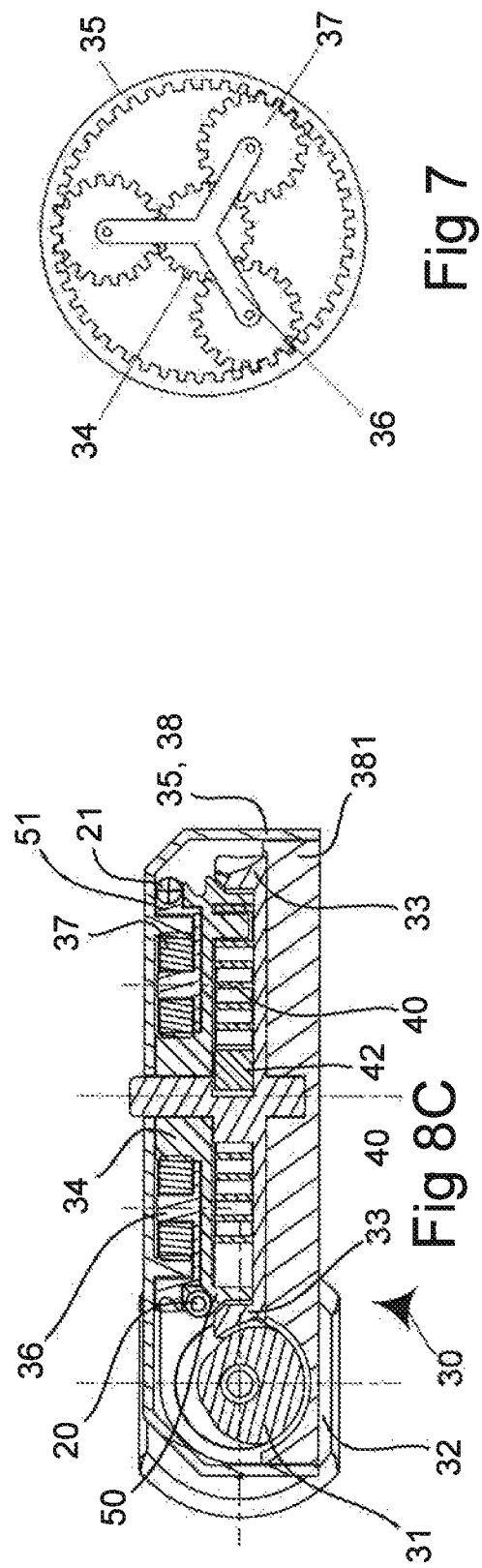

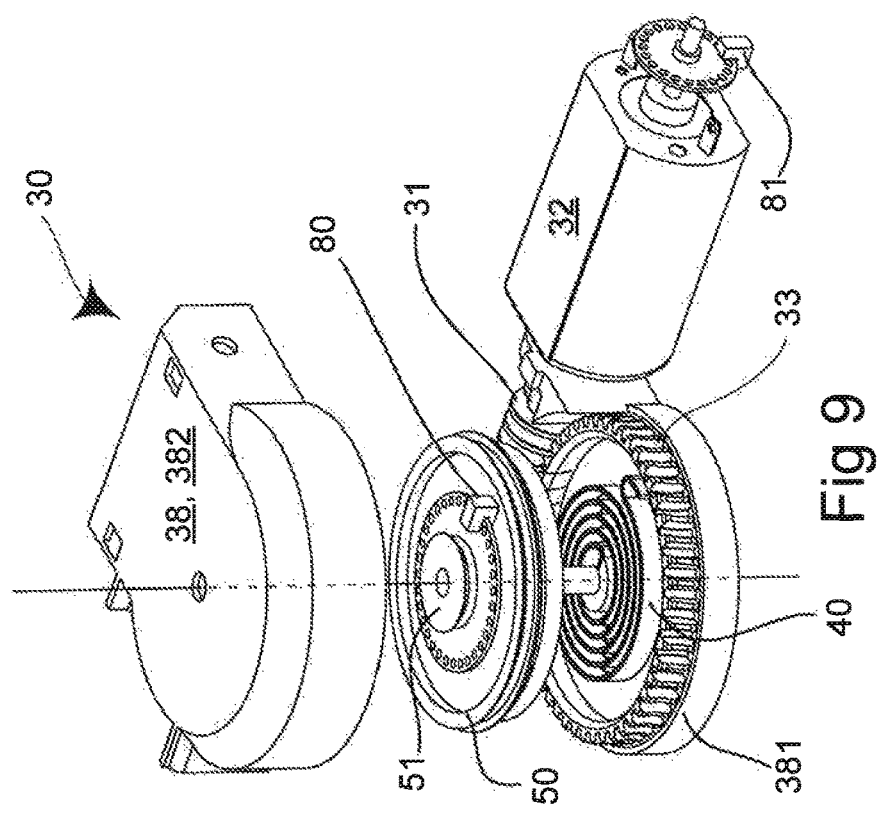
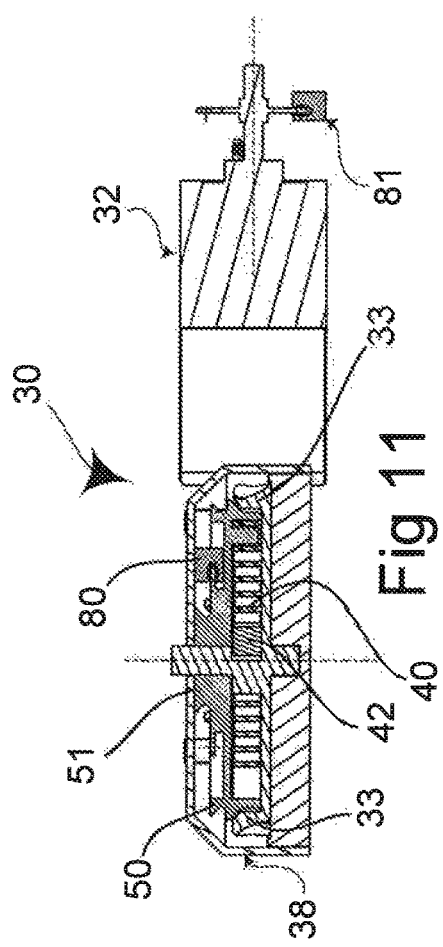
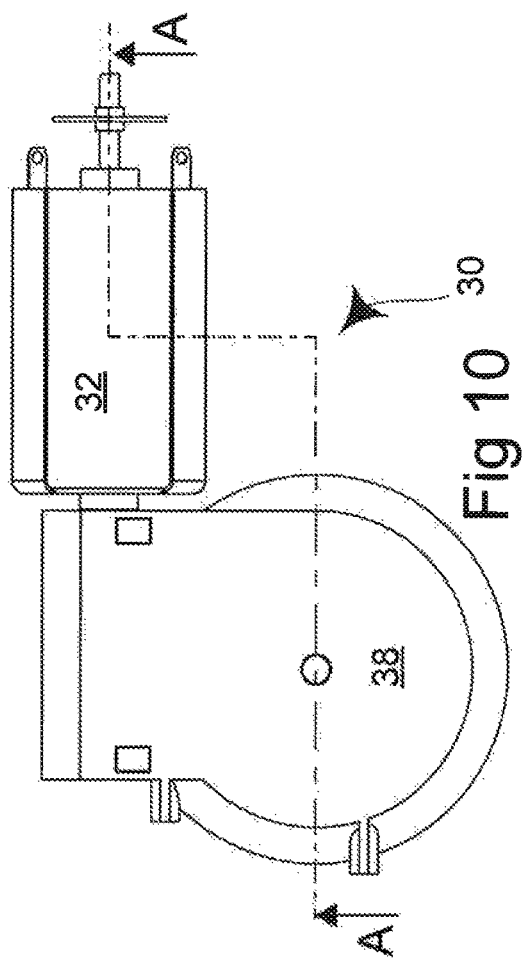

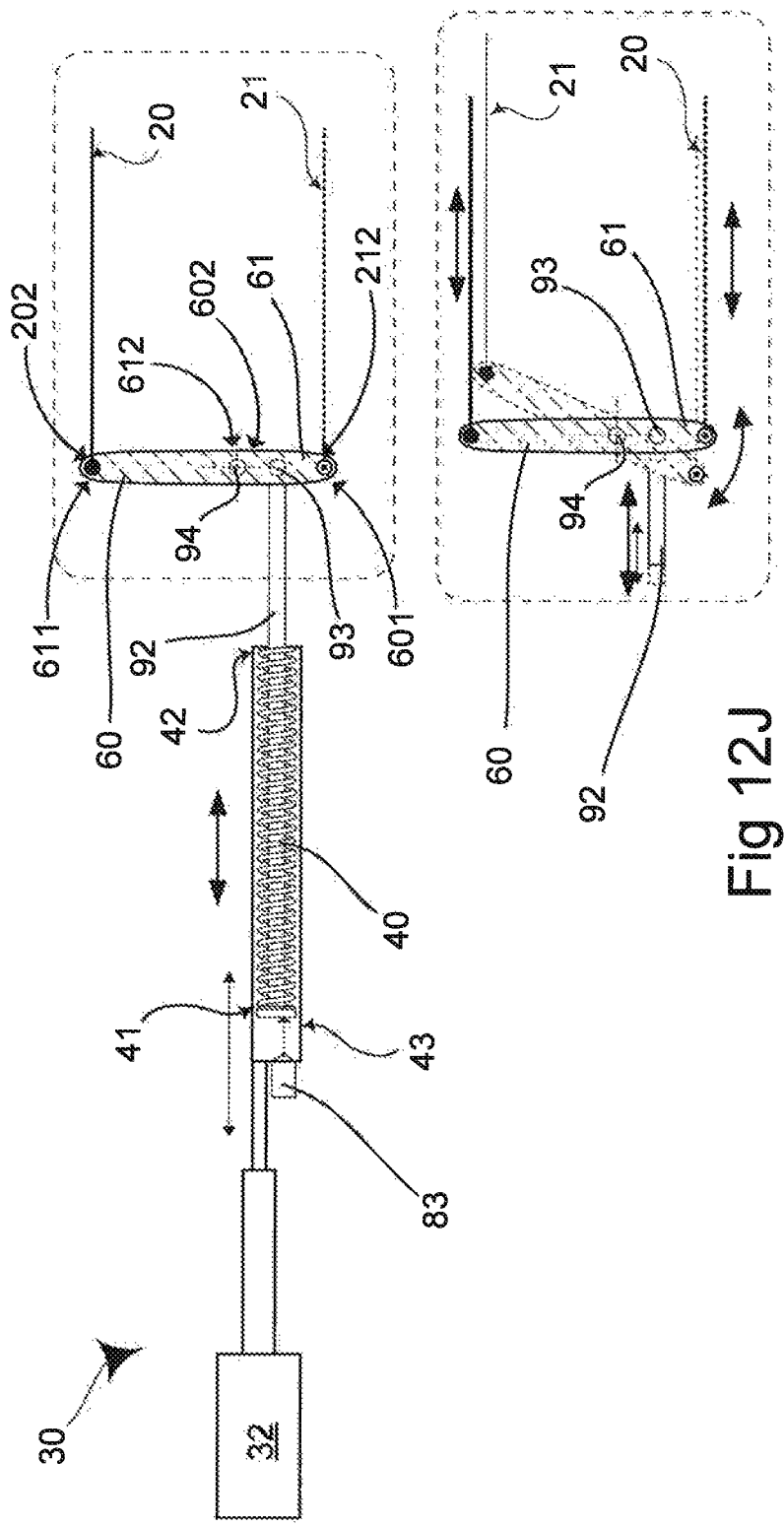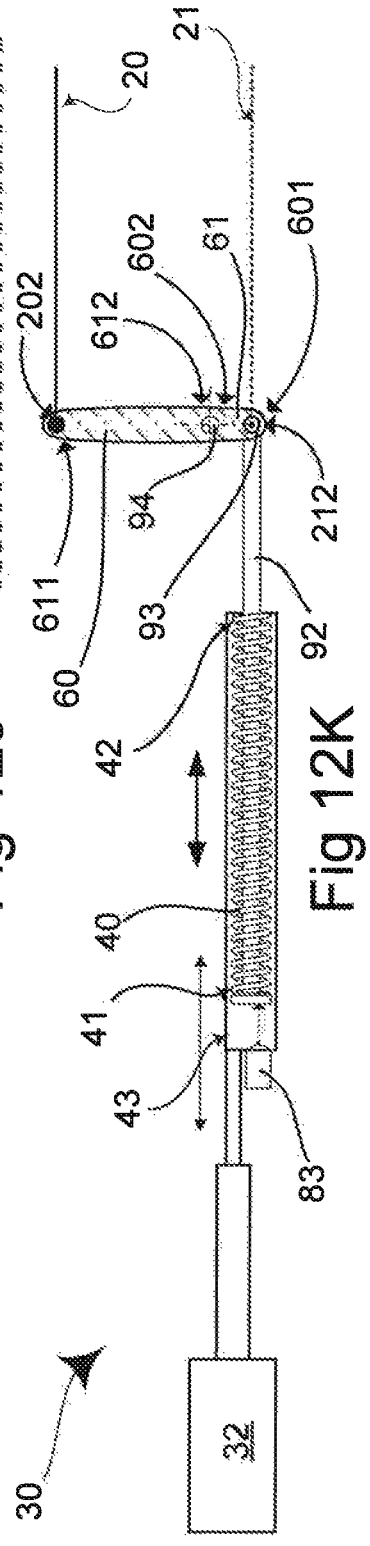
Fig 12J
Fig 12K

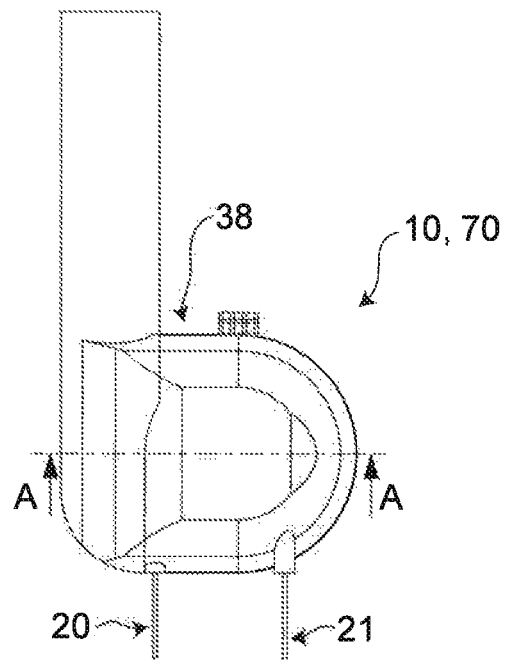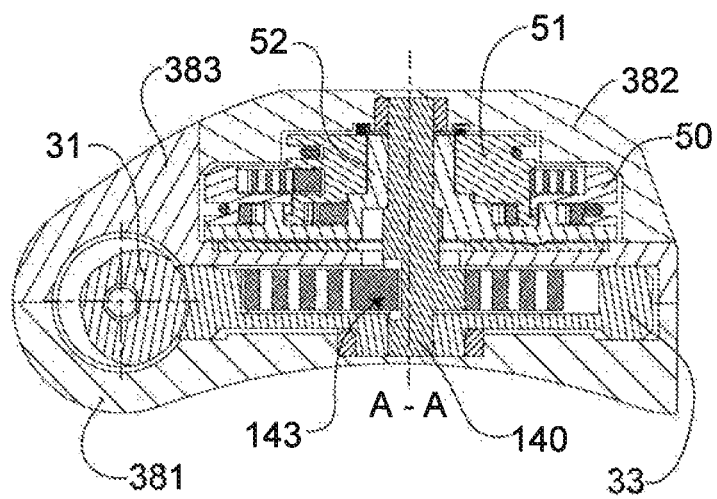
Fig 14C

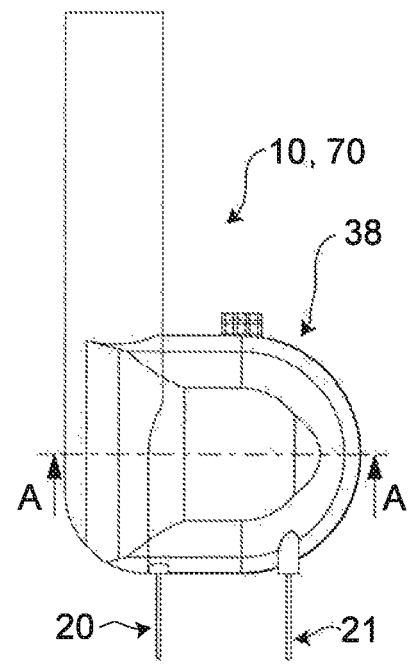
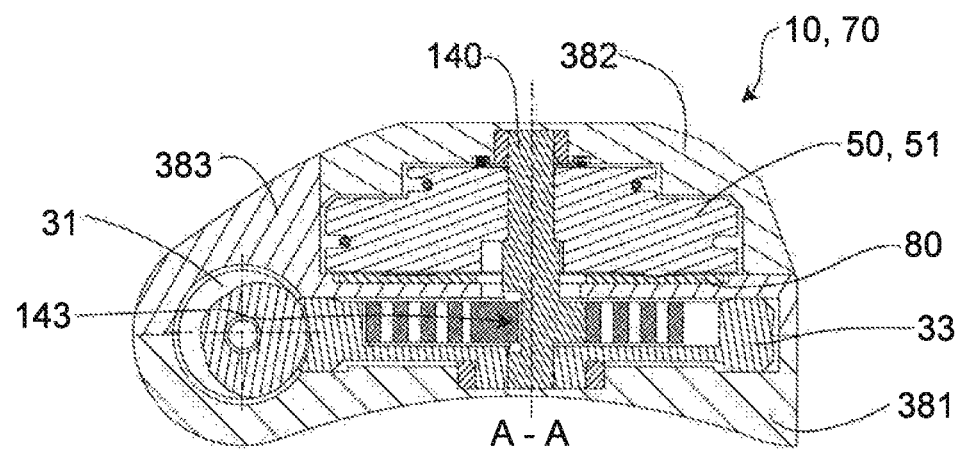
Fig 15B

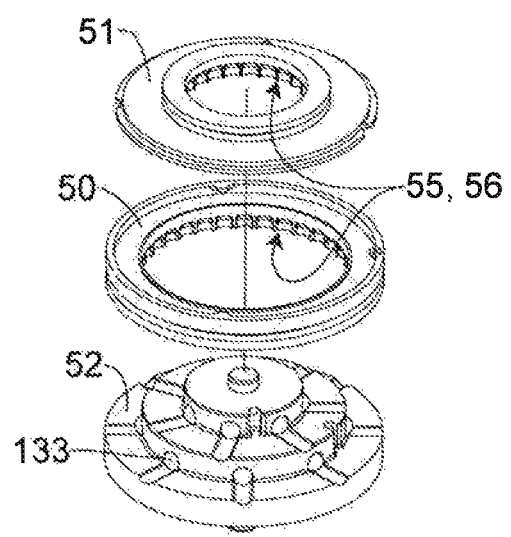
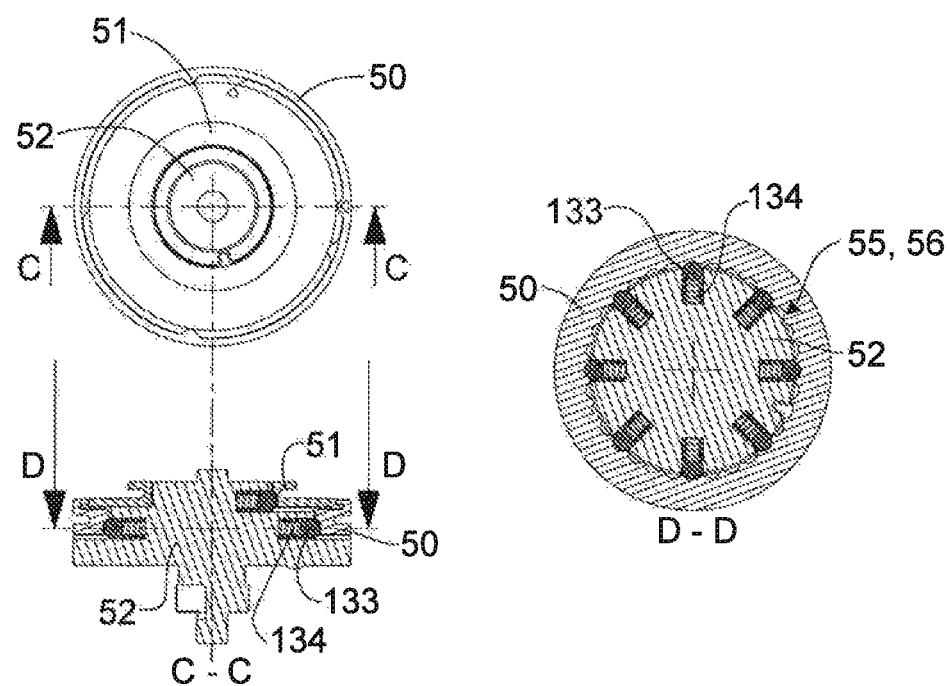
Fig 19B

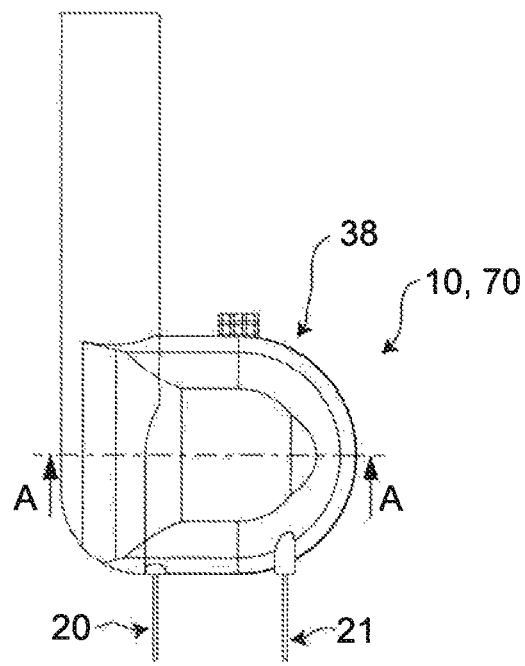
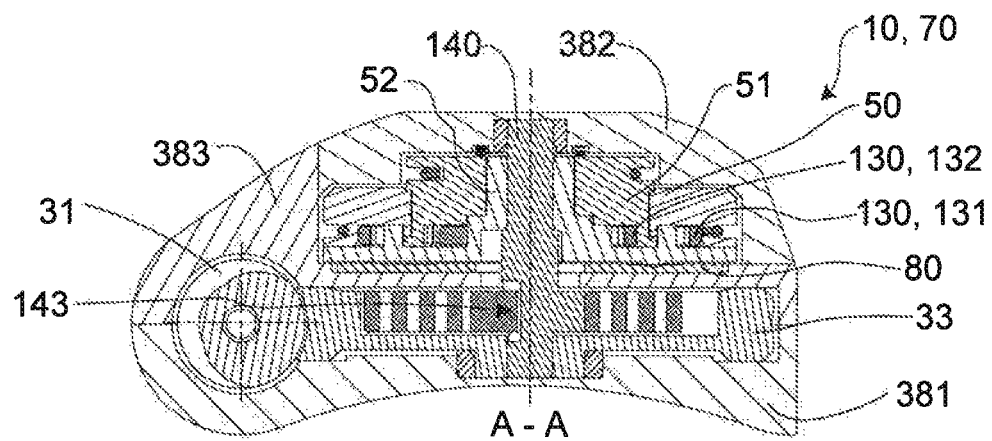
Fig 22B

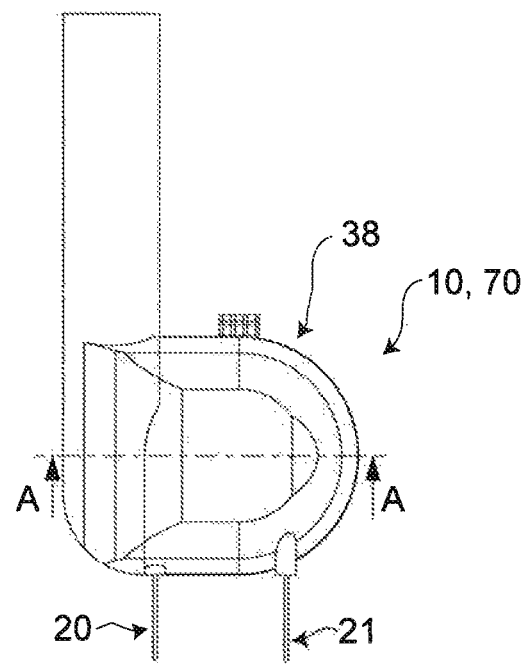
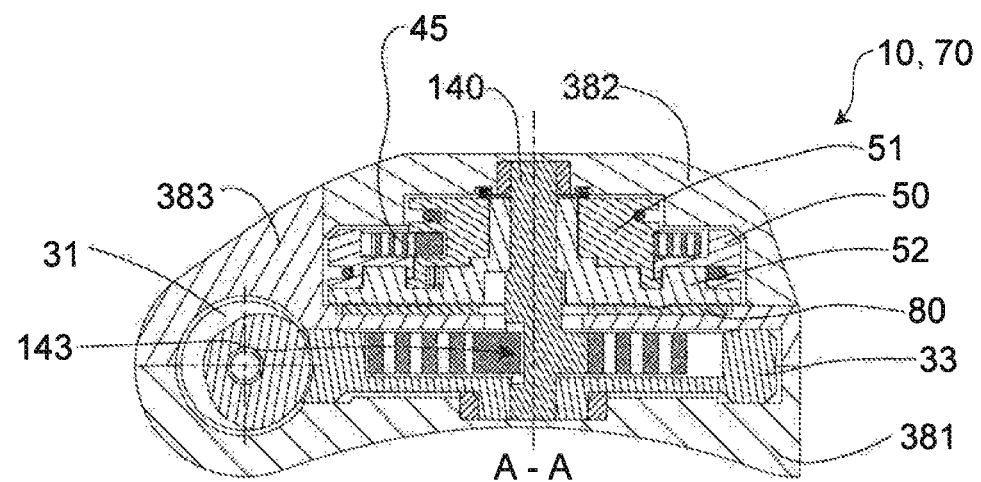
Fig 23B

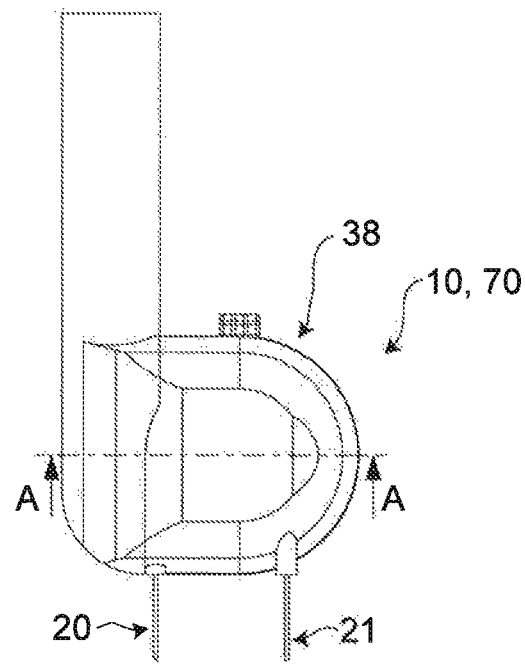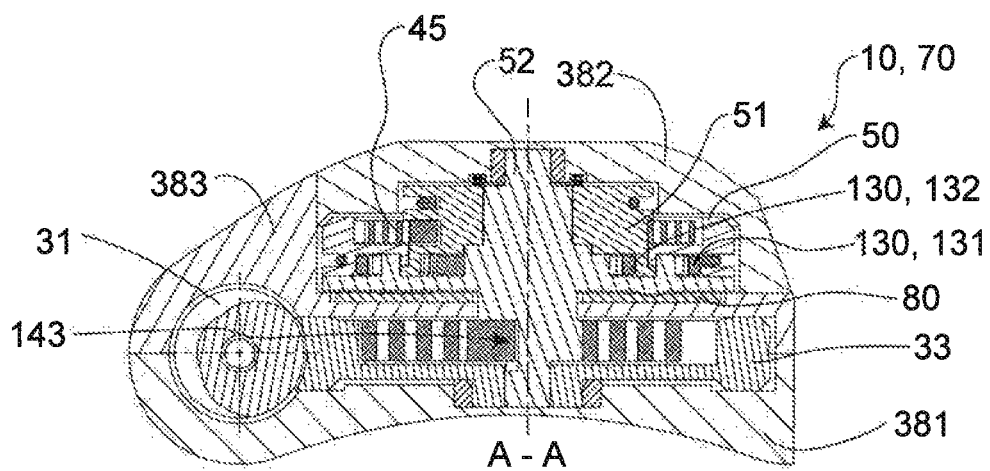
Fig 24B

DEVICE FOR MOVING AN ARM AND A METHOD OF OPERATING THE DEVICE

TECHNICAL FIELD

The invention relates to a device for moving, e.g. pivoting an arm being a human or artificial member or limb in relation to a joint, and a method of operating the device.

BACKGROUND ART

There are a lot of known devices for moving one or more parts of a human or artificial body, such as parts of exoskeletons and different areas within the medical and robotics field.

Another known technology is to use artificial tendons to help people with different types of mobility disabilities to move their limbs, such as legs, arms and fingers, and help them to grip and hold objects with their hands that need assistance to function as normal as possible.

Examples of usage of such artificial tendons to reduce the effort for humans with at least some degree of mobility disability are disclosed in the Swedish patent application no SE 1 550 532 A1 and in the Swedish patent no SE 530 293 C2.

However, the above prior art suffers from at least some disadvantages, e.g. helping the person in need to either only grip objects or let loose of them.

SUMMARY OF THE INVENTION

It is, accordingly, an object of the present invention to overcome deficiencies of the prior art, such as indicated above.

An object of the invention is to provide a device and method for artificial pivoting of an articulated arm, finger or similar in both directions.

Another object of the invention is to provide a device and method for assisted pivoting of an articulated arm, finger or similar in both directions.

Still another object of the invention is to provide a device and method for training an arm, finger or similar in both directions.

Yet another object is to provide a device and method driven by an electric motor, whereby power consumption is minimized.

A further object of the invention is to provide a device and method as mentioned above comprising at least two artificial tendons at each side of the arm or finger, whereby slack in each of the artificial tendons is at least minimized or even avoided.

A still further object of the invention is to provide a device and method as mentioned above for provision of a biasing force without slack in the tendons, i.e. each tendon follows the movement of the other tendon without being so relaxed or laxed that any slack occurs while simultaneously being held or kept stretched without any strain or preload or only with marginal strain or preload or only with minimum strain or preload being so low that each tendon is in principle kept stretched and lax at the same time when being moved or let in or out of the device, i.e. shortened or retracted in length or prolonged or extended in length. In other words, each tendon that follows another tendon is kept stretched and lax but without any preload, i.e. each tendon is kept non-slacked but stretched during the whole movement.

Another object of the invention is to provide a motor for operating the tendons, where motor transmission is self-inhibiting for maintaining a built-up force or built-up strain or built-up biasing force without consumption of electric power.

Still another object is to provide a device and method as mentioned above for artificial and/or assisted pivoting of several joints, for example several finger joints and/or several fingers/toes and/or all fingers/toes of a human person.

It is another object of the present invention to provide a device and method of operating the device to move an arm or limb being human or artificial in at least two directions, in one of the directions to contract and/or retract and/or turn down and/or fold and/or pivot the arm/limb in this first direction and in the other/second direction to extend and/or turn up and/or unfold and/or pivot the arm/limb in this other and/or opposite direction.

It is a further object of the present invention to provide a device and method of operating the device to move a human or artificial arm/limb at least bi-directionally by usage of at least two artificial tendons attached to the arm/limb, each artificial tendon being adapted to be pulled and/or slacked in response to which direction the arm/limb is moved or is to be moved.

It is still a further object of the present invention to provide a device and method of operating the device to move an arm/limb being human or artificial in at least two directions by means of using at least two artificial tendons attached to the arm/limb, so that a bi-directional movement is created without unnecessary slack in one tendon and too high strain/stress in the other tendon when this other tendon is pulled.

It is another object of the present invention to provide a device and method of operating the device to move a human or artificial arm/limb bi-directionally by means of at least two artificial tendons of which each is adapted to be pulled and slacked alternately enabling the bi-directional arm/limb movement without unnecessary slack and/or stretching in one tendon when another tendon is pulled and/or slacked by use of bias/biasing maintaining a predetermined and controlled preload of each tendon for slackless and stretch controlled movement of each tendon when following each other's movements.

It is another object of the present invention to provide a device and method of operating the device to move a human or artificial arm/limb bi-directionally by means of at least two artificial tendons of which each tendon is adapted to be pulled and to follow the movement of the other tendon without slack alternately enabling the bi-directional arm/limb movement without unnecessary slack and/or stretching in one tendon following the movement of another tendon being pulled by maintaining a predetermined and controlled stretch/lax of each tendon for slackless and stretch controlled movement of each tendon when following each other's movements.

Another object of the present invention is to provide a device and method of operating the device enabling moving a human and/or artificial arm or limb in at least two different directions by usage of one artificial tendon for each movement without any slack and/or stretching or at least without unnecessary slack and/or stretching in a tendon following movement of another tendon being pulled by use of bias/biasing that maintains predetermined and controlled zero or marginal preload, whereby synchronous stretch and lax of each tendon is enabled when it follows the movement of the other tendon, which biasing enables a drive or actuator of the device to stand still, i.e. not be operated, and not consume power/current, while enabling manual movement of the arm, e.g. for training muscles of one or more weak/faint body members, arms, necks and/or fingers of persons with mobility disability and/or lower/bad health, as an example during rehabilitation. This training may be done by manually pulling one or more weak/faint body members, arms, necks and/or fingers in one direction, i.e. in one tendon, so that the biasing works as an anvil/anchor/holding-on tool/counterstay making a resistance against the pulling, and then release/let go, whereby the biasing causes a pulling back force. This biasing is possible to adapt to the need of training and other health and/or physical requirements of each individual as the case may be.

A further object of the present invention is to add a dynamic feel to a grip between a finger and an object to be gripped or to a movement of a body member/arm/limb/finger while simultaneously provide direct feedback to any control system or unit for the current force in the tendon and the corresponding grip force as well as the position of any associated joint/limb/arm/finger.

Another object of the present invention is to provide a device and method of operating the device enabling moving a human and/or artificial arm or limb in at least two different directions by usage of one artificial tendon for each movement without slack and/or stretching in a tendon following movement of another tendon being pulled by use of a free wheel functionality that is in existence before any bias/biasing of each tendon is enabled when it follows the movement of the other tendon, which free wheel functionality also, as for the biasing functionality, but before the biasing "kicks in", enables a drive or actuator of the device to stand still, i.e. not be operated, and not consume power/current, while enabling manual movement of the arm, e.g. for one or more weak/faint body members, arms, necks and/or fingers of persons with mobility disability and/or lower/bad health being even weaker than for persons that cope with the biasing during rehabilitation, i.e. this free wheel functionality enables movement for people that are not able to physically overcome the biasing over a whole posture change from a fully bent finger to a fully extended and straight finger, in some cases, even bent in the other direction passing or beyond a straight finger, e.g. for a person with hyper mobility, without resistance from any biasing. This free wheel functionality also provides a security against any unexpected or undesired external force or impact that pulls one or more body members, arms, necks and/or fingers too quickly and/or strongly in one direction, i.e. in one tendon, risking injury/-ies or at least unnecessary pain or discomfort in the pulled members, arms, necks and/or fingers. This is enabled as a finger/limb/body member is able to move freely without resistance towards a bent position/posture for a certain size of this movement before the resistance of the biasing takes effect, this being an advantage both due to the above damage control and people with very weak finger/limb/body member, while still enabling a training effect when the biasing member thereafter is engaged/takes effect, in principle "kicks in". Subsequently, after the free wheel movement is finished or before, e.g. when the person is starting to grip an object, the device is operated so that any remaining "free wheel capacity" or movement is "catched up", whereafter the biasing starts taking effect as being engaged and are able to regulate a desired gripping force by increasing (or reducing) the biasing between the finger and any biasing member.

Yet another object of the present invention is to provide a device and method of operating the device enabling moving a human and/or artificial arm or limb in at least two different directions by usage of one artificial tendon for each movement, whereby the inventive design using at least two tendons at different sides or along different paths of at least one body member, such as one or more fingers, arms or limbs, being connected to the end of the body member in such a way that the tendons are always kept in safe and reliable connection and operative contact with the body member end without any risk of coming loose therefrom, e.g. by sliding off or the like, when the tendons follow each other's movement. This means that a fingertip is possible to be kept open, i.e. not covered on most of its area, in particular its underside, and only needing to cover the upper or dorsal side or fingernail side of the fingertip. Hence, by this solution keeping the tendons always stretched with no slack, the attachment of the ends of the tendons at the fingertip, e.g. in the form of soft fingertip coverage or small soft thimble-like member or the like, do not come off by sliding off or skidding off when the tendons move the fingertip. This is further improved by a balanced and optimized coordination of the simultaneous movement of the tendons according to the invention, but also due to the placement and arrangement of the tendons, i.e. how they are laid out along the body member/finger which the device is intended to "help" moving, achieving a perfect balance or counterbalance between the forces of the tendons on the fingertip and the pulling or pushing induced or exerted on the thimble so that it does not come off even though the fingertip is in fact almost completely unclothed or bare, i.e. non-covered on its underside, whereby in principle only the fingerprint area of the fingertip could be or is open/bare. However, in some cases, the opening of the fingertip could be larger than only the size of the fingertip, in principle the whole underside of the finger could be open/bare.

A further object of the present invention is to provide a device and method of operating the device enabling moving a human and/or artificial arm or limb in at least two different directions by usage of one artificial tendon for each movement, whereby a torque limiting effect is achieved to eliminate the risk of damaging a body part of a user that is using the device, e.g. a finger or other limb, or the device be damaged, if its driving mechanism and/or motor runs amuck or if the body part gets stuck in something or is impacted by or collides with something that incur an external force, either from the drive entity running wild or a tendon getting stuck in something and pulled very hard and quick, the torque limiter takes effect by, in principle, disengaging or discoupling the physical connection between the part that imparts the excessive force and the body member when the excessive force exceeds the connecting force. Another solution would be to simply let the affected tendon come loose or to break if a certain external force is exceeded, however, this solution is more difficult and cumbersome to reset before being able to use the device again compared to the above torque limiter by which the device would only have to be adjusted back to its earlier state as soon as the excessive force has ebbed away instead of replacing a broken tendon with a new one or reattaching the tendon to the device again, especially if the user is weak in hands and/or fingers and unable to perform such a repair.

Yet another object of the present invention is to provide a device and method of operating the device enabling moving a human and/or artificial arm or limb in at least two different directions by usage of one artificial tendon for each movement, whereby users with body members/hands of different sizes, e.g., in some cases the same user has differently sized hands from time to time due to swelling or the like are still able to use the same size of a device and tendons by providing a length adjustability being very easy to use and robust and accomplished manually and/or automatically.

Hence, the actuation device for the tendons is also detachable as a module or package together with the tendons and their attachment to the body member from the device. The actuation device could in some cases enable manual or automatic adjustment of the length of the tendons when attached to the device, or, in other cases, when detached, the actuation device could be manually manipulated to adjust the length of the tendons or do this automatically, e.g. if the device is at least partly made as a soft glove and/or only a soft thimble-like coverage of part of a finger and its fingertip it may require cleaning or be detachable from the device and tendons to be easily replaced if worn out or the like. This tendon length adjustment also enables at least a minor adjustment of the fit of the glove.

Still another object of the present invention is to provide a device and method of operating the device enabling moving a human and/or artificial arm or limb in at least two different directions by usage of one artificial tendon for each movement, by which all of the solutions/modules above and aspects below could be combined or only the free wheel functionality/module be used in the device or only the open fingertip solution/module be used in the device or only the torque limiting function/module be used in the device or only the tendon length adjustment function/module be used in the device or could the free wheel functionality/module be combined with the open finger-tip solution/module in the device or could the free wheel functionality/module be combined with the torque limiting function/module in the device or could the free wheel functionality/module be combined with the tendon length adjustment function/module in the device or could the torque limiting function/module be combined with the tendon length adjustment function/module in the device or could the open fingertip solution/module be combined with one or more of the above functionalities/modules in the device, the same goes for the below solution/-s concerning the inherent/built-in biasing effect of the device.

These objects are achieved by means of a device for pivoting an arm relative a joint, as claimed in the associated independent claims, preferred variants thereof being defined in the associated dependent claims.

At least one of the above and below and further objects are achieved by means of a device for pivoting an arm around a joint, the device comprising an actuation device arranged at a distal portion of the arm beyond the joint for generating a torque around said joint, a driving mechanism arranged at a proximal portion of the arm before the joint, and a motor for driving the driving mechanism, the actuation device comprising at least a first artificial tendon, a distal end of which is attached to the distal portion of the arm and extending in a first path along the arm beyond the joint and a proximal end of which is attached to the driving device, wherein the actuation device comprises at least a second artificial tendon, a distal end of which is attached to the distal portion of the arm and extending along a second path of the arm beyond the joint and a proximal end of which is attached to the driving device, wherein the driving device is arranged, when operated by the motor, to pull the first artificial tendon and simultaneously let the second artificial tendon to follow this movement of the first artificial tendon for generating a torque in a first direction around the joint, and to pull the second artificial tendon and simultaneously let the first artificial tendon to follow this movement of the second artificial tendon for generating a torque in a second direction around the joint providing a bi-directional movement of the body member with predetermined and controlled tightness or closeness to the body member for each tendon when it follows the movement of the other tendon; and a biasing member being arranged between the motor and the driving mechanism. The first path may be arranged at a first side of the joint and the second path may be arranged at a second side of the joint opposite of the first side. This tightness or closeness for the tendons mean that the tendons are able to follow the contour and shape of the body member, in particular a finger, without having to be sewn or otherwise attached to a glove or the like, however, if sewn to a glove this ability is further improved.

Further objects and features of the present invention will appear from the following definitions of aspects/examples of the invention.

According to an aspect/embodiment according to the below and above aspects, the device may further comprise a self-inhibiting drive member, which is arranged between the motor and the biasing member, wherein the self-inhibiting drive member is immobile when the motor is not operated. The drive member may be inherently self-inhibiting, for example such as a worm drive, or may comprise a brake, which is activated when the motor stands still for inhibiting movement of the drive member, or using a type of gearing being inert or very slow, e.g. due to inertial mass or the like, meaning that the gearing is difficult to activate before reaching a threshold force/torque.

According to another embodiment/aspect according to the below and above aspects, the driving mechanism may comprise at least one pulley and/or rotary arm, to which a proximal end of at least one of the first artificial tendons is attached. The driving mechanism may comprise a first pulley, with a first operative diameter, to which a proximal end of the first artificial tendon is attached, and a second pulley with a second operative diameter, to which a proximal end of the second artificial tendon is attached, whereby the first operative diameter is larger than the second operative diameter. Alternatively, according to the below and above aspects, the driving mechanism may comprise a first rotary arm with a first operative arm length, to which a proximal end of the first artificial tendon is attached, and a second rotary arm with a second operative arm length, to which a proximal end of the second artificial tendon is attached, whereby the first operative arm length is larger than the second operative arm length. The above operative diameters and lengths may in some aspects according to the below and above be almost the same or exactly the same depending on if a gearing is applied or not and what type of gearing.

In one aspect of the invention according to the below and above, one or more of the tendons are not directly attached to any driving mechanism but through at least one transmission e.g. a block and tackle system.

According to another embodiment/aspect according to the below and above, at least one tendon is not directly attached to the driving mechanism but to e.g. a tackle system consisting of at least one, but not limited to one, tackle and a fix/fixed/static/attachment end/point.

According to another embodiment/aspect according to the below and above, at least one tendon is not directly attached to the driving mechanism but via e.g. a tackle system consisting of at least one, but not limited to one, tackle and a fix/fixed/static/attachment end/point, in order to increase or decrease the pulling force between one or more tendons attached to the proximal end and one or more tendons attached to the driving mechanism.

According to a still further aspect/embodiment, the device according to the below and above may further comprise at least one elastic means at the artificial tendon for accommodating slack in the artificial tendon.

According to another embodiment, the device according to the below and above may further comprise a sensor for sensing the position of the driving mechanism and a sensor for sensing the biasing of the biasing member. The sensor for sensing the biasing of the biasing member may be a strain gauge applied to a leaf spring for sensing relative bending/position between a first and a second end and/or side of the leaf spring, or a position sensor for sensing relative position between a first and a second end of a rotary spring.

The device according to any one of the previous and below embodiments further comprises a sensor for sensing the position of the driving mecanism and/or one or more pulleys/rotary arms and a sensor for sensing linear movement or the angle of rotation in response to movement of each tendon to determine, i.e. enable detection/calculation of the biasing of the biasing member.

The above and below and further objects are also achieved by means of a method of operating the device for pivoting an arm relative a joint, as claimed in the associated independent method claim, preferred variants thereof being defined in the associated dependent claims.

At least one of the above and below and further objects are also achieved by a method of operating a device according to any of the preceding aspects/embodiments, comprising steps of arranging at least one body member with the device at a suitable position in relation to an object to be handled; moving the body member into physical contact with the object to be handled; detecting the movement of the body member by measuring a corresponding movement of at least one tendon of the device; operating a driving mechanism of the device in a first direction to bias the body member into firmer physical contact with the object until desired contact force is reached; stopping the operation of the driving mechanism when the desired contact force is reached; maintaining the correct contact force between object and the body member by means of a self-inhibiting functionality of the driving mechanism; operating the driving mechanism in a second direction to reduce the bias of the body member to zero and until the physical contact with the object has disappeared; arranging the device and at least one body member at another or the same suitable position in relation to another or the same object to be handled.

Further objects and features of the present invention will appear from the following definitions of aspects/examples of the invention.

According to some aspects, the method of operating the device according to the above and below may comprise a further step of detecting the movement of the body member by measuring the corresponding alternate movement of at least two tendons of the device.

These objects are also achieved by means of the following device for pivoting an arm relative a joint. Preferred variants thereof are defined in dependent claims and detailed description. Hence, the above and below and further objects are also achieved by a device for pivoting an arm relative and/or about/around a joint and/or bending/folding a bendable/foldable joint of an arm/limb comprises at least one artificial tendon attached to at least one and/or more members or parts or sections of one or more arms, which member or part or section may be arranged closer to or further from one or more joints, e.g. at the middle of the arm or between the middle of the arm and a joint and/or between a distal and/or free end of one or more of the arms/limbs and the joint i.e. at any suitable location between the distal and/or free end of one or more of the arms/limbs and the joint, and at least one driving mechanism, which driving mechanism is connected to and adapted to at least pull the tendon and the distal end of the arm/limb to bend/flex the arm/limb. This device further comprises at least one first tendon movably extending along a first side of the arm/limb and is attached with a first end to the proximal arm/limb end, and at least one second tendon movably extending along at least one second side of the arm/limb and is attached with a first end to the distal arm/limb end, and the driving mechanism is adapted to pull the first tendon and to slack the second tendon to extend the arm/limb and to pull the second tendon and to slack the first tendon to retract the arm/limb when operated, and that the device further comprises at least one biasing organ operatively connected to the driving mechanism and the tendons as an intermediary part to enable alternately pulling and slacking of the tendons without operating the driving mechanism. At least one tendon may also have at least one end split into two or more ends that may be attached to at least one and/or more members/parts/sections of one or more arms, which member or part or section may be arranged closer to or further from one or more joints, e.g. at the middle of the arm or between the middle of the arm and a joint and/or between a proximal and/or distal and/or free end of one or more of the arms/limbs and the joint, i.e. at any suitable location between the proximal and/or distal and/or free end of one or more of the arms/limbs and the joint. At least one tendon may also have at least one end split into two or more ends that may be attached to at least one and/or more distal members/parts/sections of a corresponding arm individually, i.e. each tendon may have one non-split end attached to the driving mechanism, wherein its other end being split has each sub-end attached to a corresponding part of an arm or a whole arm individually at any suitable location between the distal and/or free end of each arm/limb and joint.

According to one aspect, the device according to any of the above and below aspects features a first side arranged opposite and/or below and/or under and/or sideways/laterally relative a second side of the arm/limb.

In another aspect, the device according to any of the above and below aspects features the second side as being another side arranged opposite and/or above and/or sideways/laterally relative the first side of the first arm/limb. In another aspect, the device according to any of the above and below aspects further features the at least one second artificial tendon movably extending along a dorsal/upper side of the arm/limb and to the distal arm/limb end.

In still another aspect, at least two or more devices according to any of the above and below aspects may be provided on one and the same body member/arm/hand/leg. In yet another aspect, if at least one or more tendons has at least one split end being attached to several or all parts of the body member/arm/leg/hand or all the fingers of a hand, the advantage of using only one motor for moving several or all of those entities is achieved.

In one more aspect, at least two or more devices according to any of the above and below aspects may be provided on one and the same body member/arm/hand/leg/foot, whereby at least one device is adapted/arranged to be operated for contraction and extension of at least one finger, e.g. forefinger/index finger, while at least one other device is adapted/arranged to be operated for contraction and extension of at least another finger, e.g. the thumb. This arrangement of devices is likewise applicable on upper arm vs. forearm.

In yet some aspects according to the below and above: two or more tendons may be attached to one and the same driving mechanism and/or biasing means; and/or more than one, e.g. several devices may be used together to move different body members/arms/limbs/hands/fingers; and one and the same device may by itself be used to move several different body members, such as arms, limbs, hands and/or fingers.

In one aspect according to the below and above, the first tendon extends along the underside of a body part/member/finger and is adapted to bend this entity, while the second tendon extends along the upper side of the same body part/member/finger and is adapted to extend, straighten and/or stretch out this entity.

At least one of the above and below and further objects are achieved by means of a device for pivoting a body member around a joint, the device comprising an actuation device arranged at a distal portion of the body member beyond the joint for generating a torque around the joint, a driving mechanism arranged at a proximal portion of the body member before the joint, a motor for driving the driving mechanism, said actuation device comprising a first artificial tendon, a distal end of which is attached to the distal portion of the body member and extending in a first path along the body member beyond the joint and a proximal end of which is attached to the driving mechanism; which actuation device comprises a second artificial tendon, a distal end of which is attached to the distal portion of the body member and extending along a second path of the body member beyond the joint and a proximal end of which is attached to the driving mechanism, characterized in that the driving mechanism is arranged, when operated by the motor, to pull the first artificial tendon and simultaneously and actively enabling the second artificial tendon to follow this movement of the first artificial tendon for generating a torque in a first direction around the joint, and to pull the second artificial tendon and simultaneously and actively enabling the first artificial tendon to follow this movement of the second artificial tendon for generating a torque in a second direction around the joint providing a bi-directional movement of the body member with each tendon kept stretched but not strained when it follows the movement of the other tendon; and that a biasing member is arranged between the motor and the driving mechanism.

The device according to any of above and below aspects, wherein the driving mechanism comprises at least one pulley or rotary arm to which the proximal end of at least the first artificial tendon is attached, and that a free wheel member is arranged between the biasing member and the at least one pulley or rotary arm, such that when the first artificial tendon is pulled the pulley or rotary arm is moved freely without engaging the biasing member until a certain size or distance or length or degree of the movement is reached.

The device according to any preceding and below aspect, wherein the driving mechanism comprises at least one pulley or rotary arm to which each proximal end of at least the first artificial tendon and the second artificial tendon is individually attached, and that a free wheel member is arranged between the biasing member and the at least one pulley or rotary arm, such that when any of the artificial tendons is pulled the associated pulley or rotary arm is moved freely without engaging the biasing member until the certain size or distance or length or degree of the movement is reached.

The device according to any above and below aspect, wherein the first path is arranged at a first side of the joint and the second path is arranged at a second side of the joint at least partly or partly opposite the first side.

The device according to any preceding and below aspect, further comprising a sensor for sensing the position of the motor and a sensor for sensing linear movement or the angle of rotation in response to movement of each tendon and this is used to determine the position of the body member and to determine biasing of the biasing member and thereby the pulling force in each tendon.

The device according to any previous and below aspect, wherein the free wheel member has a first end in engagement with the biasing member and a second end arranged to be in or come into engagement with at least one pulley or rotary arm of the driving mechanism only in two separated and/or different angular/rotary positions for the pulley or rotary arm resulting from movement of at least one tendon in different directions.

The device according to any preceding and below aspect, wherein the second end of the free wheel member is adapted to only be in or come into engagement with the at least one pulley or rotary arm in a first angular/rotary position of the at least one pulley or rotary arm when the tendons have been moved a distance in one direction and only be in or come into in engagement with the at least one pulley or rotary arm in a second angular/rotary position when the tendons have been moved a distance in a opposite direction, whereby each pulley or rotary arm is moved freely between these two positions.

The device according to any above and below aspect, wherein the first artificial tendon is attached with its distal end to the distal portion of the body member and a fingertip coverage and the second artificial tendon is attached with its distal end to the distal portion of the body member and the same fingertip coverage, which fingertip coverage at least partly or partly or fully or only covers the dorsal and/or upper and/or nail side of the fingertip.

The device according to any preceding and below aspect, wherein the first and second pulley are arranged to be pairwise coupled together and detachably connected to the driving mechanism.

The device according to any previous and below aspect, wherein the first and second rotary arm are arranged to be pairwise coupled together and detachably connected to the driving mechanism.

The device according any preceding and below aspect, wherein the driving mechanism comprises a pulley hub to which the first and the second pulley are commonly and detachably coupled, and the first and second pulley are arranged to be rotatably locked together when assembled to the pulley hub and arranged to be rotatable relative each other when disassembled from the pulley hub.

The device according to any above and below aspect, wherein the driving mechanism comprises an arm hub to which the first and the second rotary arm are commonly and detachably coupled, and the first and second rotary arm are arranged to be rotatably locked together when assembled to the arm hub and arranged to be rotatable relative each other when disassembled from the arm hub.

The device according to any above and below aspect, wherein the first and the second pulley are rotatable relative each other via at least one biasing part when disassembled from the pulley hub, whereby the biasing part is arranged to urge the pulleys in opposite directions after disassembly from the pulley hub to pull or roll or wind in the tendons.

The device according to any preceding and below aspect, wherein the first and the second rotary arm are rotatable relative each other via at least one biasing part when disassembled from the arm hub, whereby the biasing part is arranged to urge the arms in opposite directions after disassembly from the arm hub to pull/roll in the tendons.

The device according to any of the above and below aspects, wherein the driving mechanism comprises a first torque limiter arranged between the pulley hub and the first tendon and a second torque limiter arranged between the pulley hub and the second tendon.

The device according to any above and below aspect, wherein the driving mechanism comprises a first torque limiter arranged between the pulley hub and the first tendon and a second torque limiter arranged between the pulley hub and the second tendon, each torque limiter is rigidly or stationary or non-rotary attached to the pulley hub or its associated pulley and coupled to its associated tendon by means of an anchoring, whereby each pulley is rotatably locked together with the pulley hub as long as the force from any pulling tendon and/or the motor is less than the anchoring force between each torque limiter and its associated tendon.

The device according to any preceding and below aspect, wherein the driving mechanism comprises a first torque limiter arranged between the pulley hub and the first pulley and a second torque limiter arranged between the pulley hub and the second pulley, each torque limiter being rigidly or stationary or non-rotary attached to the pulley hub and coupled to its associated pulley by means of an anchoring, whereby each pulley is rotatably locked together with the pulley hub as long as the force from any pulling tendon and/or the motor is less than the anchoring force between each torque limiter and its associated pulley.

The device according to any of the previous and below aspectss, wherein the driving mechanism comprises a first torque limiter arranged between the arm hub and the first rotary arm and a second torque limiter arranged between the arm hub and the rotary arm, each torque limiter being rigidly or stationary or non-rotary attached to the arm hub and coupled to its associated rotary arm by means of an anchoring, whereby each rotary arm is rotatably locked together with the arm hub as long as the force from any pulling tendon and/or the motor is less than the anchoring force between each torque limiter and its associated rotary arm.

The device according any of the above a and below aspects, wherein the anchoring between each pulley and each torque limiter is achieved in that each torque limiter is deformable or flexible at its anchoring with its tendon or pulley or rotary arm, such that when the force from any pulling tendon and/or the motor is larger than a deforming or flexing force of each torque limiter, the anchoring between each torque limiter and its associated tendon or pulley or rotary arm is disengaged rotatably.

The device according to any preceding and below aspect, wherein the driving mechanism comprises a set of pairwise coupled pulleys comprising a first pulley or rotary arm to which the proximal end of at least the first artificial tendon is attached and a second pulley or rotary arm to which the proximal end of at least the second artificial tendon is attached, and a free wheel member is arranged between the biasing member and both pulleys or rotary arms, such that when any of the artificial tendons is pulled the associated pulley or rotary arm is moved freely without engaging the biasing member until a certain size or distance or length or degree of the movement is reached.

The device according to any preceding and below aspect, wherein the driving mechanism comprises two sets of pairwise coupled pulleys or rotary arms to which two first artificial tendons and two second artificial tendons are attached, one first artificial tendon to each pair of pulleys and one second artificial tendon to each pair of pulleys, and that a free wheel member is arranged between the biasing member and each set of pairwise coupled pulleys or rotary arms, such that when any of the artificial tendons is pulled the associated pair of pulleys or rotary arms is moved freely without engaging the biasing member until a certain size or distance or length or degree of the movement is reached. Moreover, one or more or both or all of the above pairwise coupled pulleys or rotary arms to which two first artificial tendons and two second artificial tendons are attached, one first artificial tendon to each pair of pulleys and one second artificial tendon to each pair of pulleys, are adapted to rotate around a mutual axis.

The device according to any one of the previous and below aspects, further comprising an elastic means at the artificial tendon for accommodating slack in the artificial tendon.

Further objects and features of the present invention will appear from the following detailed description of aspects/examples of the invention.

BRIEF DESCRIPTION OF THE DRAWINGS

The invention will now be explained in further details with reference to the drawings showing aspects thereof.

FIGS. 1A, 2A, 3B, 3D, 3I and 3K are views of one state of a human hand equipped with at least one, two or more devices achieving bi-directional operation of at least one, two or more arms/limbs according to aspects of the invention.

FIGS. 1B and 2B are views of another state of the human hand equipped with one or more of the device achieving bi-directional operation of at least one, two or more arms/limbs according to aspects the invention in FIGS. 1A, 2A, 3B, 3D, 3I and 3K.

FIGS. 3A, 3C, 3E-3G, 3H, 3J, 3L, and 3M are views of different configurations/aspects of one or more of the devices of FIGS. 1A-2B, 3B, 3D, 3I and 3K for achieving controllable force/torque transferred to and from at least one, two or more arms/limbs during bi-directional operation according to aspects of the invention.

FIG. 4 is a perspective view of the configuration/aspect of the device in FIG. 3A.

FIGS. 5A-5F are views of which FIGS. 5A-5E are partially sectioned showing different configurations/aspects of the device of FIGS. 1A-4 and at least one biasing mechanism enabling resilient/flexible bi-directional operation of arms/limbs according to aspects of the invention.

FIGS. 6A and 6B are perspective views of which 6B is partially cut to show at least a part of the inside of the device of FIGS. 1A-5F with at least one actuator.

FIG. 7 is a cross-sectional view of partly the inside of device in FIG. 8C showing one configuration of at least one actuator used in the device according to aspects of the invention.

FIGS. 8A-C are cross-sectional side views of different configurations of the actuator solutions of FIGS. 6A and 6B.

FIG. 9 is a schematic exploded view in perspective of the device in FIGS. 1A-8C showing an aspect of a feedback and positioning system for the actuator of the device according to the invention.

FIG. 10 is a planar side view showing the device of FIG. 9 from above.

FIG. 11 is a cross-sectional side view of the device of FIG. 10 along line A-A.

FIGS. 12A-12K are views showing different configurations/aspects of transmission and/or drive solutions used in the device of FIGS. 1A-11 according to the invention.

FIGS. 14A, 14B and 14C show several views of an aspect of the device according to the invention with all features. FIG. 14A shows the device in perspective and an exploded upper view of the device according to the invention where the device is disassembled into five different modules I, II, III, IV and V, and FIG. 14B shows an exploded view where the modules in FIG. 14A are exploded to reveal their parts disassembled. FIG. 14C shows a view in section along line A-A of another view from above of the device as assembled.

FIGS. 15A and 15B show several views of another aspect of the device according to the invention with some of all features. In FIG. 15A, the left view is an exploded view showing modules II and III of FIG. 14A further exploded and the upper right view shows module IV of FIG. 14A from below. FIG. 15B shows one view from above of the device as assembled and one view in section alone line A-A of this version of the device as assembled.

In FIG. 18A, the left view is an exploded perspective view showing modules II and III of FIG. 14A, and the upper middle view shows an exploded view in perspective of module IV of FIG. 14A at an angle from above and the upper right exploded perspective view shows module IV of FIG. 14A at an angle from below instead. In FIG. 18B, the device is shown from above and in a sectional view along line A-A as assembled.

FIG. 19B shows another version of module IV of FIGS. 18 and 19A in perspective and exploded view to the left and in section in the middle view and from above in section in the right view along line C-C in the middle view.

In FIG. 20A, to the left is an exploded view showing modules I to V of FIG. 14A and the right view shows an exploded view of module IV of FIG. 14A. FIG. 20B shows the device is shown from above as assembled and in a sectional view along line A-A as assembled.

In FIG. 21B, the upper left view shows module IV in perspective and assembled, the upper right view shows this module in an exploded view as disassembled and the middle views show this module from above and in section along line A-A. In FIG. 21A, the functionality of this module IV is visualised in two partly sectional views to the left taken along line B-B of the lower middle view in FIG. 21B when the device is taken off a body member in the lower left view and when taken on in the lower right view, this functionality being initiated when the module IV is detached from the device in the lower left view and attached to the other modules I and III of the device in the lower right view seen as two lowermost perspective views of FIG. 21B. The arrow pointing to the right in the lower view of FIG. 21A visualises how the glove is stretched when taken on before the module IV is again attached to the device.

FIGS. 22A and 22B show several views of a further aspect of the device according to the invention with some of all features. In FIG. 22A, to the left is an exploded view showing modules I to V of FIG. 14A with modules II and III further exploded (the version of module II is as shown in FIGS. 15A and 15B) and the upper right view shows an exploded view of another version of module IV of FIGS. 14A, 14B, 18A, and 18B. In FIG. 22B, the device is shown from above as assembled and in a sectional view from the side along line A-A of the device as assembled.

FIGS. 23A and 23B show several views of yet a further aspect of the device according to the invention with some of all features. In FIG. 23A, to the left is an exploded view showing modules I to V of FIG. 14A with modules II and III further exploded and the upper right view shows an exploded view of the version of module IV of FIGS. 14A, 14B, 20A and 20B. In FIG. 23B, the device is shown from above as assembled and in a sectional view along line A-A as assembled.

FIGS. 24A and 24B show several views of one more aspect of the device according to the invention with some of all features. In FIG. 24A, to the left is an exploded view showing modules I to V of FIG. 14A with modules II and III further exploded (with the version of module II as shown in FIGS. 18A, 18B, 20A and 20B), and the upper right view shows an exploded view of the version of module IV as in FIGS. 14A, 14B and as a version being a combination of those on FIGS. 20A, 20B and 23A, 23B with those on FIGS. 18A, 18B and 22A, 22B. In FIG. 24B, the device is shown from above as assembled and in sectional view of the device as assembled.

DETAILED DESCRIPTION

Figure 3G:
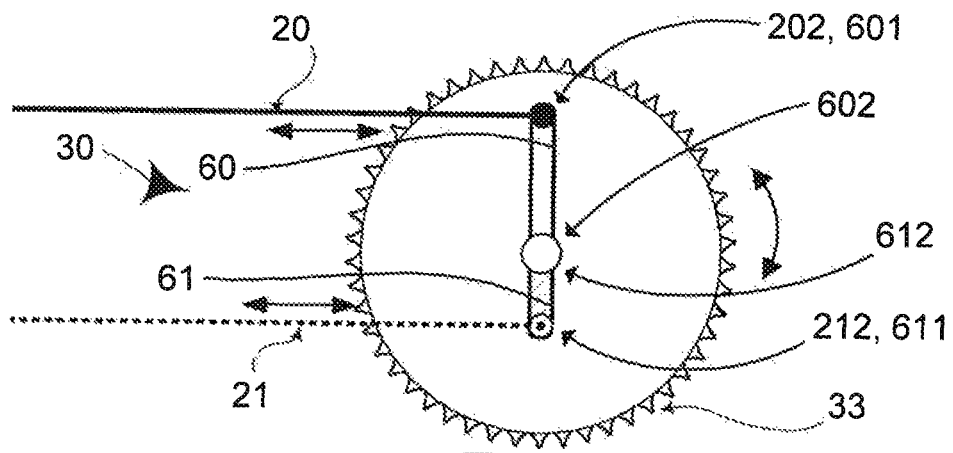

Aspects of the invention are disclosed below by reference to FIGS. 1A to 26.

FIGS. 1A to 2B, 3B, 3D, 3I, 3K, 17A, 17B, 21A, 25 and 26 show a hand/body part/member 4 of a human in at least two different postures equipped with at least one or more devices 10 according to the invention for moving, e.g. by pivoting an arm 2, in this case at least one or more fingers, relative and/or about at least one joint 1. The arm 2 may be one or more limbs/parts of a human body, such as fingers, legs, arms, foots or necks or the like, and/or one or more similar parts of an artificial body, robot and/or exoskeleton. The joint 1 may be one or more joints of a human body, e.g. a finger-joint, a knee joint, elbow joint, a wrist, an ankle and/or a part of a backbone, spine or the like and/or joint 1 with similar functionality on an artificial body and/or exoskeleton. Movement induced by the inventive device 10 may be rotational movement of a humans head on its neck, rotating and/or at least pivoting the arm or member or finger 2 about one or more joints 1 one by one and/or about two or more joints 1 more or less simultaneously (axis of rotation about the joint 1 may be perpendicular to the extension of the arm/finger 2, i.e. in parallel with the lateral extension of the arm/finger 2, and/or in parallel with the longitudinal extension of the arm/finger) for extension and/or retraction and/or folding and/or unfolding of the finger 2 and/or be a combination of one or more of these types of movements, depending on application.

Referring to FIGS. 1A to 2B, 3B, 3D, 3I, 3K, 17A, 17B, 21A, 25 and 26 the invention concerns the at least one device 10 provided on or at one or more limbs/fingers 2 of the body/hand 4. The device 10 comprises at least one actuation device, which comprises at least one or more first artificial tendons 20 (shown with solid line in FIGS. 2A, 2B, 3A-3K, 4, 5A-5F, 12J-12K, 14A, 14B, 15A, 15B, 16, 18A, 18B, 19A, 19B, 20A, 20B, 21B, 22A, 22B, 23A, 23B, 24A, 24B, and in dashed/broken lines in FIGS. 17A, 17B, 21A, 25 and 26) and at least one second artificial tendon 21 (shown with solid line in FIGS. 1A, 1B, 14A, 14B, 15A, 15B, 16, 17A, 17B, 18A, 18B, 19A, 20A, 20B, 21A, 21B, 22A, 22B, 23A, 23B, 24A, 24B, 25 and 26, and with broken/dashed line in FIGS. 2A, 2B, 3A-3K, 4, 5A-5F, and 12J-12K) movably attached at different sides 2a, 2b along the finger 2 on the hand 4. Each tendon 20, 21 is connected with at least one first end 201, 211 to at least one distal or free end 3 and/or front/face/part 3a of finger 2 and at least one driving mechanism 30 with at least one second end 202, 212, respectively.

The first end 201 of the first tendon 20 may be attached to a member 3a put or thread on the fingertip 3 of the finger 2, which member 3a is more or less hard/soft and shaped as a small hat or thimble or loop or bracket fitting over or around the fingertip to be able to move the fingertip placed at/on and/or inside it when the tendon pulls this thimble-like member, which thereby moves the finger inside it by forcing the finger to physically follow it. However, the fingertip is preferably not covered to enable fingertip sensitivity. Similar attachment to this thimble-like member 3a may be done for the first end 211 of the second tendon 21 to give it the same anvil or anchoring effect to pull for moving the finger 2, but not necessarily at the same location as the first tendon end 201. The driving mechanism 30 is connected to and adapted to pull the second end 202 of the first tendon 20 movably extending along a first/other/lower side and/or underside/inside side 2a of the finger when moving, extending and/or pivoting the finger 2 and its distal end 3 clockwise, i.e. downwards into a posture shown in FIGS. 1B, 2B, 17B, and 26 with the finger 2 retracted/pulled in/bent, about at least one of its joints 1 (the finger 2 has three joints 1, one joint closer to its free end 3 (=fingertip), one middle or intermediate joint and one joint close to or at the drive mechanism 30). If the device 10 is applied on another limb/body part, e.g. on the hand or the forearm while the tendons 20, 21 are arranged to move one or more fingers 2, one or more joints 1 and one or more drive mechanisms 30 may be arranged further away from or closer to each other depending on the size/length of arms/fingers and each tendon and the individual adaptation to the person in need. When the first tendon 20 is pulled, the second or other tendon 21 is slacked in a corresponding but opposite way/direction in response to the pulling, however, this movement is more of an active pulling of one tendon while the other tendon is in fact only following the movement of the one tendon being pulled in such a way that the other tendon has no slack, i.e. this is a non-slacking bidirectional guiding and moving of soft tendons relative each other. The driving mechanism 30 is connected to and adapted to pull the second end 212 of the second tendon 21 movably extending along a second/dorsal/upper side 2b of the finger when moving, extending and/or pivoting the finger 2 and its proximal end 3 (=fingertip) counter-clockwise, i.e. upwards into a posture shown in FIGS. 1A, 2A, 3B, 3D, 3I, 3K, 17A, 21A, 25 and 26 with the finger 2 extended, about at least one of its joints 1. When the second tendon 21 is pulled, the first or other tendon 20 is slacked but not loose, i.e. not being bent or wrinkled, only somewhat relaxed or lax but still kept tight and guided in still close proximity to the finger along its whole length, i.e. both its length and the length of the finger, as if it was pulled and not only following the other tendon along the finger in a corresponding but opposite way/direction in response to the pulling.

The degree of slacking and pulling the tendons 20, 21 alternately may be synchronized so that the simultaneous slacking occurs "faster" than the pulling, whereby no resistance or stress is incurred in the slacking tendon during pulling in the other tendon, or the slacking may be performed slower than the pulling, whereby resistance or stress incurred in the slacking tendon is controllable dynamically so that it is kept low or only marginal for keeping it tight against and along the finger 2 during pulling in the other tendon, the same goes for the other tendon when not pulled but following the tendon being pulled, this also being done for any other limb or body member besides a finger 2. The alternating moving of the tendons is more of an equally balanced or counter-balanced drag of one or more tendons 20 and actively letting one or more of other tendons 21 follow the others movement without slack. The object of keeping the slacked tendon at least somewhat biased is mainly to keep its slack at a minimum or preferably zero, i.e. each tendon is kept stretched when moved. The tendons 20, 21 in associated figures are not biased/preloaded individually when two pulleys 50 and 51 with different diameters are integrated, i.e. only FIG. 8B shows an aspect where each pulley is provided with its own biasing means 40 making each pulley manually movable independently of the other pulley. Hence, the slacked tendon is kept at least somewhat stretched or even stretched tight. This cooperation or joint action or interaction between the pulling and slacking of tendons in response to each other's movements is controlled by means of mechanical design of the device 10, the control of operation of driving mechanism 30 and its drive or actuating parts and/or its specific design and/or a combination of these aspects that will be explained below. However, in most aspects, the driving mechanism 30 comprises a worm wheel 33 of a transmission 31, such as a worm gear to create a space saving and self-inhibiting functionality for better safety and is driven by an electric motor 32 operatively connected to a motor controller 321.

Figure 13:
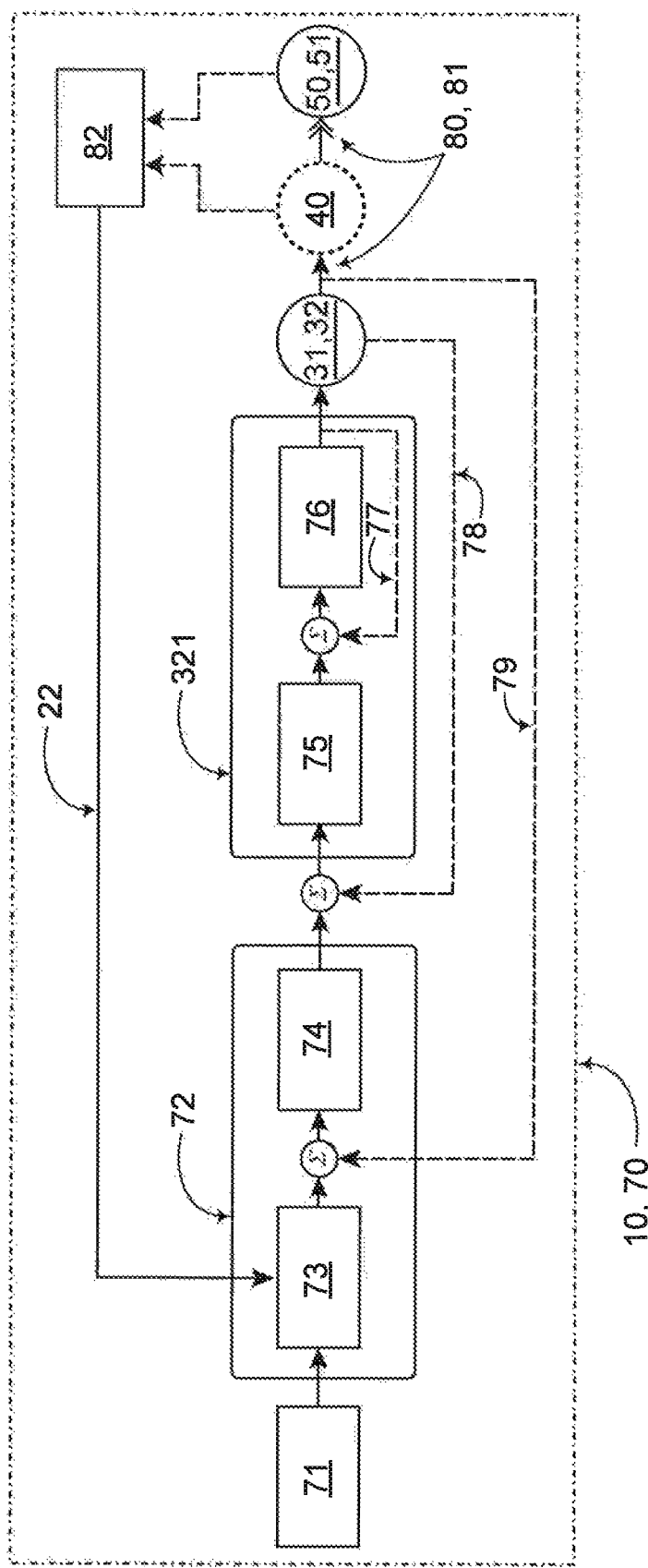
FIG. 13 is a flow chart schematically showing a system and method for operation of the device of FIGS. 1A-12K according to the invention.

An aspect/example of a control system for the device 10 is shown in FIG. 13 where the control system consists of a motor controller 321, a micro controller (MCU) 72, the self-inhibiting gear 31 and motor 32, a biasing organ 40, and tendon activating/actuating means, e.g. pulleys 50, 51 and/or rotary arms 60, 61. Control of said system is performed by signal acquisition, i.e. an activation signal 71 is sent to the control application 73 in the MCU. The tension of the biasing organ 40 is given by the angular difference between the self-inhibiting gear 31 and the pulleys/rotary arms 50, 51, 60, 61 is calculated in 82 and sent to the MCU 72 as a feedback signal 22. A position controller 74 for the motor 32 responds from the error signal given from the control application 73 and a motor position feedback 79 by acting as input to the motor controller 321 with an internal current control 76, 77 and a velocity controller 75. In one other aspect, the motor controller 321 comprises the velocity controller 75, a current controller 76, a current feedback 77 and velocity feedback 78 (see FIG. 13). This motor controller 321 is operatively connected to the micro controller (MCU) 72 comprising the control application 73, the position controller 74, these controllers 72, 73, 74 also being operatively connected to the signal input device/acquisition 71 and the motor position feed-back 79. The MCU 72 is also operatively connected to a tendon tension sensor for feedback signal 22 in turn being operatively connected to a control unit 82 for detection and control of relative position between winding parts, e.g. the worm gear/screw 31 being a self-inhibiting entity and/or at least one motor 32, and the tendon moving parts 50, 51, 60, 61 to which the tendons 20, 21 are operatively attached, to enable determination of the biasing of the bias organ 40. All of the above components are also operatively controlled by a control unit 70 of the device 10 (see FIG. 13).

In FIGS. 3A to 4, various side/top views of different configurations/aspects or designs of the device 10, i.e. solutions of transferring force/torque directly to and/or from the second end 202, 212 of each tendon 20 and 21, respectively, to move the arm/finger 2 are shown. In FIGS. 3A to 4, and 14A to 26 (except for FIG. 3G), the driving mechanism 30 comprises at least one pulley 50, 51 to which the second end 202, 212 of each tendon 20, 21 is attached. The second end 202, 212 of the tendon 20, 21 is securely attached to the outer periphery of the associated pulley 50, 51, so that the tendon may be winded onto or be unwinded from the pulley in response to the direction of movement of the pulley, i.e. the direction of movement of the arm/finger 2, whereby one or more tendons is/are winded in while one or more other tendons is/are unwinded but kept straight/tight against the body member. In FIG. 3G, the driving mechanism 30 is shown comprising at least one rotary arm 60, 61 to which the second end 202, 212 of one or more or each tendon 20, 21 may be attached. The second end 202, 212 of the tendon 20, 21 is securely attached to a free end 601, 611 of the associated rotary arm 60, 61, so that the tendon may be pulled or slacked by the free end 601, 611 of the rotary arm in response to the direction of movement of the pulley, i.e. the direction of movement of the arm/finger 2. The other end 602, 612 of the rotary arm may in one aspect be fixedly or removably but securely attached to at least one bias/biasing mechanism/organ 40 and the transmission 31, i.e. self-inhibiting gear/screw 31 of driving mechanism 30. At least one or both pulleys 50, 51 may in one aspect be operatively connected to the bias/biasing member 40 and the self-inhibiting gear 31.

In FIGS. 3C and 3D, the driving mechanism 30 comprises at least two larger pulleys 50 of different sizes and/or almost the same or the same size, i.e. with different diameters and/or almost the same or the same diameter D, D', and at least two smaller pulleys 51 of different sizes and/or almost the same or the same size, i.e. with different diameters and/or almost the same or the same diameter d, d'. The smaller diameter d of the single smaller pulley 51 and the larger diameter D of the single larger pulley in FIG. 4 are applicable also for the twins/pairs, or even a greater number of pulleys, of smaller and/or larger pulleys 50, 51 in FIGS. 3C and 3D, i.e. at least one of the smaller 51 and/or the larger pulleys 50 may have a diameter d and D, respectively, and at least one of the other small 51 and/or large pulley 50 may have different sizes and/or almost the same or the same diameter d' and D', respectively. In these figures, the second end 202 of each first tendon 20 is attached to the outer smaller periphery of at least one associated smaller pulley 51. In these figures, the second end 212 of each second tendon 20 is attached to the larger outer periphery of at least one associated larger pulley 50. In one aspect combined with any of above aspects, the driving mechanism 30 comprises at least two pulleys 50, 51 of different sizes, i.e. different diameters to which the second ends 202, 212 of the tendons 20, 21 are attached individually.

In FIG. 3G, the driving mechanism 30 is shown comprising at least one longer rotary arm 60 with the free end 601 to which the second end 212 of one or more or each second tendon 21 is attached. Here, the driving mechanism 30 is shown comprising at least one shorter rotary arm 61 with its free end 611 to which the second end 202 of one or more or each first tendon 20 is attached. In one aspect, the driving mechanism 30 comprises at least two rotary arms 60, 61 of different lengths, each arm having its first end 601, 611 operatively connected to the biasing organ 40 and its second end 602, 612 attached to the second end 202, 212 of at least one tendon 20, 21.

In FIGS. 1A, 1B, 2A, 2B, 3A, 3B, 3C, 3D, 3H, 3I, 3J, 3K, 4, 5A to 11, and 14A to 26), each pulley or spool 50, 51 is of circular shape, while in FIGS. 3E and 3F, each pulley 50, 51 has a cam shape. A cam shape actuates a tendon 20, 21 in different ways, e.g. a quick "start" movement is initiated with smaller force, which movement then slows down and pulls "harder"/with larger force in the associated tendon as the actuating "lever length" changes, i.e. its actual diameter of a pulley 50, 51. According to the aspects of FIGS. 3A to 3K, the pulleys/wheels/spools/cam wheels 50, 51 and/or rotary arms/linkages 60, 61 may be mounted on a sprocket. In other aspects, the different strings/tendons/pulleys/arms 20, 21, 50, 51, 60, 61 could control one finger 2 (e.g. control the different joints 1 in a finger in different ways) or other joints, but they could also push several fingers or joints in the same or different directions, for example all fingers could be contracted when just one pulley 50, 51 spins or one arm 60, 61 moves.

Figure 3L:
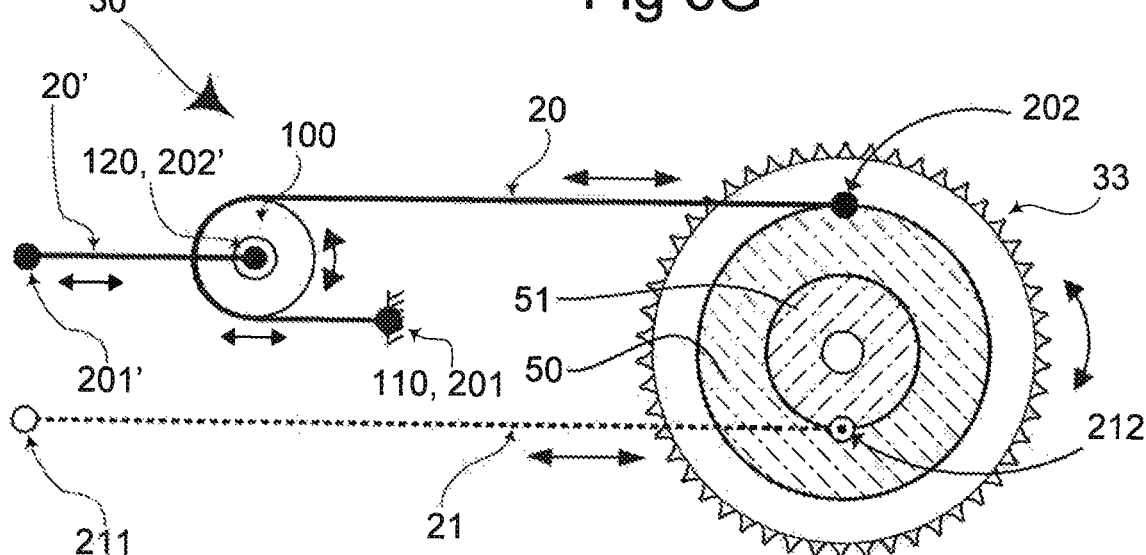
Figure 3M:
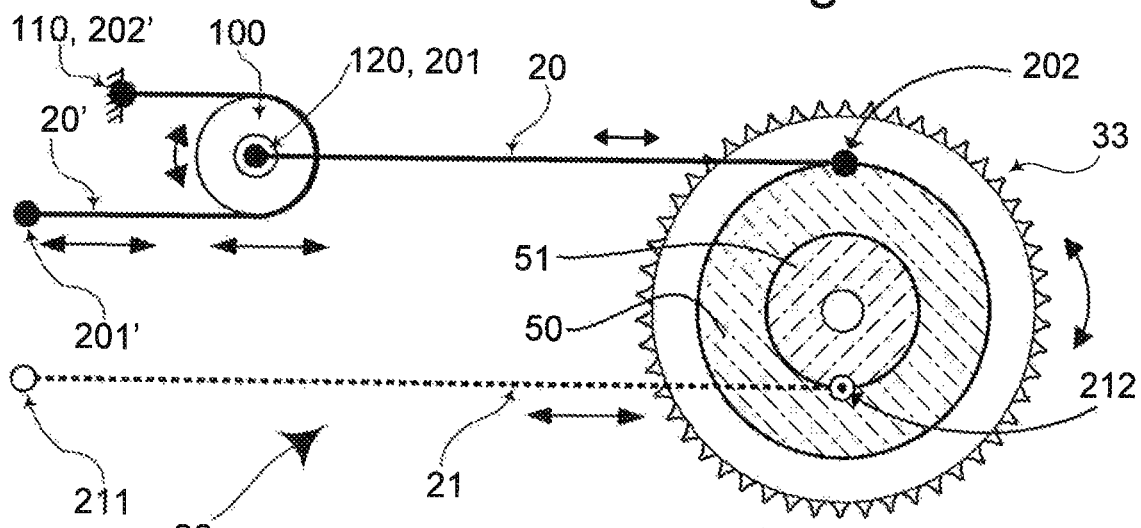
Figure 3H:
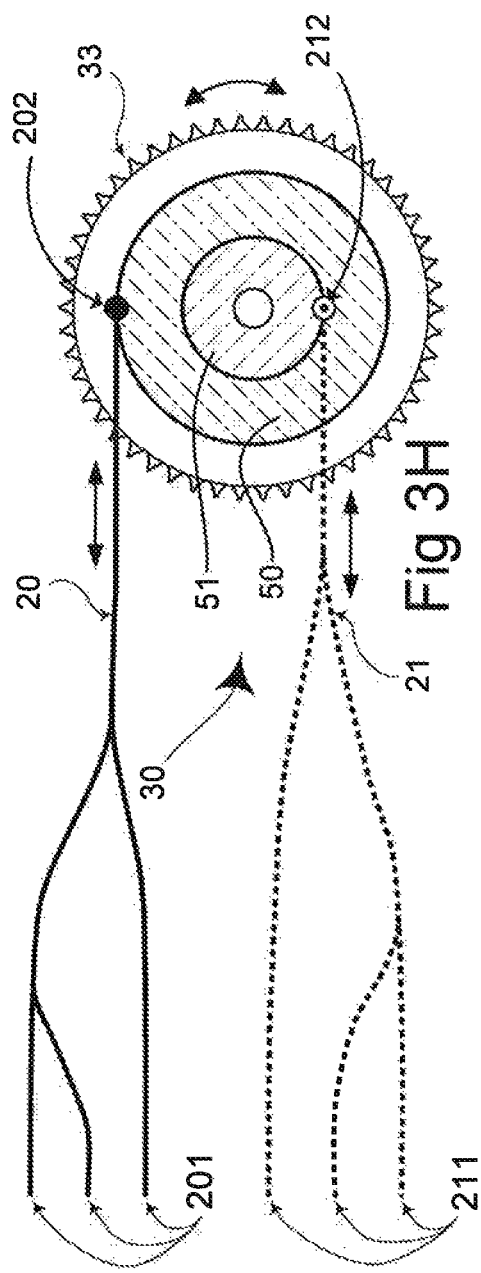
Figure 3I:
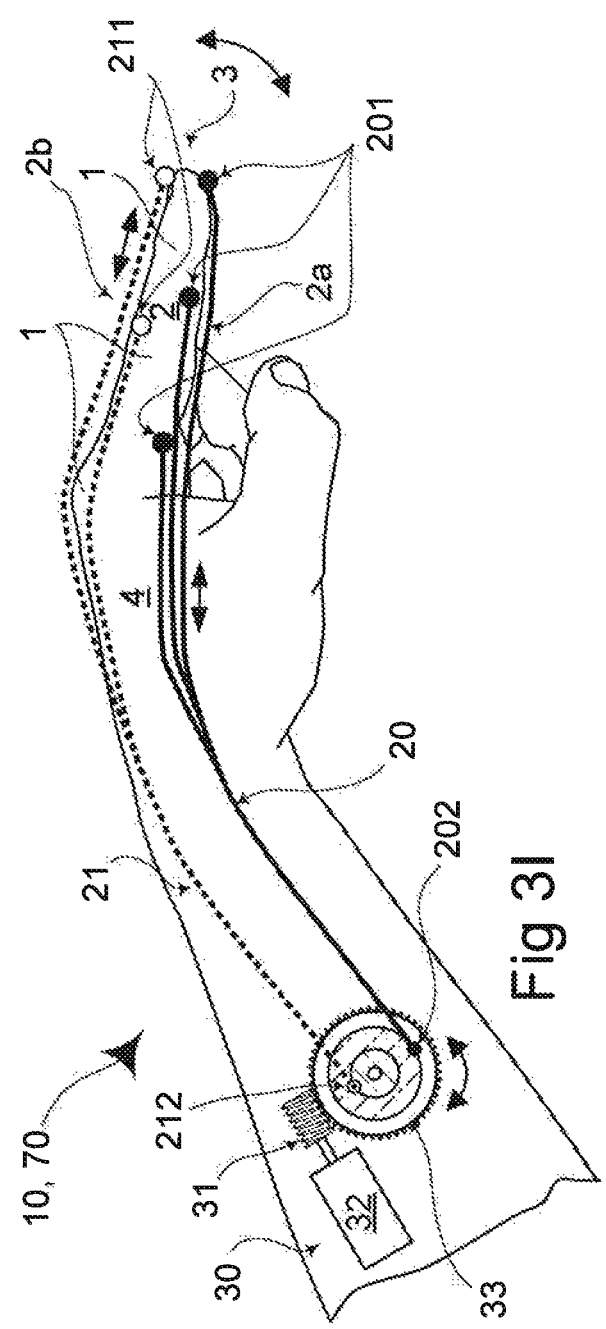

In FIGS. 2A, 2B, 3B, 3D, 3I, and 3K, aspects of the device 10 comprises one or more driving mechanisms 30 which in turn comprises at least one or more self-inhibiting or self-locking gears 31 driven by power means 32, preferably an electrical motor 32, which motor is a linearly or rotationally working motor. In FIGS. 2A, 2B, 3D, 3I and 3K, a device 10 with one driving mechanism 30 is shown. In FIG. 3B, a device 10 with two driving mechanisms 30 is shown. Hence, in many aspects, the technical solutions are sketched placed on worm wheel 33 but it does not have to be a worm gear, it could be some other drive means/wheels/pulleys 50, 51 and/or arms 60, 61. In FIGS. 3J and 3K, a device 10 with one driving mechanism 30 comprising three first tendons 20 attached to one pulley 50, 51 and/or arm 60, 61 and two second tendons 21 attached to another pulley and/or arm is shown. Here, the tendons 20, 21 could be attached to one associated pulley 50, 51 and/or arm 60, 61 individually or in any other combination, e.g. two first tendons 20 could be attached to one pulley 50 and/or arm 60 and/or the third first tendon 20 to another pulley 51 and/or arm 61. In FIGS. 3H and 3I, a device 10 with one driving mechanism 30 comprising one first tendon 20 attached to one large pulley 50 and one second tendon 21 attached to another/small pulley 51 is shown. Here, the tendons 20, 21 could be attached to one common pulley 50, 51 with sections of different or almost the same size/diameter d, d', D, D' and/or arm 60, 61 or in any other combination, e.g. the first tendon 20 could be individually attached to one separate pulley 50 and/or arm 60 of same size as the pulley 51 and/or arm 61 to which the second tendon 21 is attached.

FIGS. 3L and 3M show two aspects of the invention, where one or more of the first tendons 20 are not directly attached to any limb/finger 2 via its first end 201 but through at least one transmission by being winded around for example at least one block and tackle/tally system 100 with a center point/axis 120, and extending to a fix or fixed attachment or point or anchor/anvil 110 to which at least one or more first ends 201 of at least one first tendon 20 is anchored instead of being directly anchored to one or more limbs/fingers 2. The same structure and tackle arrangement could be used for the second tendon 21 at the same time or instead but this version is not shown in FIG. 3L. Here, a second part/section 20' working as a prolongation of the first tendon 20 is attached with a second end 202' to the centre axis/point 120 of the tackle 100 and attached with its first end 201' directly to one or more limbs/fingers 2 as a lengthening piece together with the tackle system 100, 110, 120 between the limb/finger and the second end 202 of the first tendon 20. In FIG. 3M, one or more first tendons 20 is instead attached to the centre axis/point 120 of at least one tackle system 100, 120 with its first end 201 and its prolonging part 20' is attached with its second end 202' to the fix/fixed attachment/point/anvil 110 and winded around the tackle 100 and attached with its first end 201' to one or more limbs/fingers 2 as a lengthening piece together with the tackle system 100, 110, 120 between the limb/finger and the second end 202 of the first tendon 20. The same structure and tackle arrangement could be used for the second tendon 21 at the same time or instead but this version is not shown in FIG. 3M.

According to another aspect, at least one tendon 20' is not directly attached to the driving mechanism 30 but to at least one or more tackle systems 100, 120 there between comprising at least one, i.e. is not limited to one tackle and a fix/fixed/static attachment end/point 110. According to yet one aspect, at least one tendon 20' is not directly attached to any driving mechanism 30 but via e.g. one or more tackle systems 100, 120 comprising at least one tackle 100 and fix or fixed or static attachment end/point 110, to increase or decrease pulling force between one or more tendons 20' attached to the distal end 3 and one or more tendons 20, 21 directly attached with their second ends 202, 212 to one or more associated driving mechanisms 30. Hence, the first tendon 20 could be made-up of two tendon parts, i.e. the first tendon part 20 itself and the additional prolonging first tendon part 20', and/or the second tendon 21 could be made-up of two tendon parts, i.e. the second tendon part 21 itself and an extra prolonging second tendon part similar to the prolonging first tendon part 20'. Each tackle system 100, 120 is part of the actuation function provided by driving mechanism 30 as any tackle system affects operation and transferred force/torque and size of movements between associated entities of this system and mechanism.

In FIG. 7, an aspect of the driving mechanism 30 comprises a planetary gearing that in turn comprises a sun gear 34, a ring gear 35, a planet gear carrier 36, and a planet gear 37. Using a planetary gear between the first pulley 50 and the second pulley 51 enables providing the pulleys with almost equal or equal diameter.

In most aspects of the driving mechanism 30, it comprises an outer casing 38 to enclose all components as a dust/dirt protection (see FIGS. 6, 8A to 8C, 9 to 11, 14A, 14B, 15A, 15B, 17A, 17B, 18A, 18B, 20A, 20B, 22A, 22B, 23A, 23B, 24A and 24B) together with a bottom plate 381, upper plate 382, and middle plate 383. In the other figures, this outer casing 38 is left out for clarity reasons. The middle plate or housing 383 functions as an intermediary sealing, holding and stabilisation part for the device 10 as it comprises several parts making up different sections or modules I to V (see FIGS. 14A and 14B), which modules are detachably connected together to make up the device and the modules I to V are also replaceable by any other module.

In FIGS. 5A to 5F, there are shown different aspects of the biasing mechanism/organ 40 of the driving mechanism 30 of which one or more may be applied to a user, i.e. the wearer in need of one or more such helping devices 10.

In FIG. 5A, the biasing mechanism/organ 40 is in the form of a spiral/watch/clock/motor spring with one end 41 connected to a pulley 50, 51 and/or rotary arm 60, 61 and the other end 42 connected to the gear/driving wheel 33. This spring 40 is double-acting, i.e. active in both directions of rotation, and its spring characteristics is variable/can be optionally chosen to fit application and individual/personal needs of the user, i.e. the wearer of the device 10.

In FIG. 5B, the biasing mechanism/organ 40 is in the form of a coil/helical/helicoidal spring with one end 41 connected to a pulley 50, 51 or rotary arm 60, 61 and the other end 42 connected to the gear/driving wheel 33. This spring 40 is bent/curved to fit into the casing 38 and could be stretched or relaxed and compressed and/or be double-acting and its spring characteristics is variable/can be optionally chosen to fit application and individual/personal needs of user, i.e. wearer of device 10.

Figure 5C:
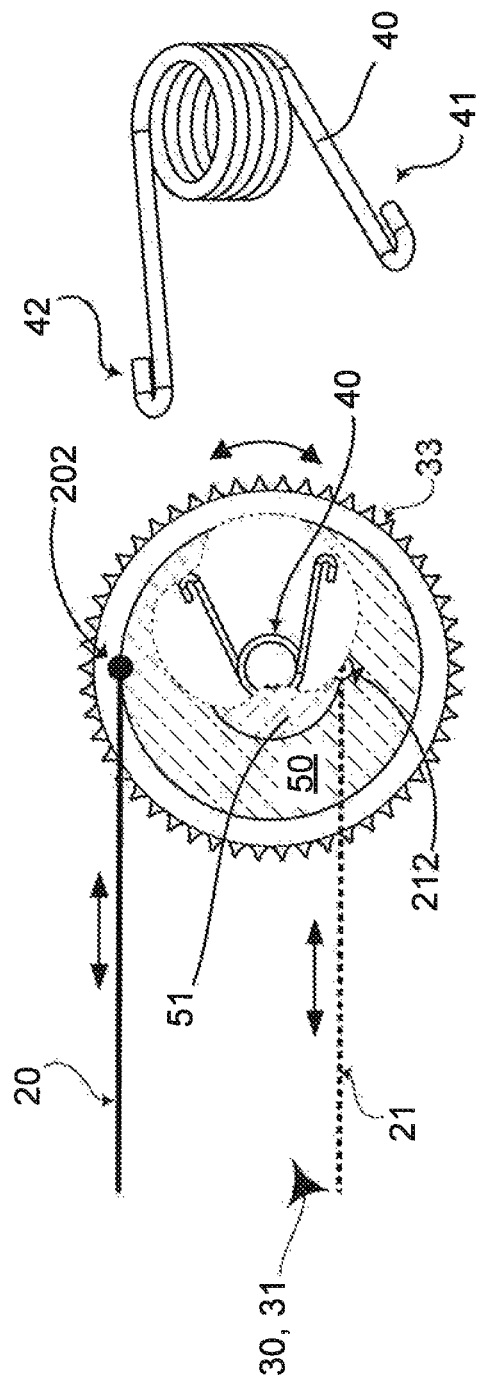

In FIG. 5C, the biasing mechanism/organ 40 is in the form of a torsion spring with one end 41 connected to a pulley 50, 51 or rotary arm 60, 61 and the other end 42 connected to gear or driving wheel 33. This spring 40 is fitted around a centre axis of the gear wheel 33 and is also double-acting, i.e. active in both directions of rotation, and its spring characteristics is variable/can be optionally chosen to fit application and individual/personal needs of the user/wearer of device 10.

Figure 5D:
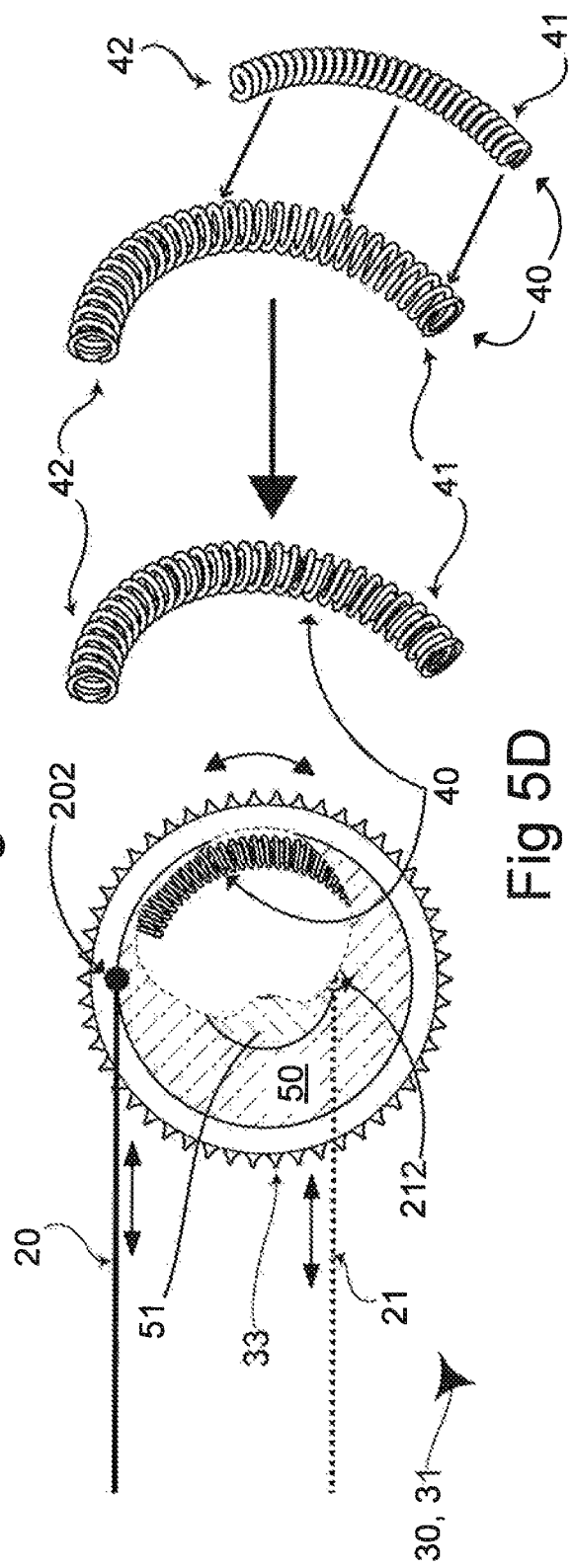

In FIG. 5D, the biasing mechanism/organ 40 is similar to the aspect of FIG. 5B but in the form of at least two coil/helical/helicoidal springs of which one is larger than the other, and the smaller one adapted to be introduced into the larger spring to adapt or vary the spring characteristics of a double spring that can be optionally chosen to fit application. The springs 40 are connected with one end 41 to a pulley 50, 51 or rotary arm 60, 61 and the other end 42 to the gear/driving wheel 33. This double-spring 40 is also bent/curved to fit into the casing 38 may be stretched/relaxed and compressed accordingly and/or be double-acting, and its spring characteristics is variable/can be optionally chosen to fit application and individual/personal needs of the user/wearer of device 10.

Figure 5E:
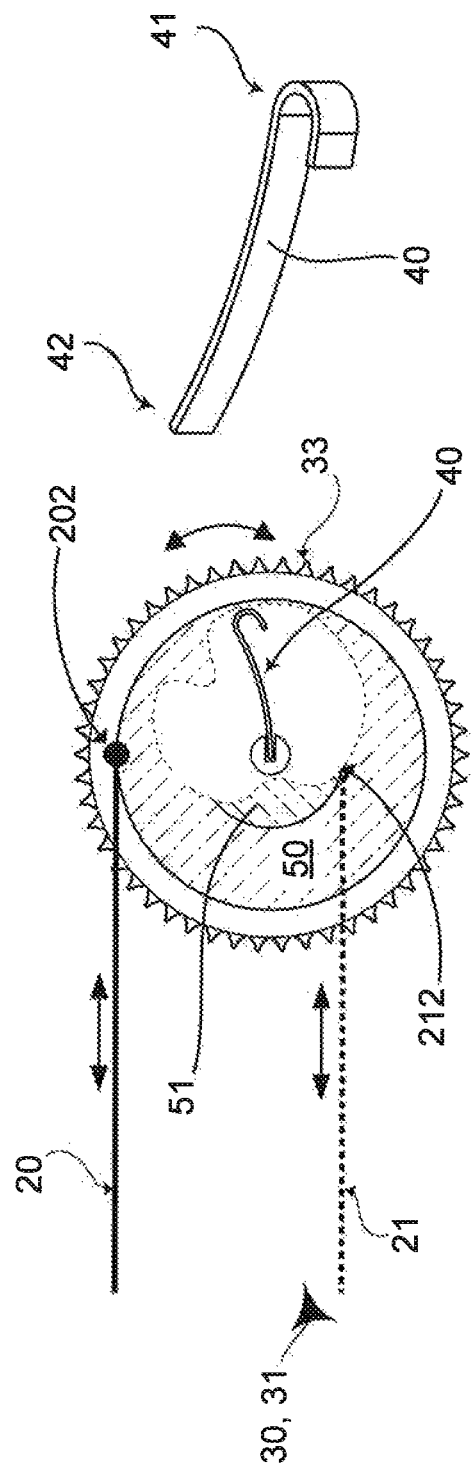

In FIG. 5E, the biasing mechanism/organ 40 is in the form of a plate/leaf/ribbed/laminated type/leaf spring with one end 41 connected to a pulley 50, 51 and/or rotary arm 60, 61 and the other end 42 connected to the gear/driving wheel 33.

This spring 40 is also double-acting, i.e. active in both directions of rotation, and its spring characteristics is variable/can be optionally chosen to fit application and individual/personal needs of the user, i.e. the wearer of the device 10, but is commonly stiffer compared to the above spring aspects.

Figure 5F:
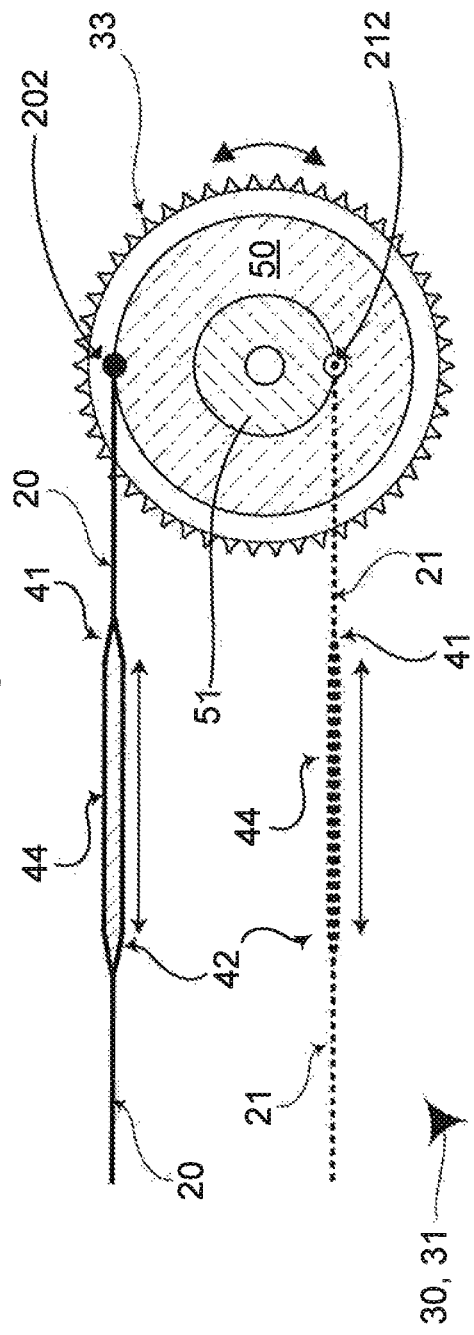

In FIG. 5F, there is shown a separate biasing member 44 in the form of a separate and/or integrated elastic or resilient or springy biasing member separately arranged at one or more of the tendons 20, 21 whereby at least a part of or the whole of the respective tendons 20, 21 is made elastic or resilient or springy or stretchable up to a maximum length or extension of the separate biasing member 44. The elasticity may alternatively or additionally be integrated in one or more of the pulleys 50, 51, in the nature of at least one spring operatively arranged between one or more of the pulleys and one or more of the tendons 20, 21. The elasticity exerts a weak force on the respective tendon, which is only sufficient for eliminating and reducing slack, which may arise in the tendon. Thus, the weak force of each separated biasing member 44 is much smaller than the pulling force generated by the biasing mechanism/organ 40. This weak force may be between ten times and hundred times smaller than the pulling force. Thus, when a pulling force is exerted on a tendon, the separate biasing member is first extended to its maximum length and then the pulling force starts to pull the tendon. At the same time, a separate biasing member 44 of another tendon may contract by said weak force to eliminate and reduce any slack of said another tendon.

In FIGS. 5A to 5F, the shown aspects of the biasing organ 40 has the main advantage that torque and/or force is not transmitted directly from the driving wheel 33 to any pulley 50, 51 and/or rotary arm 60, 61, instead it is buffered/stored in a spring function enabling dynamic movement between pulley/arm and the transmission of the driving mechanism 30.

FIGS. 6A and 6B show aspects of the driving mechanism 30 in perspective and partly cross-sectioned for clarity reasons for better understanding of the engagement between the gears.

In FIG. 8A, an aspect of the driving mechanism 30 is shown in cross-section comprising one common pulley with pulley sections 50, 51 of different diameters that enable contraction and extension of one or more fingers 2 and/or pivoting about one or more joints 1 independently of the motor 32 when not operated. Here, one common biasing organ 40 for the pulley 50, 51 is used, i.e. one biasing organ 40 between worm wheel 33 and pulley with both the first/larger pulley 50 and the second/smaller pulley 51 integrated into one for transfer of torque/force between the pulley 50, 51 and the worm wheel 33.

In FIG. 8B, an aspect of the driving mechanism 30 is shown in cross-section comprising pulleys 50, 51 that enable contraction and extension of one or more fingers 2 and/or pivoting about one or more joints 1 independently of each other and the motor 32 by using one or more biasing organ 40 for each pulley 50, 51, e.g. one biasing organ 40 between the worm wheel 33 and the first/larger pulley 50 and one biasing organ 40 between the worm wheel 33 and the second/smaller pulley 51, for separate transfer of torque/force between each of the pulleys 50, 51 and the worm wheel 33. In FIG. 8B, two biasing organs 40 are used acting in opposite directions for biasing the two interconnected pulleys 50, 51.

In FIG. 8C, an aspect of driving mechanism 30 is shown in cross-section comprising two pulleys 50, 51 that enable contraction and extension of one or more fingers 2 and/or pivoting about one or more joints 1 simultaneously of each other and motor 32 by use of a biasing organ 40 transferring torque/force between one of the pulleys and the worm wheel 33. Both pulleys 50, 51 are adapted to move together (as in FIG. 8B) but with a gear change/changing between one pulley and the gear 31. Biasing organ 40 causes the mutual and directly coupled movement to be different than the driving gear 31. Here, a planetary gear is arranged between the pulleys and makes it possible to use pulleys of almost the same or the same diameter.

In FIGS. 9 to 11, aspects of driving mechanism 30 are shown. FIG. 9 shows in perspective and exploded view an aspect of an arrangement of sensors 80, 81 for defining positions and speeds of motor 32 and pulleys 50, 51 and/or rotary arms 60, 61 to enable a possibility of calculating the extraction/retraction of an artificial tendon 20, 21 (or several artificial tendons), and/or the position of at least one or several or all of the fingers 2/joints 1 (or any other limb, artificial or human). If the motor 32 already has a built-in sensor/feedback system, such as for a brushless electric motor, only one additional set of sensors is required to be able to measure the rotation of any pulley 50, 51 and/or arm 60, 61 for positioning. Moreover, if the characteristic of the biasing organ or spring 40 is known it is also easy to calculate the exerted force from and/or strain in a tendon 20, 21, which could give us, e.g. the clamping force of a hand's grip. Here, two sensors, e.g. optical encoders 80, 81 are used. One sensor 80 is arranged on a pulley 50 or 51 and one sensor 81 is arranged on the motor axis (or worm gear 33) of motor 32. The device 10 could even be used for machines to get a safe, small and energy saving system. Advantages of the sensor positioning in the device 10 are that it is easy to calculate position of fingers/arms 2 due to non-elastic tendons 20, 21 and optical encoders 80, 81, e.g. easy to calculate force in tendons 20, 21 and also the grip of a hand around an object as the tension of the biasing organ 40 and thereby the force of any tendon is easily calculated as the angular difference between any pulley 50, 51 and/or rotary arm 60, 61 and self-inhibiting gear 31, and by knowing this the position of any arm/limb/finger/-s can easily be calculated with known spring characteristics of biasing organ 40, safer usage and product due to the spring which gives an elastic flexibility to the device 10, provides a longer battery life due to the self-locking worm gear transmission, and creates more natural movement of fingers/arms/limbs 2 due to this in the device 10 inherent spring-like and energy storing effect.

In FIGS. 2A, 2B, 3B, 3D, 3I, 3K, 6A, 6B, 8A-11, 12A-12E, and 12G, the one or more self-inhibiting gears are disclosed as a worm gear or worm gear unit or worm reduction gear 30 driven by the rotary electrical motor 32 to pivot/rotate at least one pulley 50, 51 and/or rotary arm 60, 61.

Figure 12A:
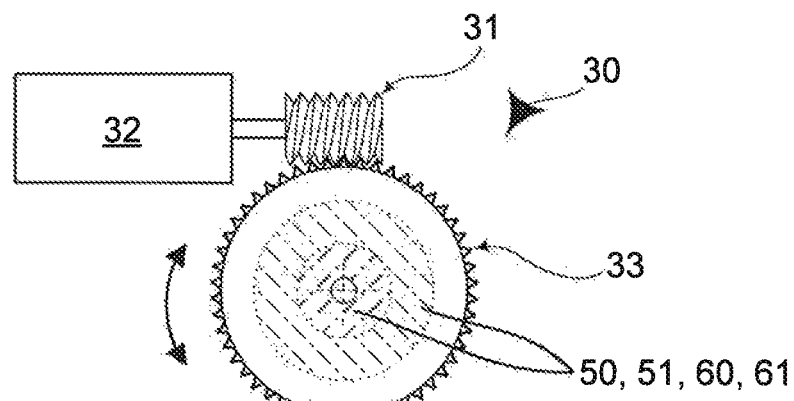
Figure 12B:
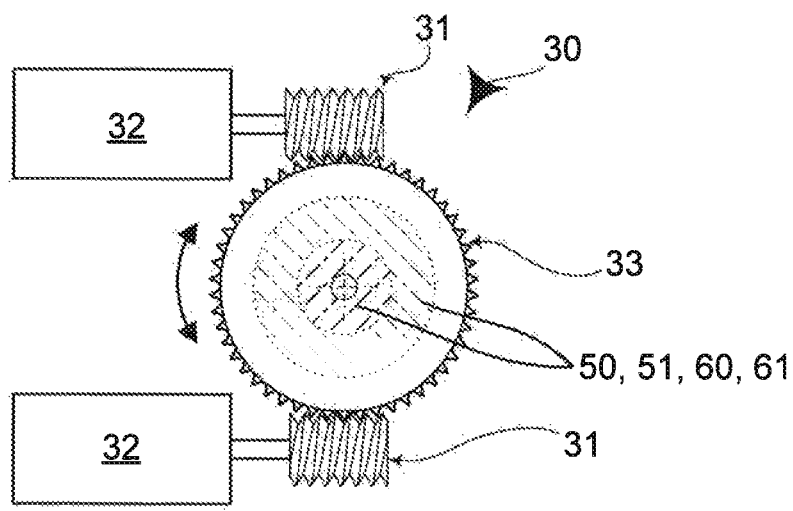
Figure 12C:
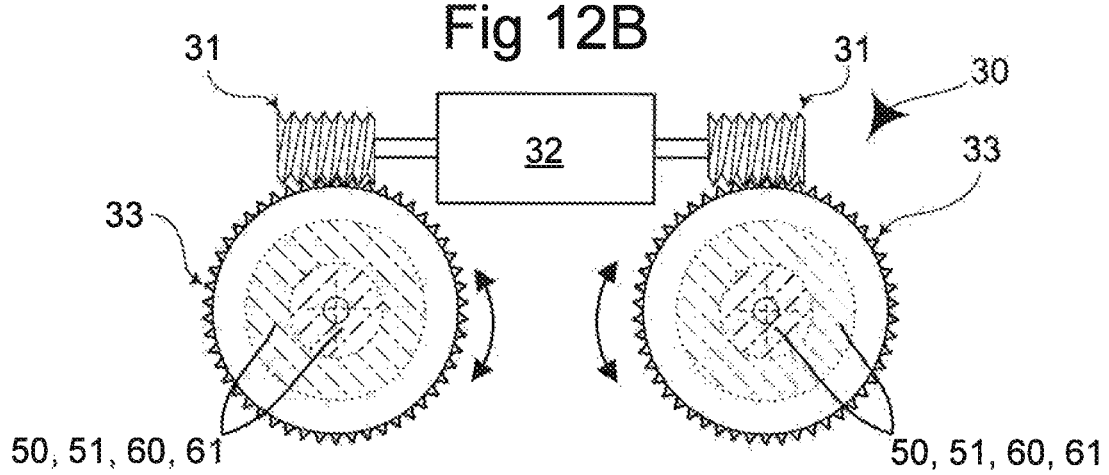
Figure 12D:
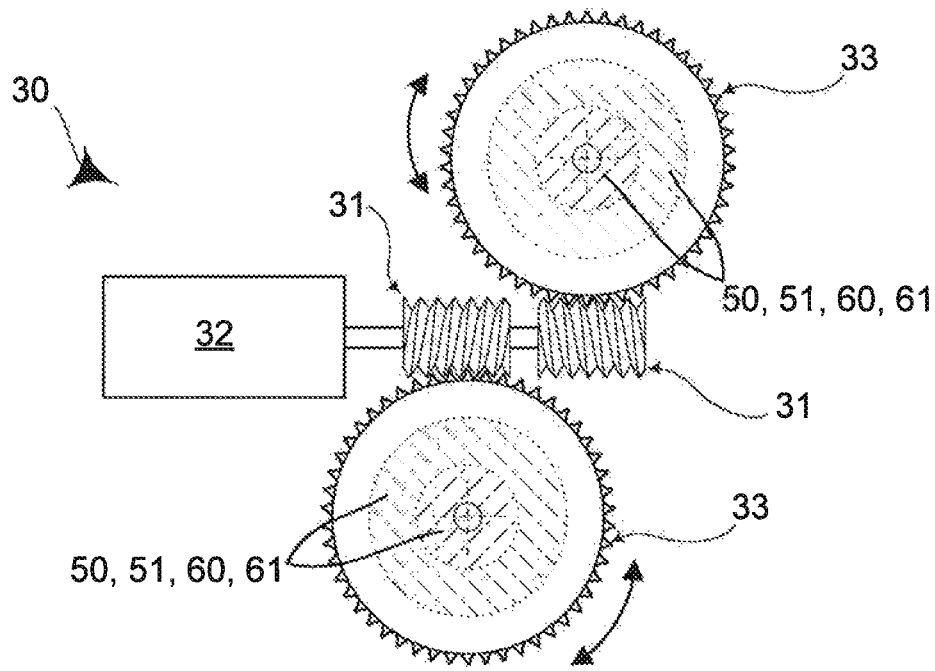
Figure 12E:
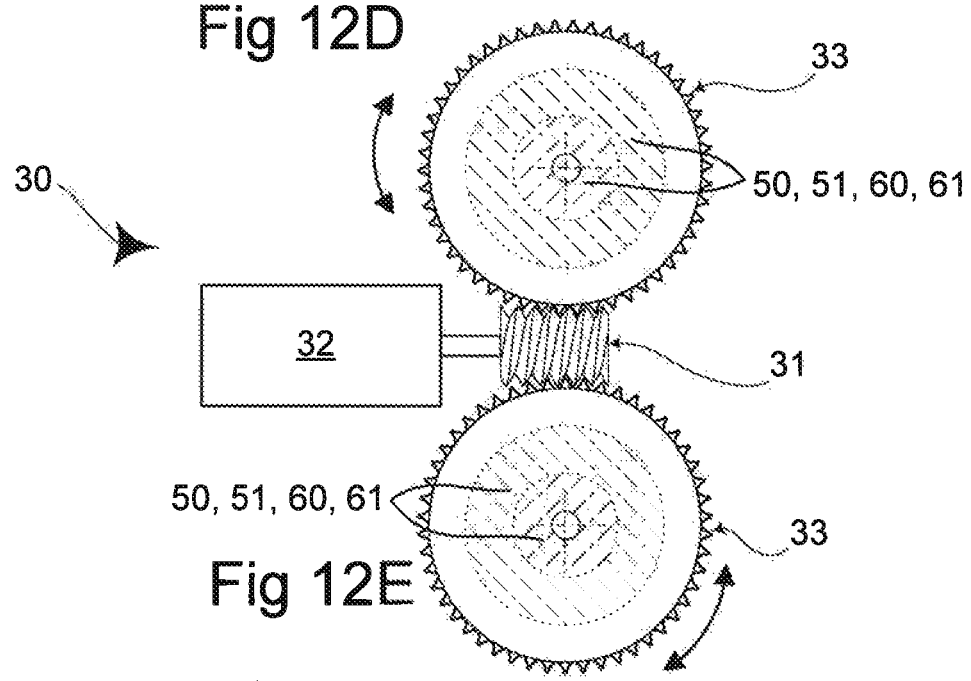
Figure 12F:
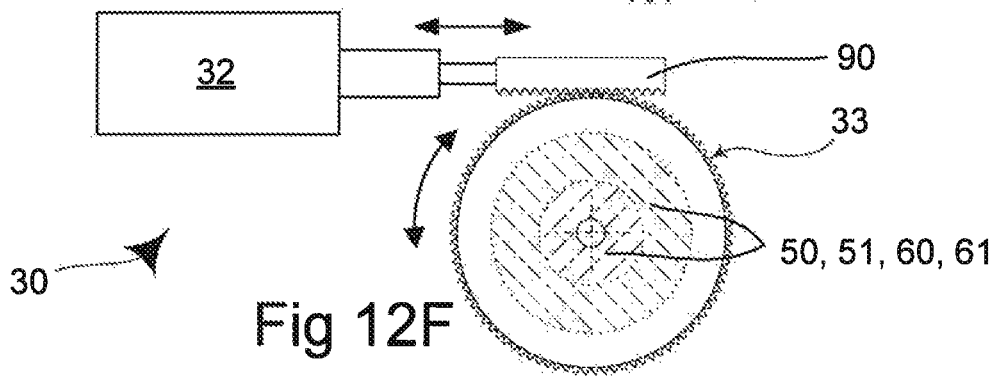

In FIGS. 12A to 12I, the different pulleys/arms 50, 51, 60, 61 are shown with dot and dash lines for visualization. In FIG. 12F, the self-inhibiting gear 31 is disclosed as a back and forth axially movable rack unit driven by a linear electrical motor 32 to pivot/rotate at least one pulley 50, 51 and/or rotary arm 60, 61.

Figure 12G:
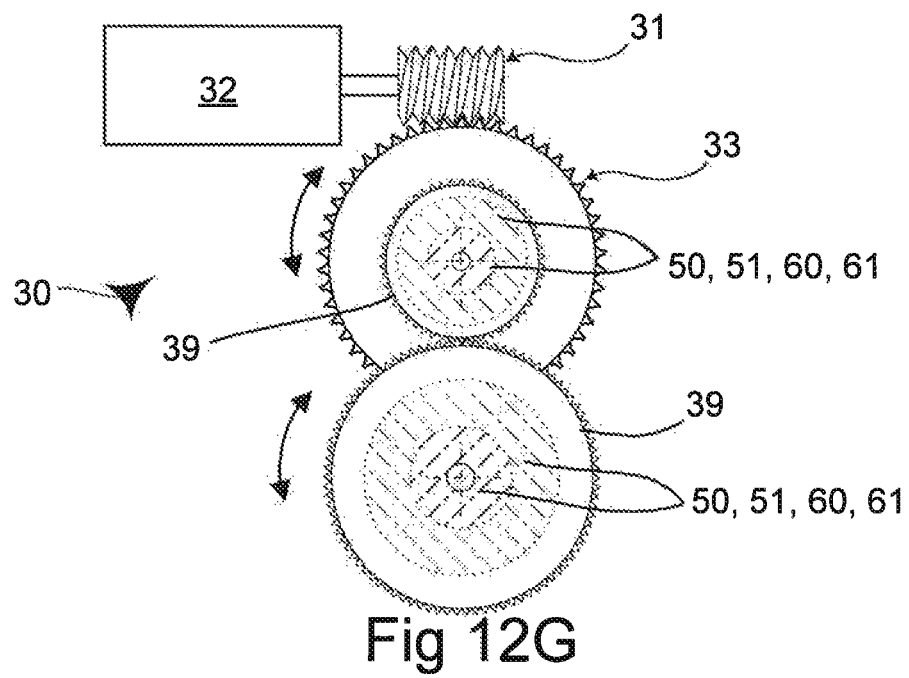

In FIG. 12G, this aspect of the driving mechanism 30 comprises one or more additional gear wheels 39 besides the worm wheel 33. Here, this aspect provides more or less gear change/changing by use of ordinary gear wheels in dependence to application and individual/personal needs of the user, i.e. the wearer of the device 10.

Figure 12H:
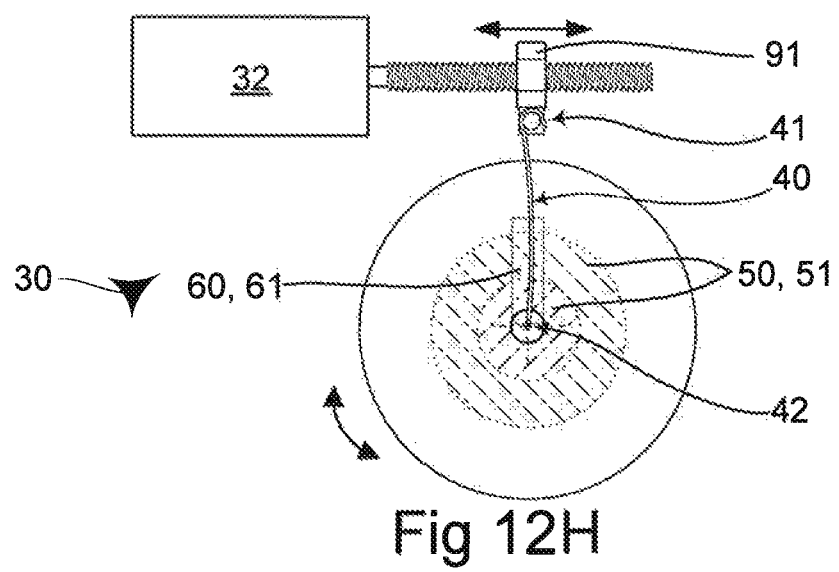

In FIG. 12H, the self-inhibiting gear 31 is disclosed as a nut 91 hindered for rotational movement, so that the nut 91 only is able to be moved linearly back and forth by means of a screw rotating within it by being driven by a rotary electrical motor 32 to pivot or rotate at least one pulley 50, 51 and/or at least one rotary arm 60, 61 via the first end 41 of one type of a bias/biasing mechanism/organ 40 to the other end 42 of the bias organ 40 forcing the at least one pulley 50, 51 and/or at least one rotary arm 60, 61 (shown in a dashed line in FIG. 12H) to pivot/rotate. Here, the bias organ 40 is a leaf spring connected to the nut 91 at one end 41 and the winding mechanism with pulleys and/or rotary arms at the other end 42.

Figure 12I:
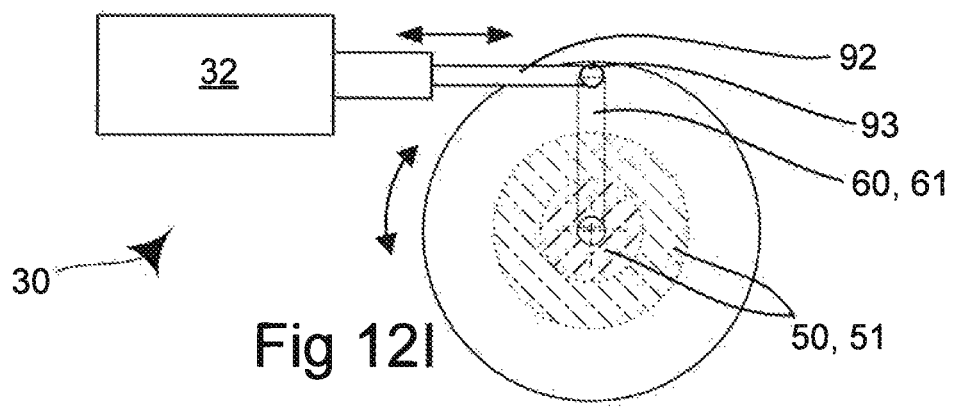

In FIG. 12I, the self-inhibiting gear 31 is disclosed as a piston-like unit 92 driven by a linear electrical motor 32 at one end to pivot or rotate at least one pulley 50, 51 and/or at least one rotary arm 60, 61 by means of another end being rotationally/pivotally connected via a joint 93 to the pulley 50, 51 and/or the rotary arm 60, 61 shown with a dashed line in FIG. 12I.

In FIGS. 12J and 12K, the driving mechanism 30 of the device 10 is shown in two different aspects of using a linearly working drive motor 32 operatively connected to one longer rotary arm 60 and one shorter rotary arm 61 via the biasing member 40. The biasing member 40 is arranged within a casing 43 with its first end 41 operatively connected to one end of a piston-like unit 92 within the casing and with its second end 42 fixedly/stationary connected against the inside of the casing 43 working as an anvil/anchor during operation and extension and compression of the biasing organ 40 being a coil or helical or helicoidal spring. The linear drive motor 32 is connected to a first end of the biasing member casing 43, whereby the motor 32 move the whole casing 43 and the spring 40 together with the piston 92 and the arms 60, 61 when operated. Hence, this enables, when the motor 32 is not operated, the casing 43 to be held/kept still, i.e. maintained in one stationary position by the motor being self-inhibiting, and the piston 92 to be movable by means of the arms 60, 61 when the arm/finger 2 is moved in any direction.

This means that the spring 40 also is adapted to be extended if the piston 92 moves axially to the left in FIGS. 12J and 12K by being pushed by the arms 60, 61 rotating/pivoting about a stationary joint or axis 94 clockwise in FIGS. 12J and 12K. The piston 92 is rotary/pivotally connected via a joint 93 to the longer rotary arm 60 and/or the shorter rotary arm 61. In FIG. 12J, the arms 60 and 61 are fixedly connected at the static joint or axis 94 as one arm, however the arms may be firstly manufactured as separate entities and finally fixedly attached to each other via the static joint 94. In FIG. 12K, the arms 60 and 61 are formed/manufactured as one fixed arm pivotally/rotatably connected to the static joint or axis 94. In FIG. 12J, the upper view discloses one position of the drive mechanism 30, e.g. a neutral position of an arm or finger 2. The lower view of FIG. 12J shows movement of piston 92 to the right or left for pivoting/rotating the arms 60, 61 counter-clockwise or clockwise, respectively, and thereby moving the arm/finger 2 from or to the gesture or position shown in the upper view of FIG. 12J independently if the motor 32 is driven or not.

In FIGS. 12J and 12K, this means, if the electrical motor 32 moves casing 43 with the spring 40, the piston 92 is also moved, and if the motor 32 is not operated, i.e. stands still, and the arm 60 and/or arm 61 is moved by pulling and/or slacking tendons 20, 21 via manual movement of the arm/finger 2 by the human, tendons 20, 21 pull and slack and moves its associated arm 60 or 61 accordingly without moving the casing 43, i.e. only the spring 40 is expanded or compressed within the casing 43 in response to the moving arms. In FIG. 12K the piston 92 and the tendon 20 shares the same rotary point 94. In FIGS. 12J and 12K, sensor 83 measures if the distance to the piston 92 changes, whereby the force induced and/or relaxed of the spring 40 and the position of one or more limbs/arms/fingers 2 are easily calculated as the spring characteristics are known/predetermined.

The motor 32 could, instead of being electrical, be hydraulically, pneumatically, piezo-electrically, and/or thermally driven. Moreover, more than one motor 32 may be applicable for each device 10. In FIGS. 2A, 2B, 3A to 3F, 4, and 5A to 5F showing different aspects of the diameters d, d', D, D' of the pulleys 50, 51 and the length of the arms 60, 61, the difference in size between smaller and larger pulleys and longer and shorter arms could as an example be thrice or twice or more or less. Hence, the larger pulley 50 has a diameter D, D' being three times the diameter d, d' of the smaller pulley 51, i.e. D or D'=3×(d or d'). The same goes for the arms 60, 61, i.e. the long arm 60 is as examples three or two times or even longer than the short arm 61. Hence, the tendon shown in FIGS. 1B, 2B, 17B and 26 which is to extend for example the finger 2 moves a shorter distance than an opposing tendon which would contract the finger, whereby the pulleys and/or arms have different diameters and lengths, respectively, if they rotate/pivot with the same speed. In one aspect or example, when the device 10 is applied for a hand 4, e.g. at least the forefinger/index finger 2, the second tendon 21 along the dorsal side 2b of the forefinger 2 moves or is pulled/drawn out about 10-20 mm, e.g. about 17 mm (of course depending on the size of the hand 4 and/or length of the finger 2, e.g. if a child or adult is provided with the device), during contraction of the forefinger (see FIGS. 1B and 2B), while the first tendon 20 along the opposite side or underside 2a of the forefinger 2 is moved/retracted/pulled/drawn in about 40-70 mm, e.g. about 55 mm.

In FIG. 13, the device 10 and driving mechanism 30 is schematically shown together with other components as a flowchart visualising feedback and build-up of a system and method of operation of the device 10. Here, the device comprises the control unit 70 and the different controllers 72, 74, 75, 76, the various sensors 80, 81, 82 operatively connected to the control unit, the controllers, driving mechanism 30, motor 32 and the pulleys/arms 50, 51, 60, 61 such that the alternate rolling in/pulling and movement following/rolling out/slacking of the tendons 20, 21 and the operation of the device 10 and driving mechanism 30 are regulated in response to sensor output given from the tension of the biasing member 40 and thereby the force of the tendon 20, 21 which together with the position of the arm/limb/finger/-s gives the control system its desired error signal.

In a first aspect of the invention, the device 10 for pivoting at least one arm 2 relative to at least one joint 1 comprises at least one artificial tendon 20, 21 attached to a proximal end 3 of the arm and a driving mechanism 30, the driving mechanism being connected to and adapted to pull the tendon and thereby the proximal end of the arm to make it pivot, and is characterized in that the device 10 further comprises a first tendon 20 movably extending along at least a first side 2a of the arm 2 and attached with a first end 201 to the proximal arm end 3, and at least a second tendon 21 movably extending along at least one second side 2b of the arm 2 and attached with a first end 211 to the proximal arm end 3, wherein the driving mechanism 30 is adapted to pull the first tendon 20 and to simultaneously slack the second tendon 21 to extend the arm 2 and to pull the second tendon and to simultaneously slack the first tendon to retract the arm when operated, and that the device 10 further comprises at least one biasing organ 40 operatively connected to the driving mechanism 30 and the tendons 20, 21 as an intermediary part to enable pulling and slacking of the tendons without operating the driving mechanism. In a second aspect of the invention, the device 10 according to the first aspect comprises the driving mechanism 30 that comprises a self-inhibiting gear 31 operatively connected between the biasing organ 40 and the driving mechanism and adapted to transmit movement from the driving mechanism to the biasing organ and further to the tendons 20, 21 when the driving mechanism is operated while hindering movement of the biasing organ incurred by pull and/or relaxation/slack in the tendons to be transmitted to the driving mechanism when the driving mechanism is not operated. In a third aspect of the invention, in the device 10 according to any of the preceding aspects, the biasing organ 40 is elastic or resilient or a springy member and/or at least one tendon 20, 21 is elastic or resilient or springy or stretchable. In a fourth aspect of the invention, in the device 10 according to any preceding aspect, the biasing organ 40 is at least one spring. In a fifth aspect of the invention, in the device 10 according to the fourth aspect, the biasing organ 40 is at least one of: a spiral/watch spring, coil/helical/helicoidal spring, a plate/leaf/ribbed spring, a laminated type/leaf spring, a spring blade, and/or a torsion spring. In a sixth aspect of the invention, in the device 10 according to any preceding aspect, the driving mechanism 30 comprises at least one pulley 50, 51 to which a second end 202, 212 of each tendon 20, 21 is attached. In a seventh aspect of the invention, in the device 10 according to any preceding aspect, the driving mechanism 30 comprises at least one rotary arm 60, 61 to which a second end 202, 212 of each tendon 20, 21 is attached. In an eight aspect of the invention, in the device 10 according to the sixth aspect, the driving mechanism 30 comprises at least two pulleys 50, 51 of different sizes/diameter to which the second ends 202, 212 of the tendons 20, 21 are attached individually. In a ninth aspect of the invention, in the device 10 according to the seventh aspect, the driving mechanism 30 comprises at least two rotary arms 60, 61 of different lengths having a first end 601, 611 attached to the biasing organ 40 and a second end 602, 612 attached to an associated second end 202, 212 of a corresponding tendon 20, 21. In a tenth aspect of the invention, in the device 10 according to the eight aspect, the driving mechanism comprises one pulley 50 with a size/diameter D, D' larger than the size/diameter d, d' of the other pulley 51, whereby the larger pulley 50 is operatively connected to the second end 202 of the first tendon 20 and the smaller pulley 51 is operatively connected to the second end 212 of the second tendon 21. In an eleventh aspect of the invention, in the device 10 according to the ninth aspect, one rotary arm 61 has a shorter length than the other rotary arm 60, whereby the shorter arm 61 is operatively connected with its first end 611 to the second end 212 of the second tendon 21 and the longer arm 60 is operatively connected with its first end 601 to the second end 202 of the first tendon 20. In a twelfth aspect of the invention, the device 10 according to any of the preceding aspects is operated by means of a method comprising steps of arranging at least one body member/arm/finger 2, 4 with the device 10 at a suitable position in relation to an object to be handled; moving the body member 2, 4 into physical contact with the object to be handled; detecting the movement of the body member 2, 4 by measuring a corresponding movement of at least one tendon 20, 21 of the device 10; operating the driving mechanism 30, 70 of the device 10 in a first direction to bias the body member 2, 4 into firmer physical contact with the object until desired contact force is reached; stopping the operation of the driving mechanism 30, 70 when the desired contact force is reached; maintaining the correct contact force between object and the body member 2, 4 by means of a self-inhibiting functionality of the driving mechanism 30, 31, 70; operating the driving mechanism 30, 70 in a second direction to reduce the bias of the body member 2, 4 to zero and until the physical contact with the object has disappeared; arranging the device 10 and the at least one body member 2, 4 at another or the same suitable position in relation to another or the same object to be handled. In a thirteenth aspect of the invention, the method according to the twelfth aspect comprises a further step of detecting the movement of the at least one body member 2, 4 by measuring corresponding alternate movement of at least two tendons 20, 21 and/or at least two split ends of one or more of the tendons of the device 10. In a fourteenth aspect of the invention, the method according to the twelfth or thirteenth aspect comprises a further step of detecting the movement of the body member 2, 4 by using signals and measuring to control bi-directional movement of at least two tendons 20, 21 of the device 10 by pulling one tendon while slacking another tendon in response to desired handling of the object. In a fifteenth aspect of the invention, the method according to any of the twelfth to fourteenth aspect comprises a further step of operating the driving mechanism 30, 70 of the device 10 in the first direction to dynamically bias the body member 2, 4 by preloading a biasing organ 40 increasing pulling force in at least one tendon 20, 21 until the desired contact force with the object is reached. In a sixteenth aspect of the invention, the method according to any of the twelfth to fifteenth aspect comprises a further step of operating the driving mechanism 30, 70 of the device 10 in the second direction to dynamically reduce the bias of the body member 2, 4 by unloading/relaxing a biasing organ 40 decreasing pulling force in at least one tendon 20, 21 until the desired contact force with the object is zero and until there is no physical contact between the device, body member and the object. In a seventeenth aspect of the invention, the method according to any of the twelfth to sixteenth aspect comprises a further step of maintaining the correct contact force between object and body member by means of the self-inhibiting functionality of the driving mechanism 30, 31, 32, 70 keeping the driving mechanism immobile, operating an actuation device 20, 21 comprising at least a first artificial tendon 20, a distal end 201 of which is attached to a distal portion 3 of the body member 2, 4 and extending in a first path along the body member beyond a joint 1 and a proximal end 202 of which is attached to the driving device 30; which actuation device 20, 21 comprises at least a second artificial tendon 21, a distal end 211 of which is attached to said distal portion 3 of the body member 2, 4 and extending along a second path of the body member beyond said joint 1 and a proximal end 212 of which is attached to the driving device 30 independently of the driving device by pulling said first artificial tendon 20 and simultaneously slacking said second artificial tendon 21 for generating a torque in a first direction around said joint 1, and pulling said second artificial tendon 21 and simultaneously slacking said first artificial tendon 20 for generating a torque in a second direction around said joint 1 manually; and simultaneously and dynamically reducing or increasing a bias of the body member by unloading/relaxing or loading/biasing a biasing organ 40 being arranged between said motor 32 and said driving device 30 for decreasing or increasing pulling force in at least one tendon 20, 21.

Figure 14A:
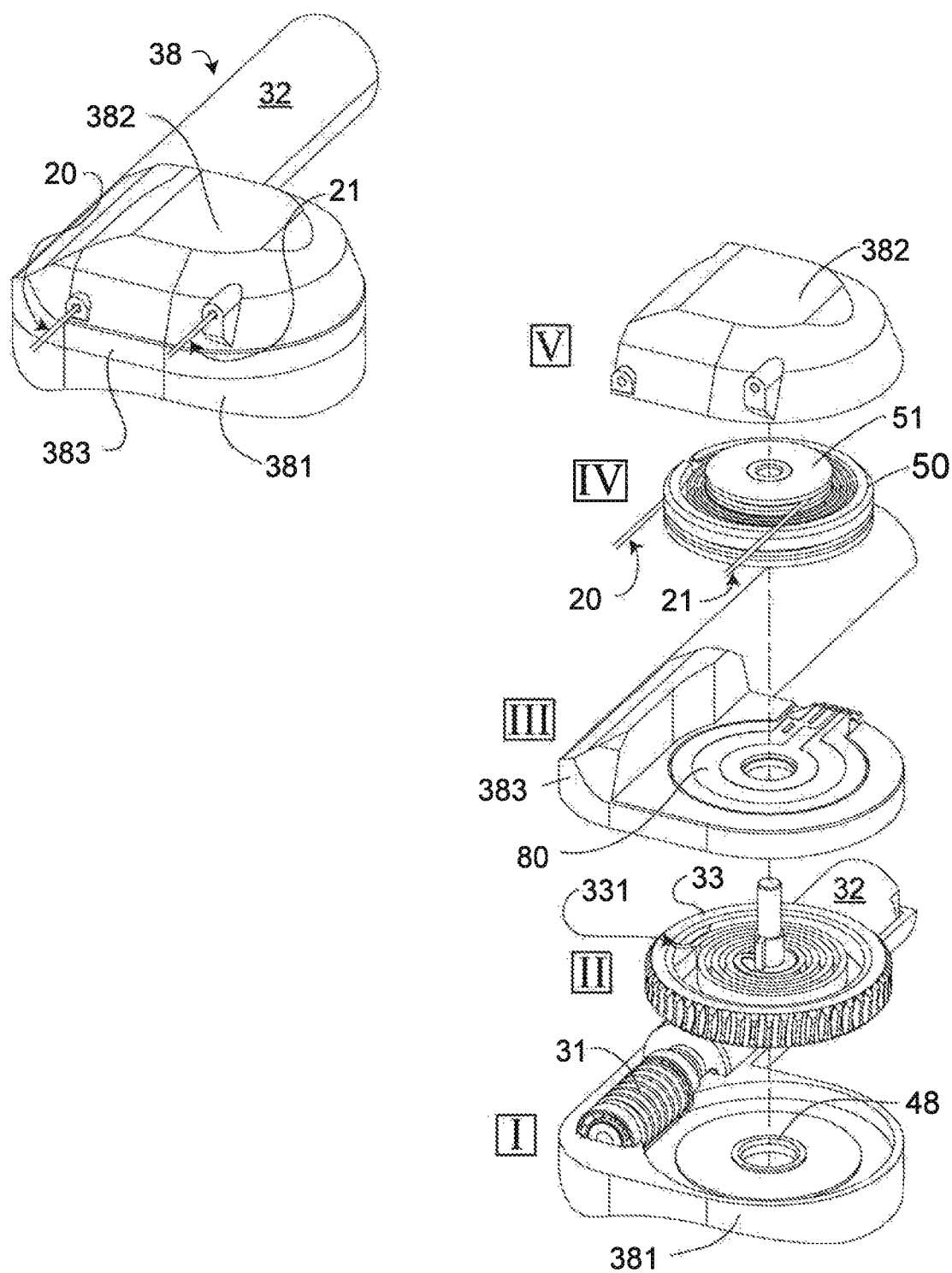
Figure 14B:
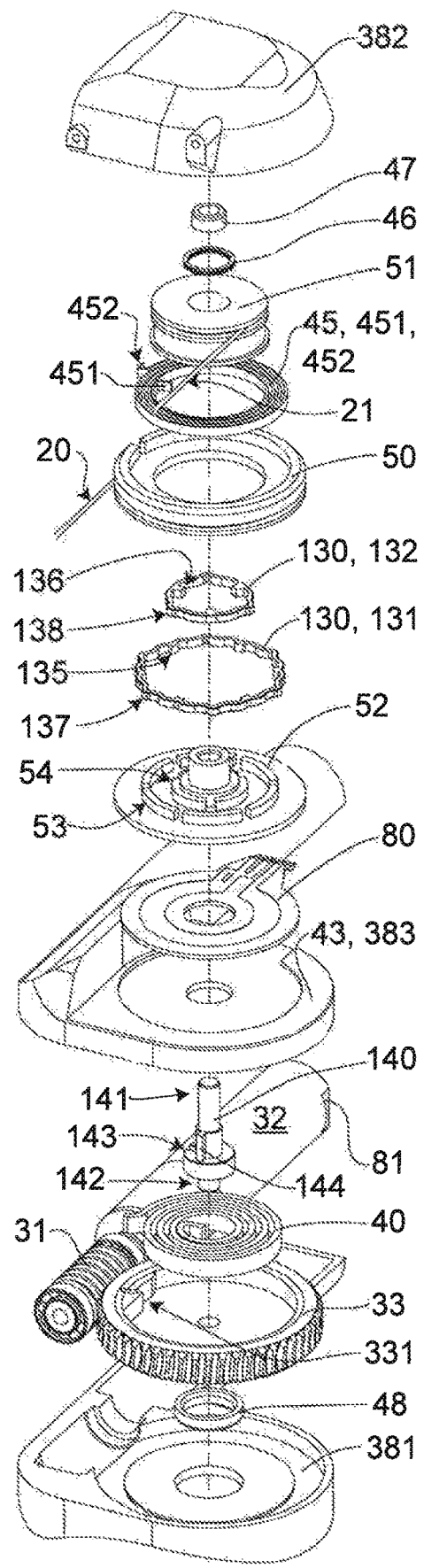

The device 10 is shown on FIGS. 14A and 14B with all of its features, i.e. modules I, II, III, IV and V as a full system, where the modules comprises corresponding parts as above and additional ones combined with additional functionalities for further improvement of the ability and user friendliness of the device 10 and simplified maintenance and repair. The device 10 is shown in FIGS. 15A to 26 in different embodiments in regard of different combinations of functions and/or the modules I to V and views including both sectional, perspective and plan ones to better visualise these associated functionalities and for better understanding of the below detailed explanation of all these versions of the device 10 and its modules I to V. All of the above and herein explained aspects or embodiments or examples of the device 10 could comprise one, two, three or four, i.e. all of the above and below modules I to V and/or their functionalities and could comprise any of these modules I to V with its functionalities, e.g. module I, in any combination with one or more or all of the other modules II to V in different configurations of the device 10.

Figure 16:
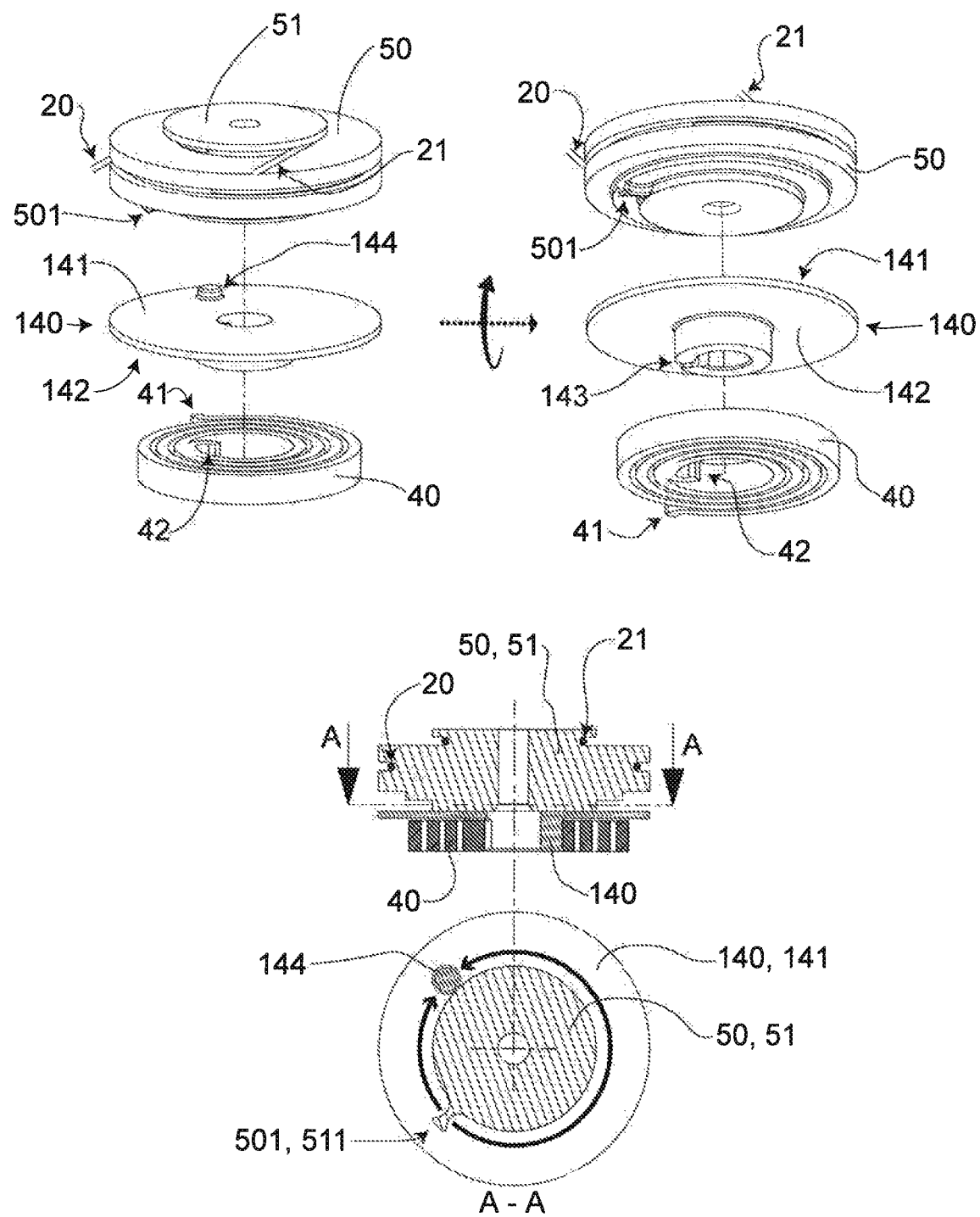
FIG. 16 shows several views of yet another aspect of the device according to the invention with similar features as in FIG. 15 but with modules II and IV in another embodiment with modules I, III and V excluded for clarity and shown in perspective slightly from above in the upper left view and in perspective slightly from below in the upper right view and from above and the side in section along line A-A.
Figure 17A:
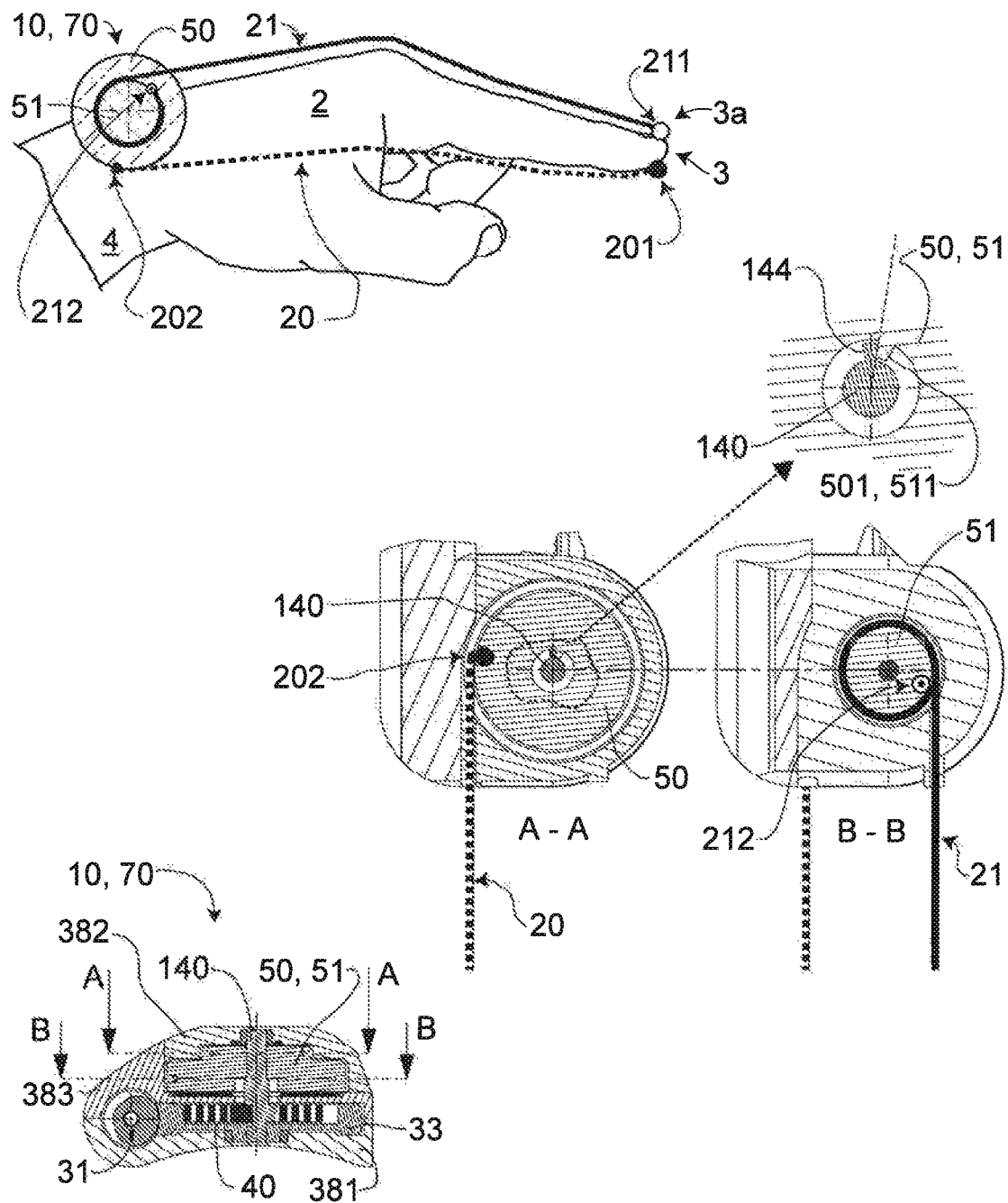
FIGS. 17A and 17B show several views of the device in FIGS. 15A and 15B to clarify its functionality and cooperation of modules II and IV, where a hand/body member is shown in two different postures.
Figure 17B:
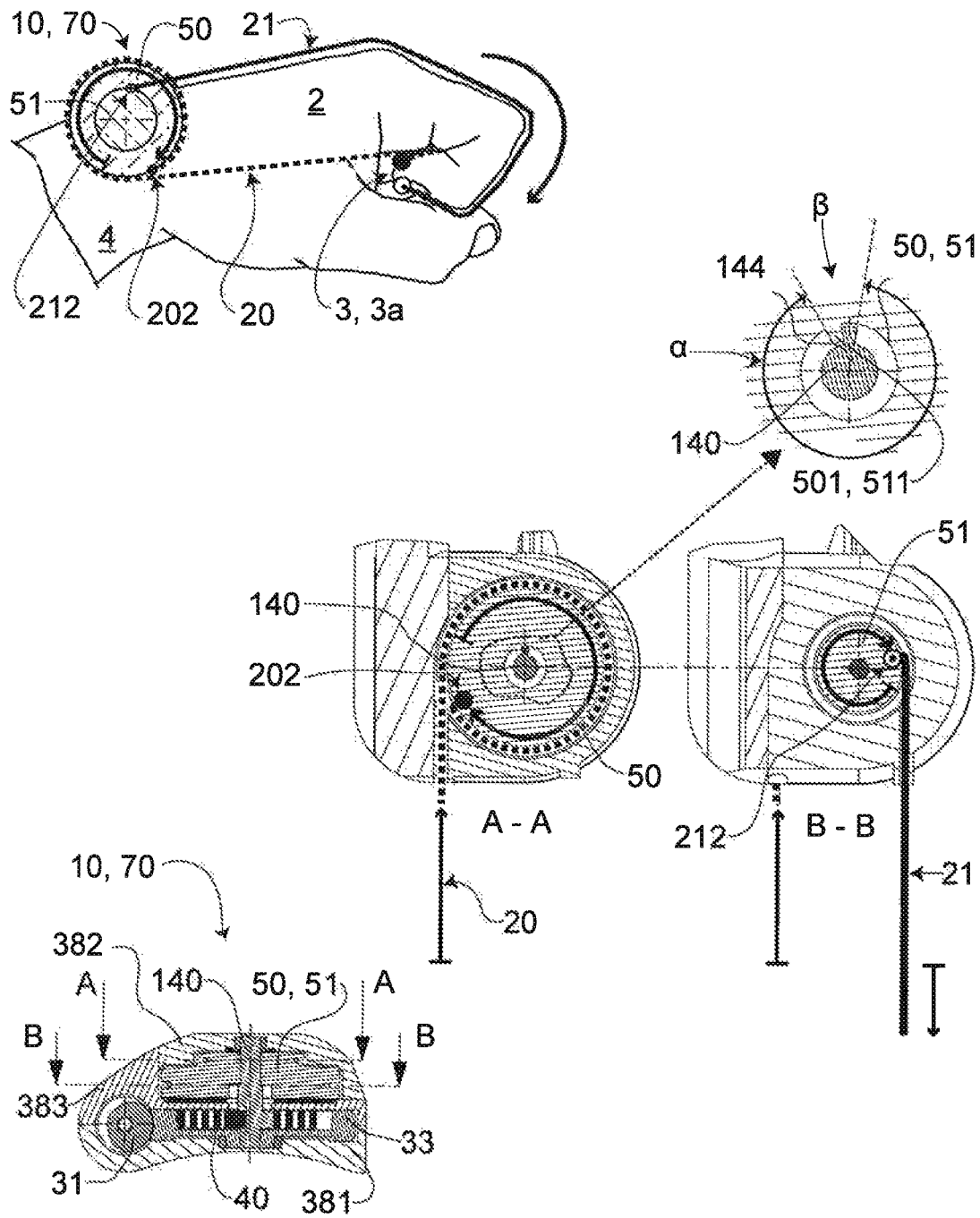

In FIGS. 14A and 14B, the device 10 is shown having all of the above modules I to V. Module I comprises the bottom plate 381 of casing 38, the drive mechanism 30, the electric motor 32 and a bearing 48 for rotary movement. Module II comprises the worm wheel 33 and the biasing member 40, which worm wheel 33 comprises a slot 331 at its inside for engagement with the outer end 41 of the biasing member 40. This module II comprises in some aspects/embodiments, as shown in FIGS. 14A, 14B, 15A, 15B, 16, 17A, 17B, 22A, 22B, 23A and 23B, a free wheel member 140. This free wheel member 140 is in one embodiment an axle as shown in FIGS. 14A, 14A, 14B, 15A, 15B, 17A, 17B, 22A, 22B, 23A and 23B, and in another embodiment a plate as shown in FIG. 16. This free wheel member 140 comprises a first end 141 for connection to the pulleys 50, 51 or rotary arms 60, 61 (not shown in FIGS. 14A to 26) and a second end 142 for connection to the inner end 42 of the biasing member 40. The second end 142 of the free wheel member 140 is provided with a slot 143 into which the inner biasing member end 42 is fitted without any play, at least not more play than the dimensional tolerances for these entities allow (see FIGS. 15A, 15B, 16 and 17A, 17B). Between the second end 142 and the first end 141 of the free wheel member 140 is a protrusion 144 arranged (see FIGS. 15A, 15B, 16 and 17A, 17B). The protrusion 144 is positioned at a middle portion of the free wheel member 140 in FIGS. 14A, 14B, 14C, 15A, 15B, 17A, 17B, 22A, 22B, 23A, and 23B, but could in other embodiments be placed closer to or further away from any of the free wheel member ends 141, 142, e.g. even at or adjacent or on the first end 141 or close to it. This free wheel member protrusion 144 has the purpose of allowing play between the biasing member 40 and the pulleys 50, 51 or rotary arms 60, 61, i.e. at least one of the pulleys 50, 51 or rotary arms 60, 61 are provided with a projection 501, 511 (see FIGS. 15A, 15B and 16) that is arranged to engage the free wheel member protrusion 144 in only two positions, i.e. not to engage it constantly as done by the free wheel member slot 143 and the biasing member 40 when assembled together. Hence, as shown in FIGS. 16 and 17A, 17B, the projection 501, 511 of the pulley 50, 51 and the free wheel member protrusion 144 are arranged/placed/positioned after assembly, such that a rotation of the pulley 50, 51 enables moving its projection 501, 511 from one angular position to another angular position without engaging the biasing member 40, i.e. without resistance from the biasing member (only friction must be overcome). This none-resisted movement is possible to perform until the pulley projection 501, 511 has reached or done a full swing between the two positions corresponding to an angle α that is shown as a length of an arc in FIGS. 17A and 17B. Another angle β in FIGS. 17A and 17B visualises the limitation/boundary for the movement as the projection 501, 511 and protrusion 144 need to have a minimum of physical space for accommodation. When the first or second artificial tendon 20, 20', 21 is pulled the pulley 50, 51 and its projection 501, 511 or rotary arm is moved freely without engaging the biasing member 40 until a certain size or distance or length or degree of the movement is reached. This size or distance corresponding to angle α in FIGS. 17A and 17B or a linear distance if performed in the device shown on FIGS. 12J and 12K. When this free wheel movement has reached the other end position and pulley projection 501, 511 engages the free wheel member projection 144, the free wheel member 140 is engaged and initiates a movement if the force from the pulley projection 501, 511 exceeds the mass moment of inertia of the free wheel member 140 and starts moving the free wheel member via its protrusion 144 and also the inner end 42 of the biasing member 40 via the slot 143 of the free wheel member, whereby a larger resistance from the biasing member 40 takes effect. The resistance/biasing from the biasing member 40 could be adapted to give differently sized resistances, i.e. larger or smaller resistance depending on the features of the biasing member 40 and in dependence to needs of the user of the device 10. The size of the free wheel movement is adapted to correspond to a full retraction as in FIG. 17B and full extension of an arm or finger 2 as shown in FIG. 17A. Module III comprises the middle plate 383 of the outer casing 38 and an angle/rotation sensor 80 in the form of a potentiometer being laminated or membrane-shaped. This module III is the same for all aspects/embodiments of the device 10. Module IV forms the actuation device comprising the tendon operating parts comprised of the pulleys 50, 51 and the attachment points for the second ends 202, 212 of the tendons 20, 21, which module IV has different functionalities/configurations, e.g. the pulleys 50, 51 being permanently rotatably locked or only rotationally locked together when assembled to the device 10, i.e. when the module IV is detached or disassembled from the device 10, the pulleys 50, 51 are rotatable in relation to each other, at least to some extent, enabling length adjustability of the tendons, and in another version of the module IV it comprises a torque limiting functionality, whereby, if any tendon 20, 21 is too heavily or quickly pulled by an external force or the motor 32 goes berserk risking damaging the device 10 and/or the user of the device, e.g. a finger 2 or the like, each pulley 50, 51 affected by this hard pulling tendon or "nutty" motor 32 is disengaged due to the torque limiting effect and the motor 32 is able to rotate freely, except for friction and resistance, without rotating the pulley. Module V is the same for all aspects/embodiments of the device 10 and comprises only the upper plate 382 of casing 38 being easily detachable from the device as the bottom plate 381 and middle plate 383.

Figure 21A:
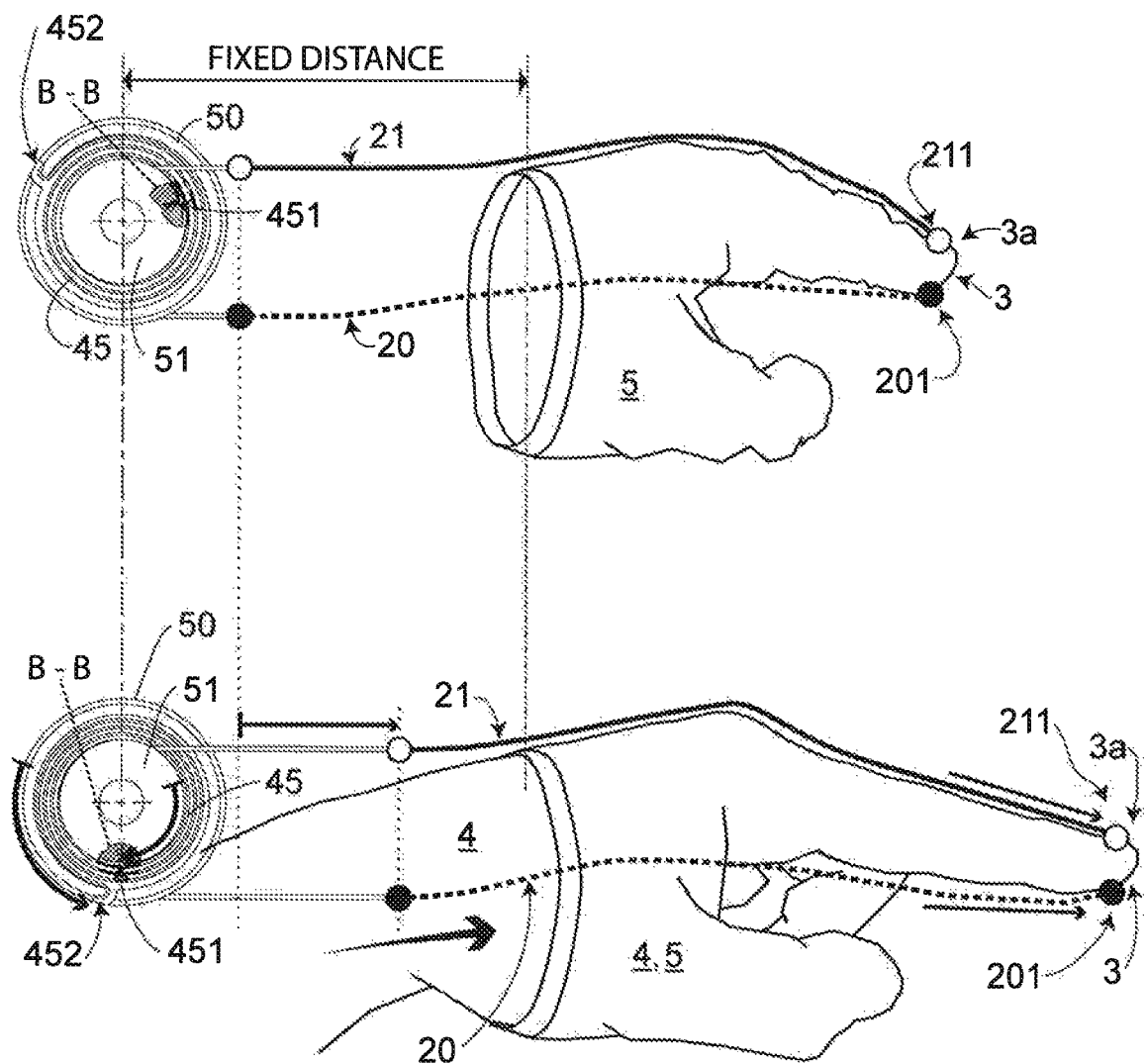
FIGS. 21A and 21B show several views of a detachable part of the device in FIGS. 20A and 20B applied to a glove, i.e. a module IV being detached from other modules I, II, III and V making up the whole device.
Figure 21B:
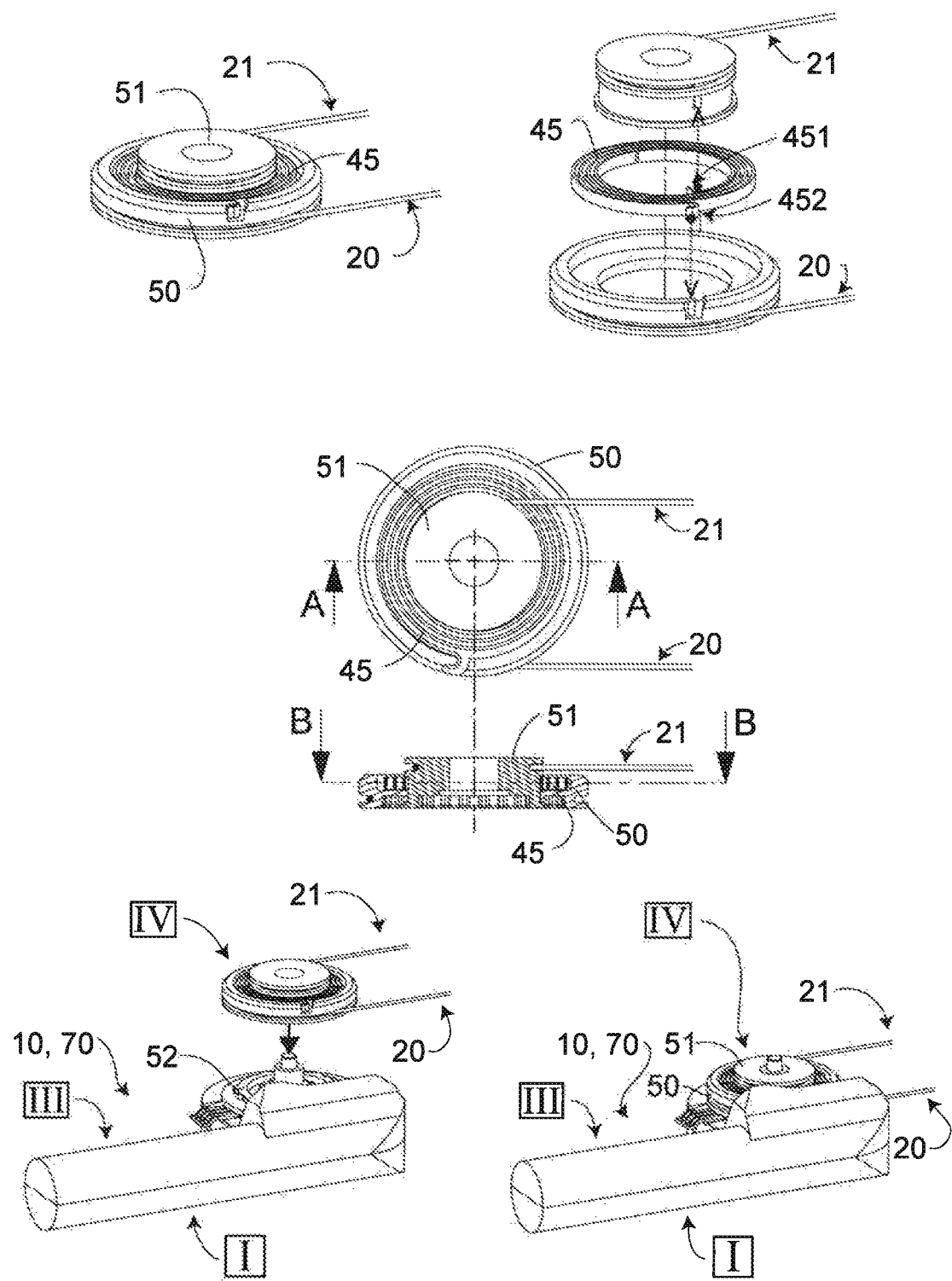

In FIGS. 14A and 14B, the device 10 is shown with all its modules I to V and their functionalities and the drive mechanism 30 where the motor 32 (with or without a possible first gearbox) has a built in or external first angle/rotation sensor 81 and with its output shaft directly connected to the worm screw 31. The worm screw 31 is adapted for direct engagement with the worm wheel 33 after assembly. The worm wheel 33 is connected with its inner slot 331 at the inside of the worm wheel for engagement with the outer end 41 of the biasing member 40, i.e. to one side of the biasing member, which biasing member in these FIGS. is a torsion spring in the shape of a clock spring. The other end 41 or other side of the biasing member 40 is connected to the free wheel member 140, which can rotate around the same axis as the worm wheel 33. Here, the free wheel member 140 is an axle or axis shaft. The free wheel member 140 is adapted for connection to a pulley or spools core 52 but with a free wheel interval between the two parts, i.e. the free wheel movement giving the certain play of movement between them as explained above. This free wheel interval allows the pulley core 52 to rotate freely relative to the free wheel member 140 for the certain angle interval of a (e.g. about 320°), but at the end and the beginning of this interval the free wheel member 140 and the pulley core 52 are engaged by means of their protrusion 144 and projections 501, 511. The free wheel function makes it possible for the user to move the actuated finger/limb 2 unhindered for a certain interval/distance. Here, the angular position of the pulley core 52 is read by a second angle/rotation sensor 80. The pulley core 52 of module IV is connected to the two pulleys 50, 51, the large pulley 50 and the small pulley 51 through a kind of spline joints 53 that are adapted to in this embodiment to connect to one or more torque limiters 130. Here, two tendons 20, 21 are mounted, one each, to one of the two pulleys and winded up in opposite directions. Between the pulley core 52 and each of the pulleys 50, 51 there are separate torque limiting functions in the form of spline joints in module IV installed for the safety of the user and the device 10. Here, the spline joints are active parts of the device 10 as they work as torque limiters 130 for the pulleys 50, 51. This is done by use of a large splined deformation ring 131 being firmly mounted, i.e. non-rotatable but detachable, via a spline joint 135 to a large outer spline joint 53 of the pulley core 52 and comprising a flexible spline joint 137 against the large pulley 50 creating an automatic engaging and disengaging of the operation and drive between the large splined deformation ring 131 and the large pulley 50, and a small splined deformation ring 132 being firmly mounted, i.e. non-rotatable but detachable, via a spline joint 136 to a small inner spline joint 54 of the pulley core 52 and also comprising a flexible spline joint 138 against the small pulley 51 creating an automatic engaging and disengaging of the operation and drive between the small splined deformation ring 133 and the small pulley 51. If the tension in any of the tendons 20, 21 gets too high, so that it could damage the user or the device 10, the torque between the operating pulley (large pulley 50 or small pulley 51) and the pulley core 52 will reach above its allowed maximum. When this happens the associated splined deformation ring 131, 132, which is being stressed beyond its maximum (the large one 131 or the small one 132) will elastically deform and release its splined coupling 137, 138 that engage recesses 55, 56 in the associated pulley 50 and/or 51 and let it rotate until the torque drops beneath the allowed maximum and the splined couplings 137, 138 come into operative engagement with its associated pulley 50, 51. Another aspect/embodiment/example of the torque limiting functionality in module IV is shown in FIG. 19B where the coupling between the pulley core 52 and each pulley 50, 51 is provided by spring-biased balls 133 that engage recesses 55, 56 in the pulley and are placed in holes with a spring 134 in the pulley core 52, whereby the spring force is adapted to push each ball 133 with a certain force against/into the pulley recesses 55, 56, such that when any tendon 20, 21 or the motor 32 incur excessive force the balls 133 are moved out of engagement with the pulley recesses and provides a disengagement similar to the splined deformation rings 131, 132. The two pulleys 50, 51 are mounted together to prevent them from falling apart when not mounted on the pulley core 52, but with the possibility to rotate relative to each other about the same axis. Between the two pulleys 50, 51 is a pre-tensioned biasing member 45 installed with one inner end 451 connected to the small pulley 51 and the outer other end 452 connected to the large pulley 50, which pre-tensioned biasing member 45 works as an adjustment spring for the length of the tendons 20, 21. The inner end 451 of the adjustment spring 45 is connected to the small pulley 51 by being inserted into an opening of the pulley (see FIGS. 21A and 21B), this opening could be a slot but is here an elongated opening into which the inner end 451 snaps in. The outer other end 452 of the adjustment spring 45 is shaped with a bend that hooks over a rounded end on the large pulley 50 (see FIGS. 21A and 21B). Here, the length adjustment spring 45 is a torsion spring in the shape of a constant torque spring. When the pulley 50, 51 are mounted on the pulley core 52 the length adjustment spring 45 has no effect on the system, i.e. on the tendons 20, 21 as they then are rotatably locked together. However, when the two pulleys 50, 51 are detached and lifted from the pulley core 52 the length adjustment spring 45 with its pre-tension will force the pulleys to rotate with a relatively small torque in opposite directions and stretch/tension the tendons 20, 21 that runs out through a finger of a glove 5, if the device 10 is placed on a glove 5. Then, when a users hand is inserted into the glove, the length adjustment spring 45 will let the tendons 20, 21 be released for a bit at the same time as they are in a stretched condition until the glove 5 is properly fitted on the hand 4 and any finger 2. When the pulleys 50, 51 then are assembled/mounted back on the pulley core 52 the length adjustment spring 45 will again have no effect on the tendons 20, 21, but the glove 5 with its tendons 20, 21 will be correctly adjusted into a good fit for the user and be ready for use. Hence, the fixed distance in the upper view of FIG. 21A is fixed in the sense that it is adapted to different sizes of hands 4 and the full retraction and extension of the tendons 20, 21 for the glove fitting. The adjustment spring 45 urges the two pulleys 50 and 51 in two different, i.e. opposite rotational directions when the module IV is detached from the device 10 to "shrinken" the glove 5.

Figure 15A:
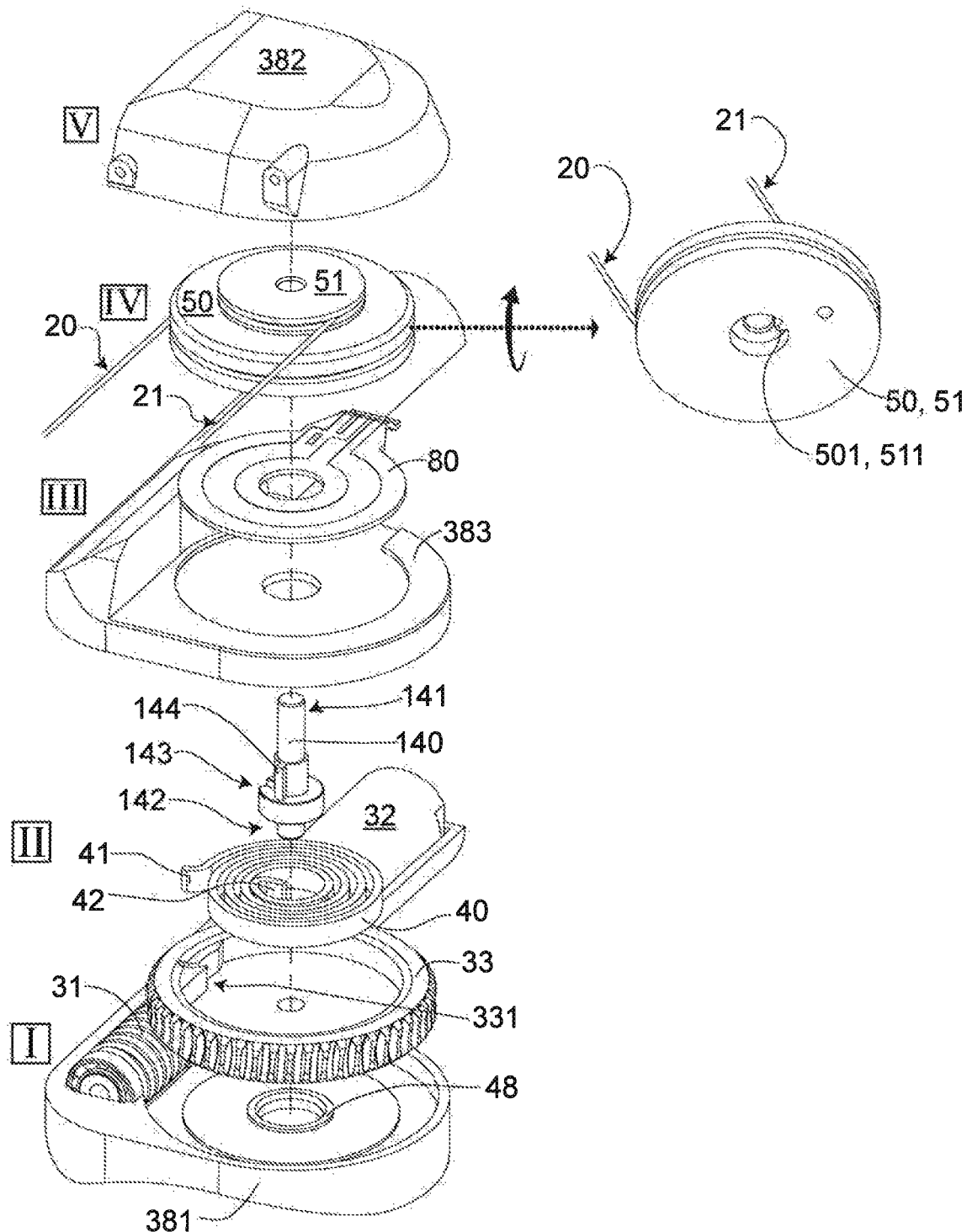

In FIGS. 15A and 15B, the device 10 is shown with all its modules I to V but not all of their functionalities, i.e. only module II with one or more free wheel members 140 is used as add-on feature for the device 10. When the device 10 is provided with the free wheel functionality in module II (all of the following aspects/embodiments of the device 10 in FIGS. 18 to 26 do not have the free wheel functionality in their module II) where the two different angular/rotary positions of each pulley 50, 51 or rotary arm 60, 61 are positioned at the angel α of at least 270° from each other, preferably between 270° to 360° from each other, or most preferred about 300° to 355° from each other, as seen in the plane of extension of the pulleys and/or the rotary arms, see FIGS. 16 and 17. This enables a corresponding free wheel rotary movement of the at least one pulley 50, 51 or rotary arm 60, 61 corresponding to a movement of the tendons 20, 21 and the body member 2 between a fully extended or retracted position/posture before the biasing member 40 is effected.

In FIGS. 15A to 17B, the device 10 comprises the drive mechanism 30 where the motor 32 (with or without a possible first gearbox) has a built in or external first angle/rotation sensor 81 and has its output shaft directly connected to the worm screw 31. The worm screw 31 is adapted for direct engagement with the worm wheel 33 after assembly.

The worm wheel 33 is connected with its inner slot 331 at the inside of the worm wheel for engagement with the outer end 41 of the biasing member 40, i.e. to one side of the biasing member, which biasing member in these FIGS. is a torsion spring in the shape of a clock spring. The other end 41 or other side of the biasing member 40 is connected to the free wheel member 140, which can rotate around the same axis as the worm wheel 33. In FIGS. 15 and 17, the free wheel member 140 is an axle or axis shaft, and in FIG. 16 a plate. The free wheel member 140 is connected to the pulley core 52 but with a free wheel interval between the two parts, i.e. the free wheel movement giving the certain play of movement between them as explained above for device 10 on FIGS. 14A and 14B. Here, the angular position of the pulley core 52 is also read by a second angle/rotation sensor 80 as in FIGS. 14A and 14B. The pulley core 52 is connected to the two pulleys 50, 51, the large pulley 50 and the small pulley 51 through a kind of spline joints 53. In FIGS. 15, 16 and 17, two tendons 20, 21 are mounted, one for each of the two pulleys 50, 51 and winded up in opposite directions.

Figure 18A:
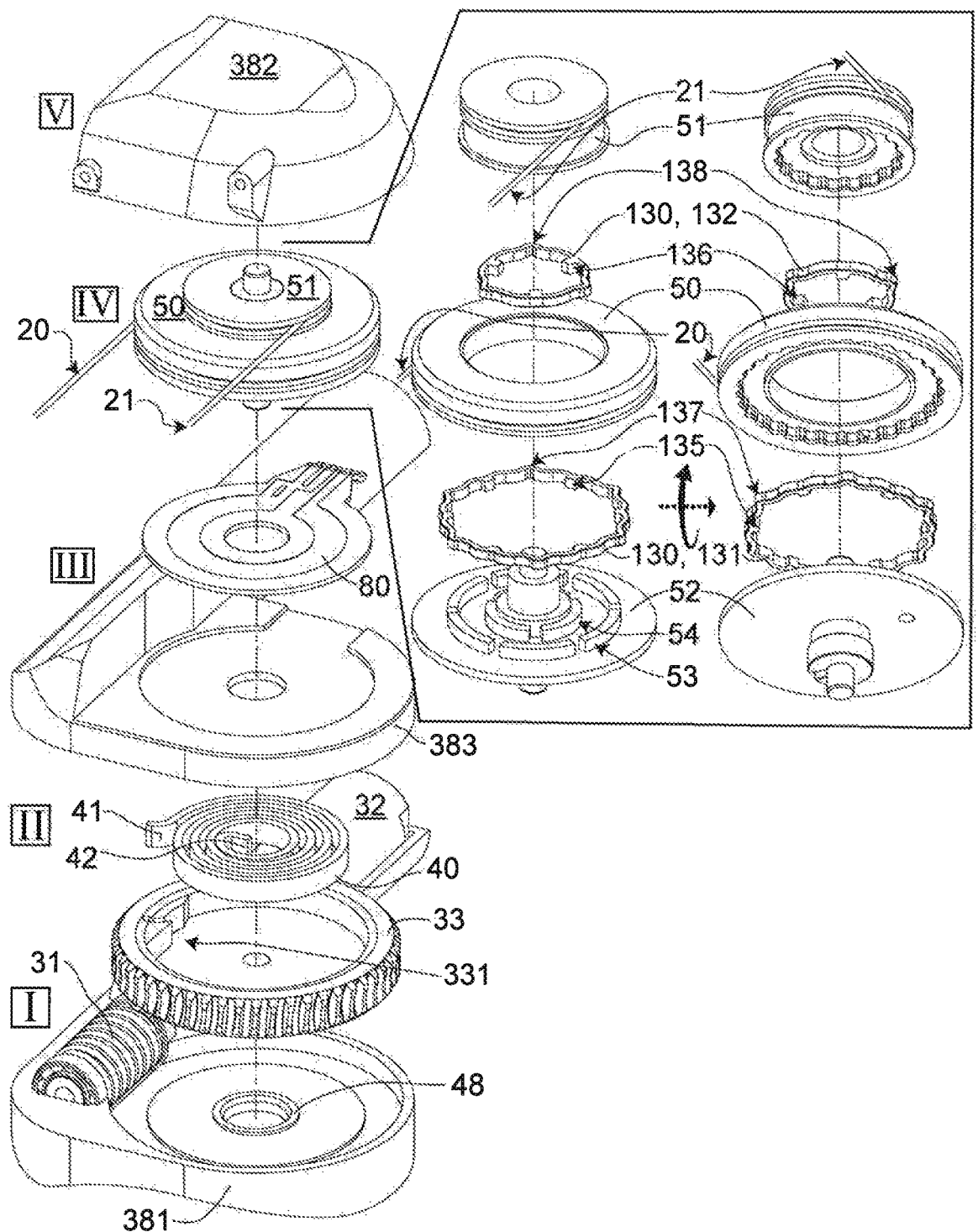
FIGS. 18A and 18B show three views of one more aspect of the device according to the invention with some of all features.
Figure 18B:
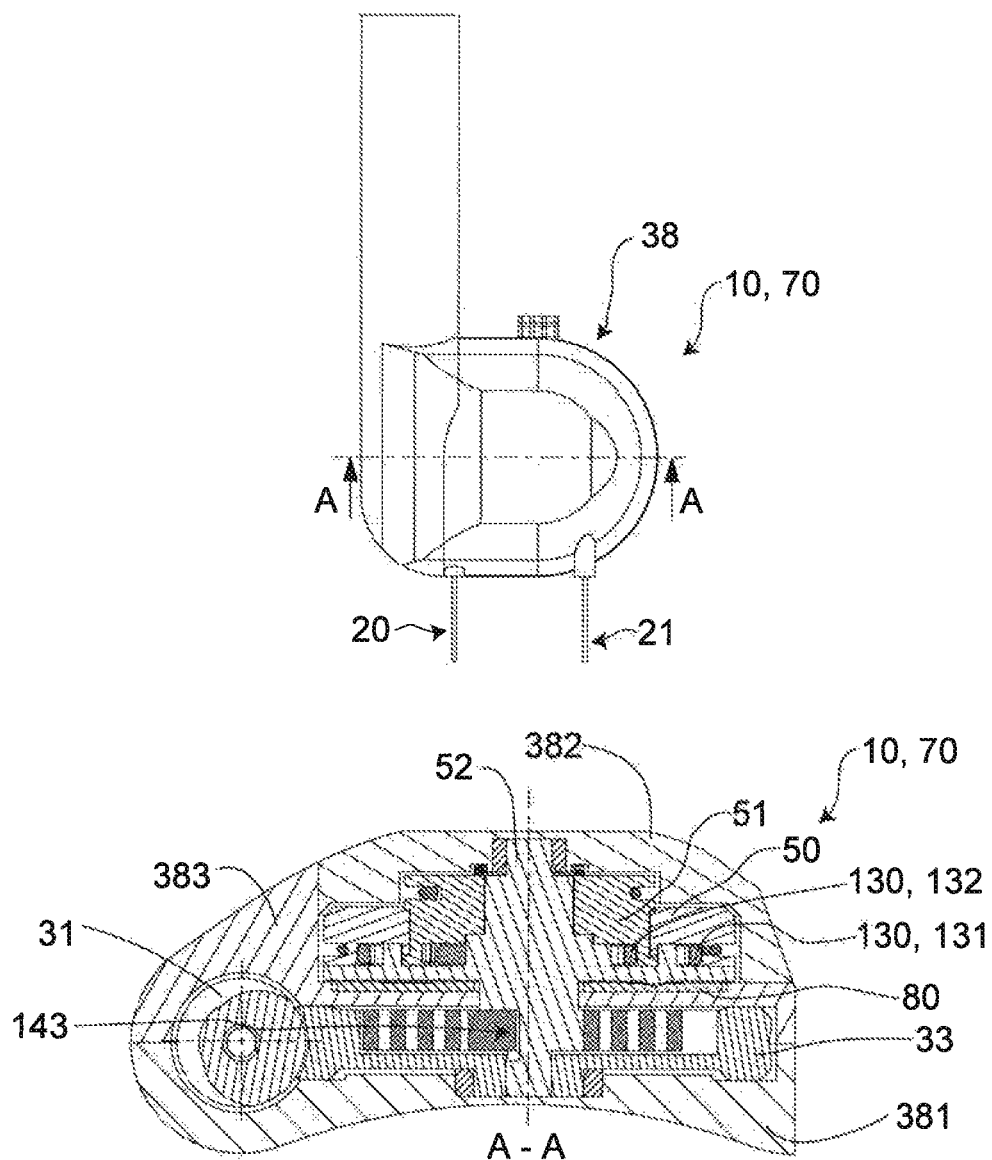
Figure 19A:
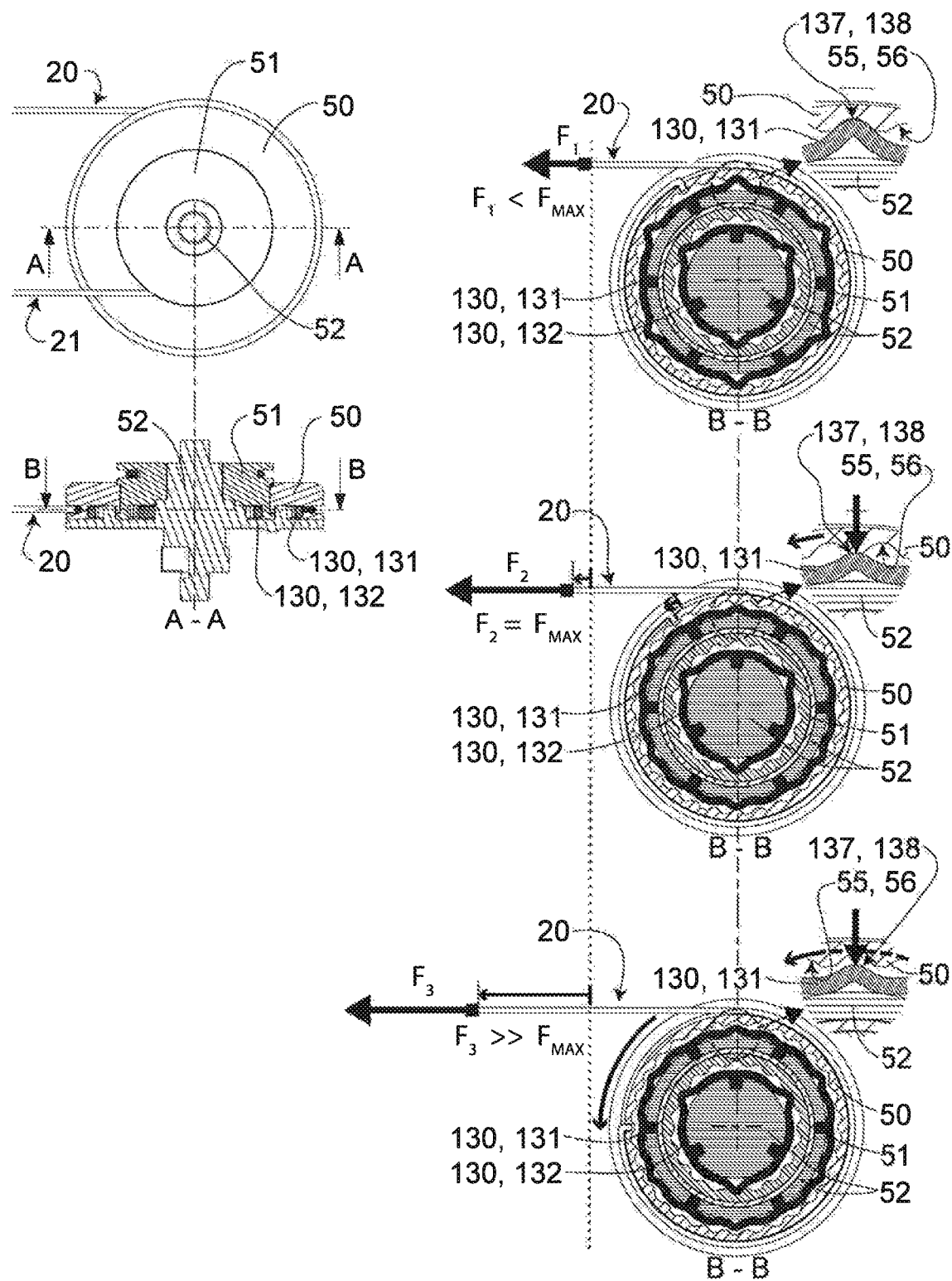
FIG. 19A shows module IV from above in the upper left view and this module in section along line A-A in the lower left view and the functionality of this module is visualised in three sectional views to the right along line B-B.
Figure 20A:
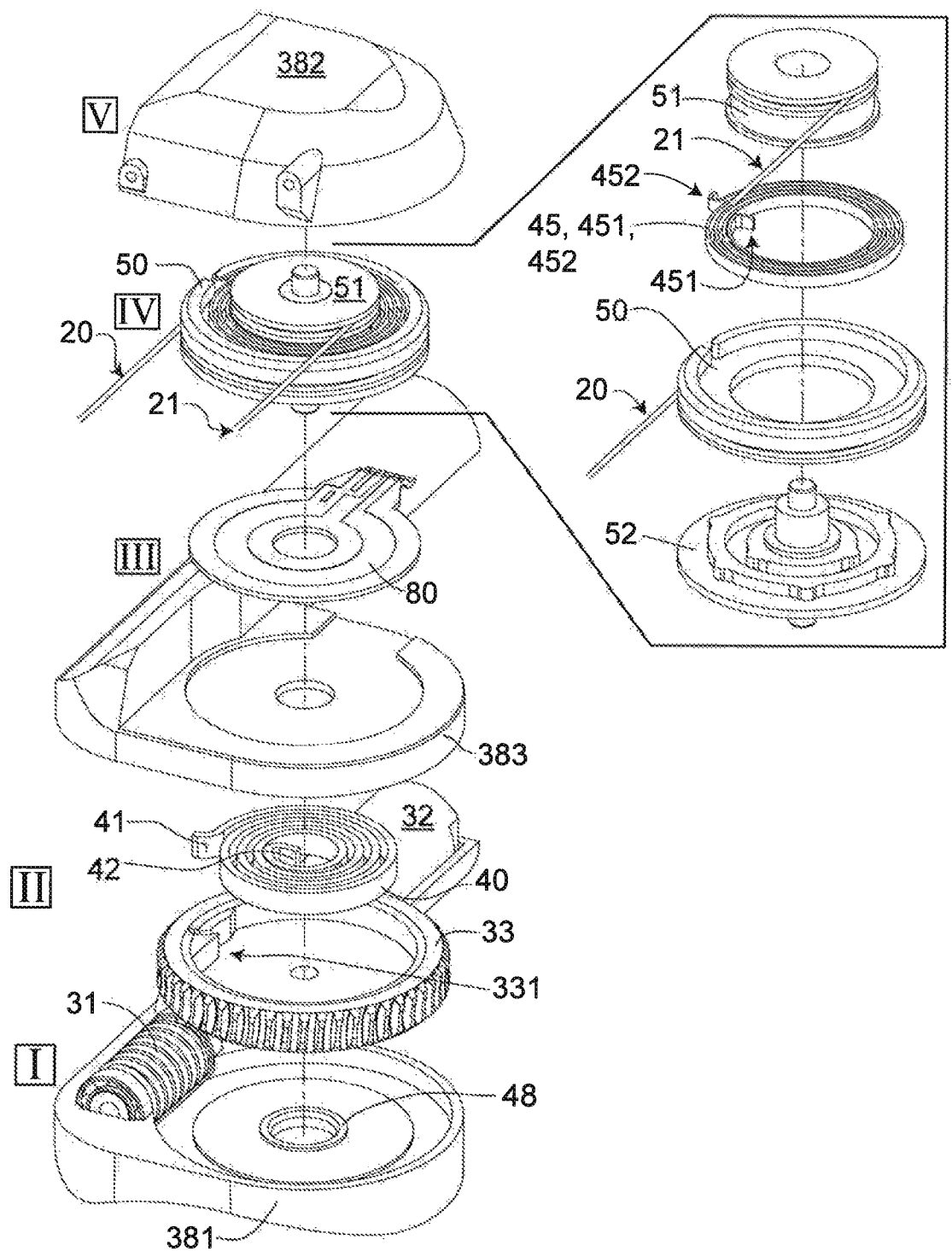
FIGS. 20A and 20B shows several views of still another aspect of the device according to the invention with some of all features.
Figure 20B:
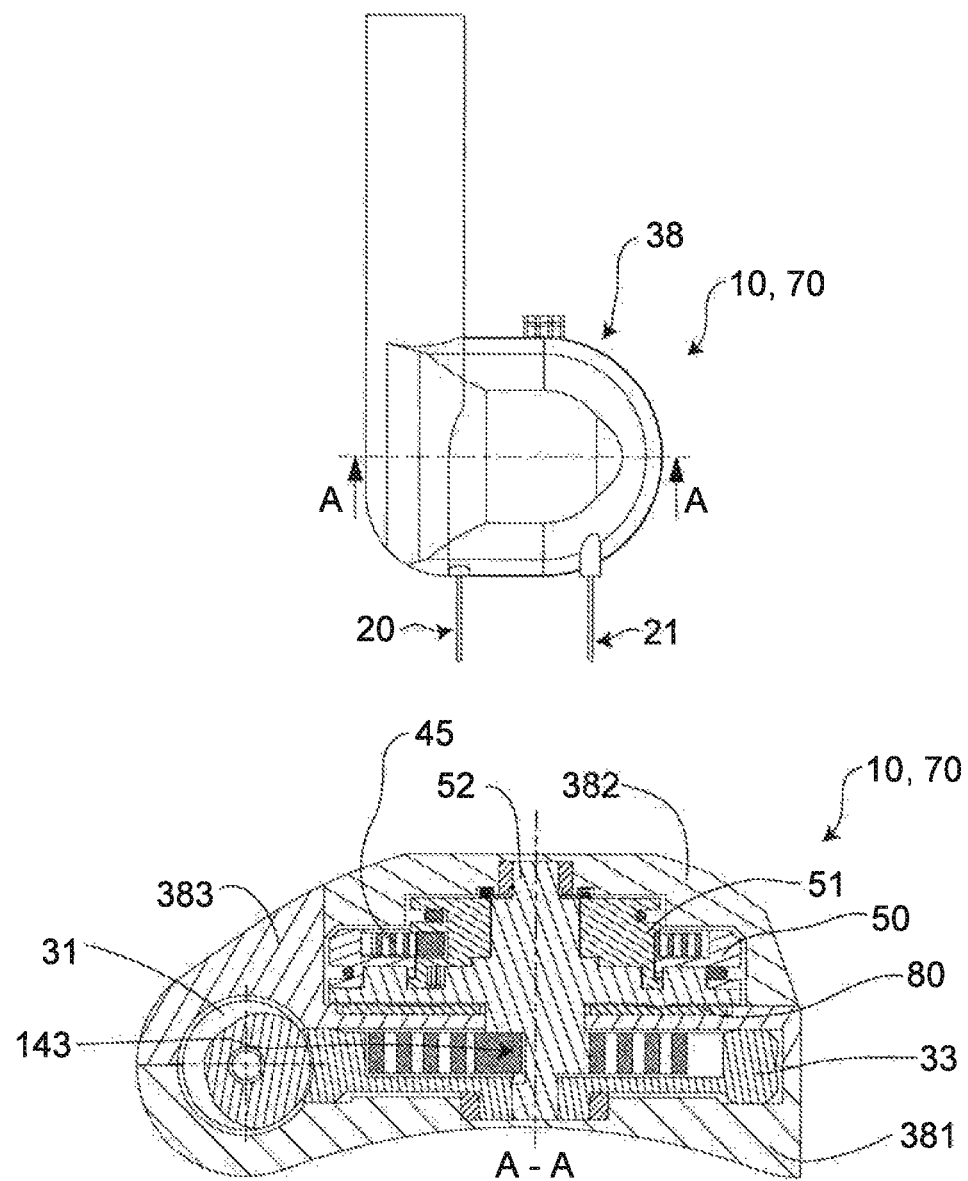

In FIGS. 18A to 19B, the device 10 is shown with all its modules I to V but not all of their functionalities, i.e. only module IV with one or more torque limiting mechanisms 130 is used as add-on feature for the device 10. In FIGS. 18, 19A and 19B, the device 10 comprises the drive mechanism 30 where the motor 32 (with or without a possible first gearbox) has a built in or external first angle or rotation sensor 81 and has its output shaft directly connected to the worm screw 31. The worm screw 31 is adapted for direct engagement with the worm wheel 33 after assembly. The worm wheel 33 is connected with its inner slot 331 at its inside for engagement with the outer biasing member end 41, i.e. to one side of the biasing member, which biasing member in these FIGS. is a torsion spring in the shape of a clock spring. In this device 10, the pulleys 50, 51 are part of a pulley or spool package being divided into the pulley core 52 and two pulleys 50, 51 with different diameters, i.e. the large pulley 50 and the small pulley 51. This device 10 comprises for safety a torque limiting mechanism 130 between each of the pulleys 50, 51 and the pulley core 52. Hence, each of those two torque limiters 130 comprises two somewhat flexible splined deformation rings 131, 132 with rigid anchoring in the pulley core 52 and a "ratchet"-like but smooth coupling, i.e. a flexible anchoring to each pulley 50, 51 for operation and drive therebetween, which deformation rings 131, 132 work independent from each other. This enables having different torque limits for the two different pulleys 50 and 51 and their tendons 20 and 21, respectively. This torque limiting functionality of module IV provides a safety if the motor 32 would fail and start to tension any of the tendons 20, 21 over the limit of what is safe or if external forces would pull the glove/finger/-s/tendon/-s with a force that could damage the device 10 or the user the torque limiter/s will "activate" and let the pulleys 50 and/or 51 rotate relative the pulley core 52 without damaging the user or the device. The same safety effect is provided with the ball and spring solution for a torque limiter 130 on FIG. 19B. In FIG. 19A, the upper left sectional view of the torque limiters 130, 131, 132 the F1 (in the active/operative tendon 20), and within the allowed interval for the torque limiting effect to be active, i.e. F1 is below Fmax in the other two lower sectional views. In the middle left sectional view in FIG. 19A of the torque limiters, the force F2 (in the active/operative tendon 20) is equal to the highest allowable force Fmax when the torque limiters starts to loose their anchoring, i.e. the torque limiters is about to disengage. In the lowermost sectional view of FIG. 19A, the force F3 (in the active/operative tendon 20) is higher or much higher than Fmax, whereby the torque limiter 130, 131 or 130, 132 (if the other tendon 21 was active/operative) lets or allows the associated pulley 50 or 51 or rotary arm to rotate until the force F3 has been lowered or ebbed away below the amount of Fmax, whereafter the torque limiting effect goes into operation again.

In FIGS. 18A to 19B, the device 10 comprises the drive mechanism 30 where the motor 32 (with or without a possible first gearbox) has a built in or external first angle/rotation sensor 81 and has its output shaft directly connected to the worm screw 31. The worm screw 31 is adapted for direct engagement with the worm wheel 33 after assembly. The worm wheel 33 is connected with its inner slot 331 at the inside of the worm wheel for engagement with the outer end 41 of the biasing member 40, i.e. to one side of the biasing member, which biasing member in these FIGS. is a torsion spring in the shape of a clock spring. The other end 41 or other side of the biasing member 40 is connected to the pulley core 52, which can rotate around the same axis as the worm wheel 33. Here, the angular position of the pulley core 52 is also read by a second angle/rotation sensor 80. The pulley core 52 is connected to the two pulleys 50, 51, the large pulley 50 and the small pulley 51 through a kind of spline joints 53. Here, two tendons 20, 21 are mounted, one for each of the two pulleys 50, 51 and winded up in opposite directions. Between the pulley core 52 and each of the pulleys 50, 51 there are separate torque limiting functions in module IV installed for the safety of the user and the device 10. Here, the spline joints 53, 54, 135, 136, 137, 138 of the torque limiter 130 are active parts of the device 10 as they in fact make the torque limiters 130 work for the pulleys 50, 51 in the same way as for the device in FIGS. 14A and 14B. The two pulleys 50, 51 are mounted together to prevent them from falling apart when not mounted on the pulley core 52, but with the possibility to rotate relative to each other about the same axis.

In FIGS. 20A, 20B and 21A, 21B, the device 10 is shown with all its modules I to V but not all of their functionalities, i.e. only module IV with a length adjustability functionality 45, 451, 452 is used as add-on feature for the device 10. For people with disabilities in their hands 4 it is important for their device 10 to be easy to use. Therefore an automatic tendon adjustment has been developed, so that it is easy to adjust the length of the tendons 20, 21 in the glove 5. This is, as an example, important for people with arthritis who's hands 4 and fingers 2 can differ in size from day to day depending on inflamations and swelling. Here, the two pulleys 50, 51 are mounted together to prevent them from falling apart when not mounted on the pulley core 52, but with the possibility to rotate relative to each other about the same axis. Between the two pulleys 50, 51 is the pre-tensioned biasing member 45 installed with its inner end 451 connected to the small pulley 51 and its outer end 452 connected to the large pulley 50. The pre-tensioned biasing member 45 works as an adjustment spring for the length of the tendons 20, 21. The length adjustment spring 45 is a torsion spring in the shape of a constant torque spring. When the pulley 50, 51 are mounted on the pulley core 52 the length adjustment spring 45 has no effect on the system, i.e. on the tendons 20, 21 as they then are rotatably locked together. When the two pulleys 50, 51 are detached and lifted from the pulley core 52 and thereby from the device 10 the length adjustment spring 45 with its pre-tension will force the pulleys to rotate with a relatively small torque in opposite directions and stretch/tension the tendons 20, 21 that runs out through one or more fingers 2 of a glove 5, if the device 10 is placed on a glove. Then, when a users hand 4 is inserted into the glove, the length adjustment spring 45 will let the tendons 20, 21 be released for a bit at the same time as they are in a stretched condition until the glove 5 is properly fitted on the hand 4 and any finger 2. When the pulleys 50, 51 then are assembled/mounted back on the pulley core 52 the length adjustment spring 45 will again have no effect on the tendons 20, 21, but the glove 5 with its tendons 20, 21 will be correctly adjusted into a good fit over the hand 4 and fingers 2 of the user and be ready for use.

In FIGS. 20A to 21B, the device 10 comprises the drive mechanism 30 where the motor 32 (with or without a possible first gearbox) has a built in or external first angle/rotation sensor 81 and has its output shaft directly connected to the worm screw 31. The worm screw 31 is adapted for direct engagement with the worm wheel 33 after assembly. The worm wheel 33 is connected with its inner slot 331 at the inside of the worm wheel for engagement with the outer end 41 of the biasing member 40, i.e. to one side of the biasing member, which biasing member in these FIGS. is a torsion spring in the shape of a clock spring. The other end 41 or other side of the biasing member 40 is connected to the pulley core 52, which can rotate around the same axis as the worm wheel 33. Here, the angular position of the pulley core 52 is read by the second angle/rotation sensor 80. The pulley core 52 is connected to the two pulleys 50, 51, the large pulley 50 and the small pulley 51 through a kind of spline joints 53. Here, two tendons 20, 21 are mounted, one for each of the two pulleys 50, 51 and winded up in opposite directions. The two pulleys 50, 51 are assembled together to prevent them from falling apart when not mounted on the pulley core 52, but with the possibility to rotate relative to each other about the same axis.

Figure 22A:
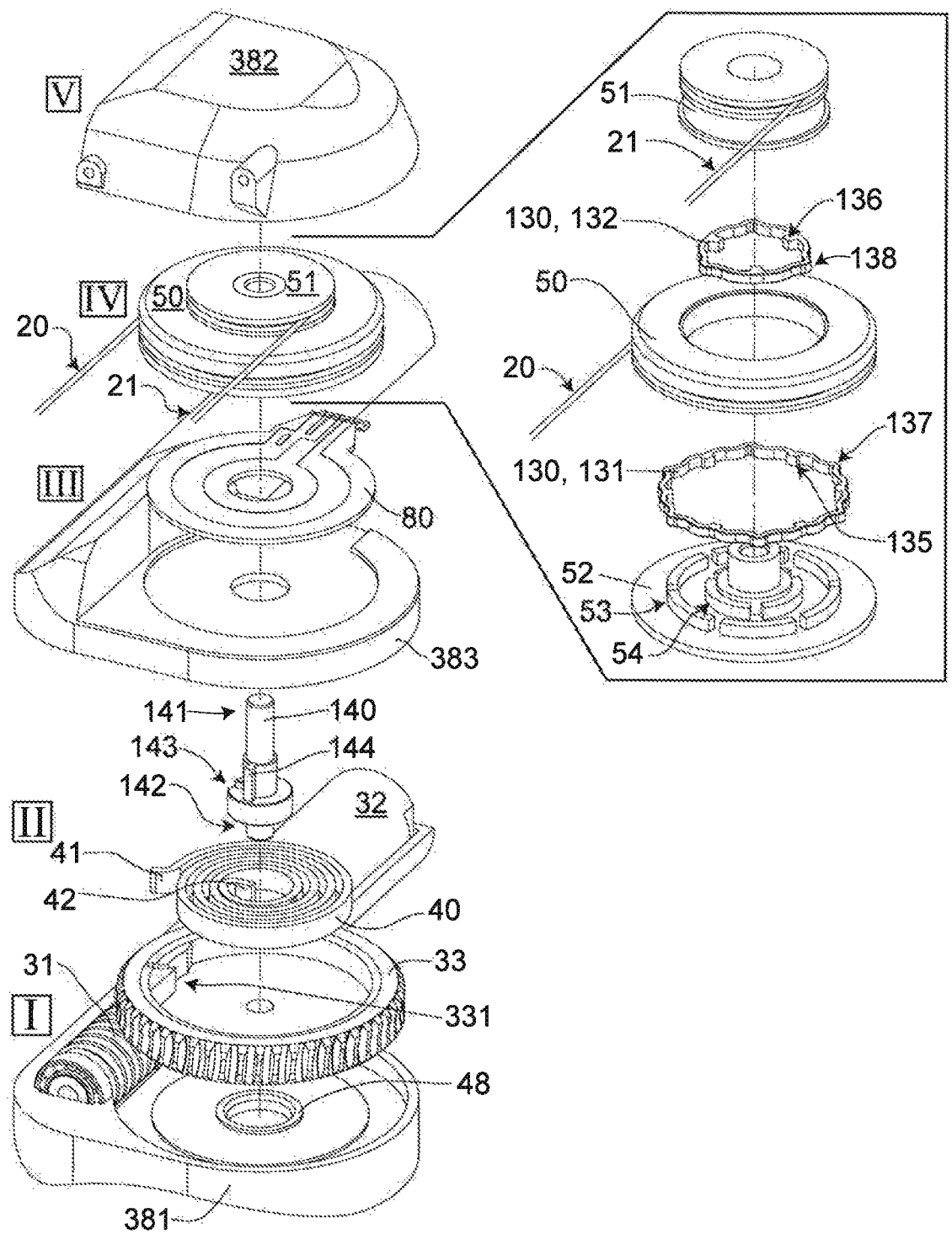

In FIGS. 22A and 22B, the device 10 is shown with all its modules I to V but not all of their functionalities, i.e. only module IV with one or more torque limiting mechanisms 130 and module II with one or more free wheel members 140 are used as add-on features for the device 10. 1. Hence, the same parts, functionalities, effects and improvements as explained for the devices 10 of FIGS. 18A to 19B and the torque limiting function, and FIGS. 14A, 14B, 15A, 15B, 16, 17A and 17B and for the free wheel function are applied for this device 10 in FIGS. 22A and 22B.

Figure 23A:
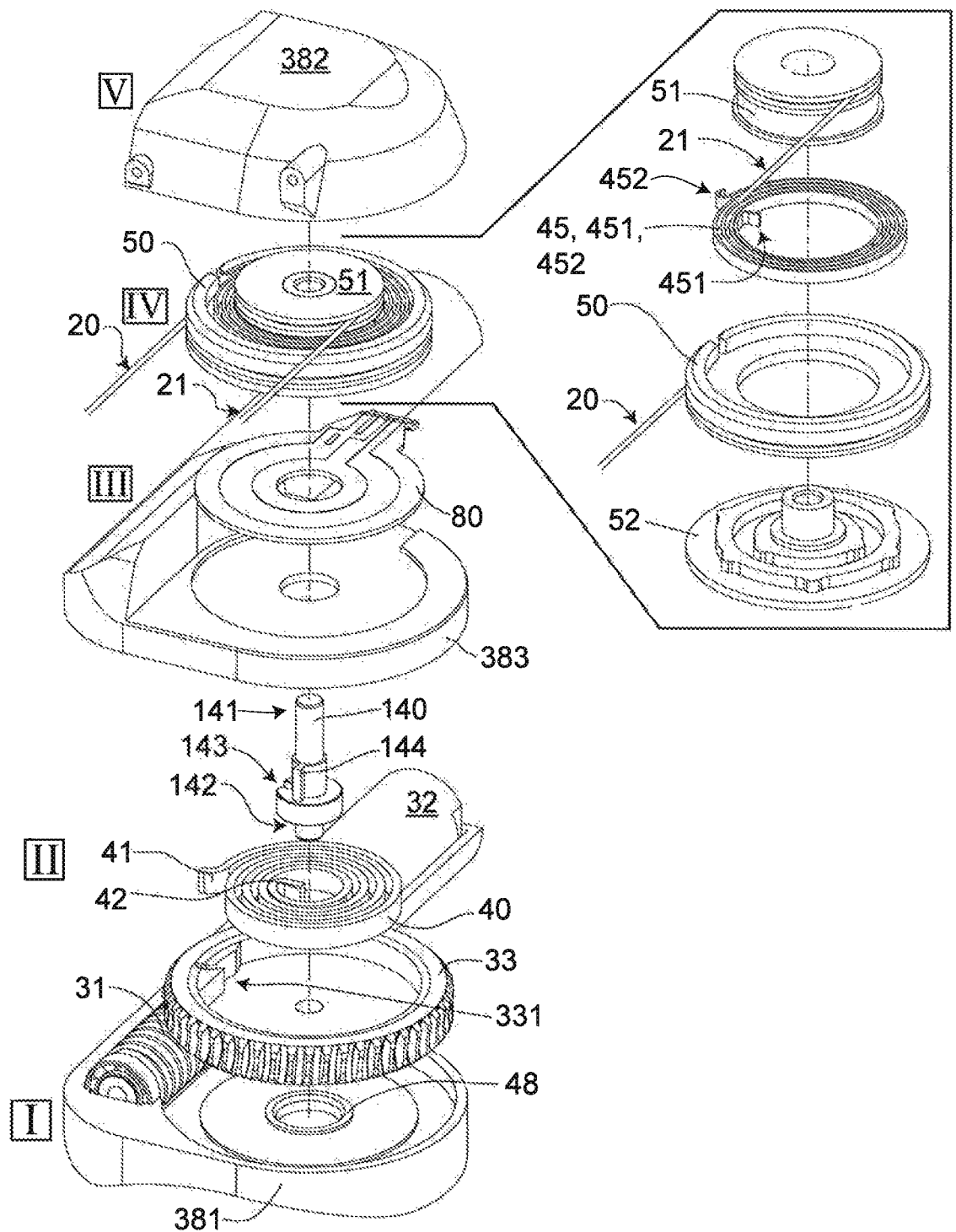

In FIGS. 23A and 23B, the device 10 is shown with all its modules I to V but not all of their functionalities, i.e. only module IV with one or more length adjustability functionalities 45, 451, 452 and module II with one or more free wheel members 140 are used as add-on features for the device 10. 1. Hence, the same parts, functionalities, effects and improvements as explained for the devices 10 of FIGS. 20A, 20B and 21A, 21B and the tendon length adjustablity function, and for FIGS. 14A, 14B, 15A, 15B, 16, 17A and 17B and the free wheel function are applied for this device 10 in FIGS. 23A and 23B.

Figure 24A:
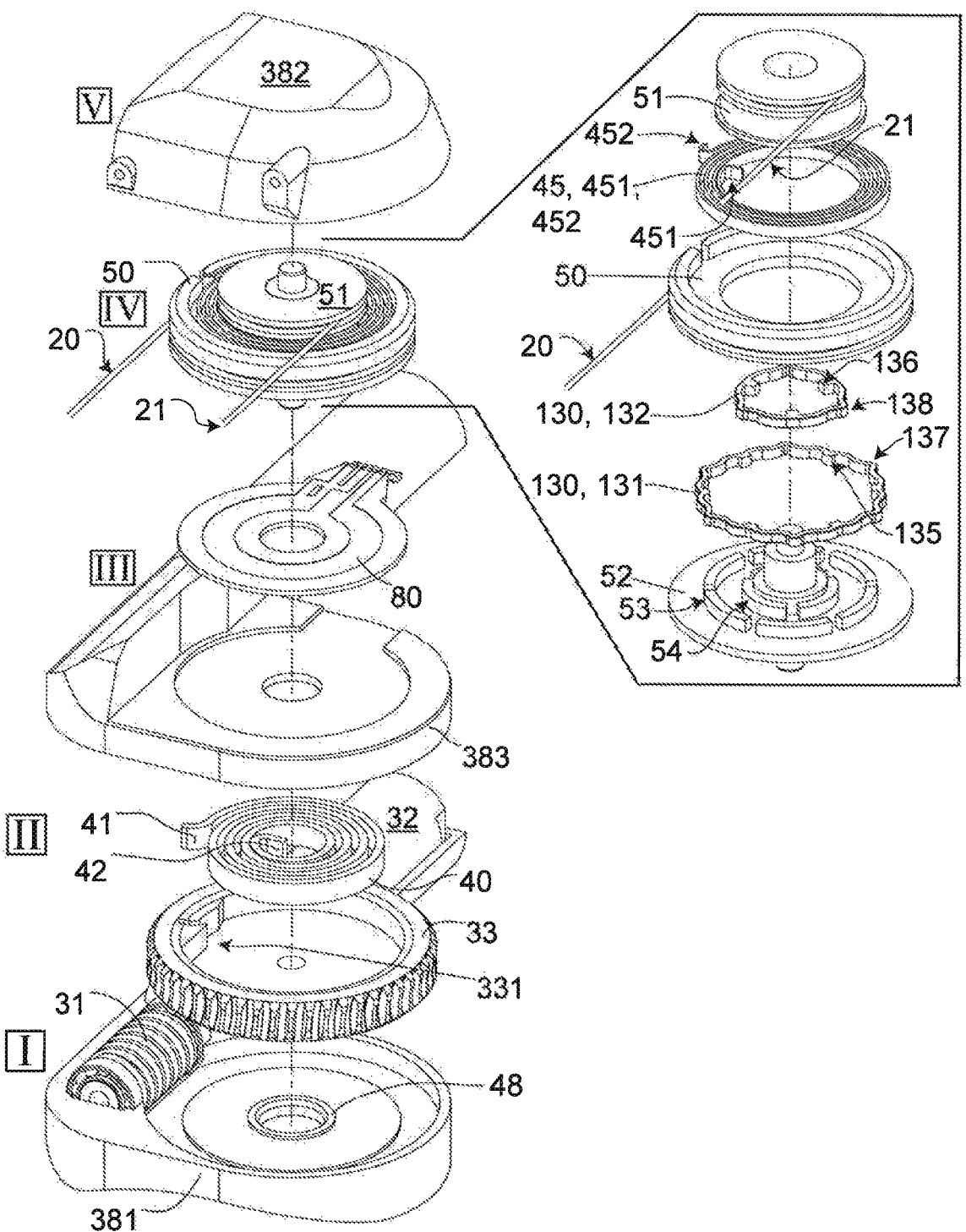

In FIGS. 24A and 24B, the device 10 is shown with all its modules I to V but not all of their functionalities, i.e. only module IV with one or more length adjustability functionalities 45, 451, 452 and with one or more torque limiting mechanisms 130 are used as add-on features for the device 10. 1. Hence, the same parts, functionalities, effects and improvements as explained for the devices 10 of FIGS. 20A, 20B and 21A, 21B and the tendon length adjustablity function, and for FIGS. 18A to 19B and the torque limiting function are applied for this device 10 in FIGS. 24A and 24B.

Figure 25:
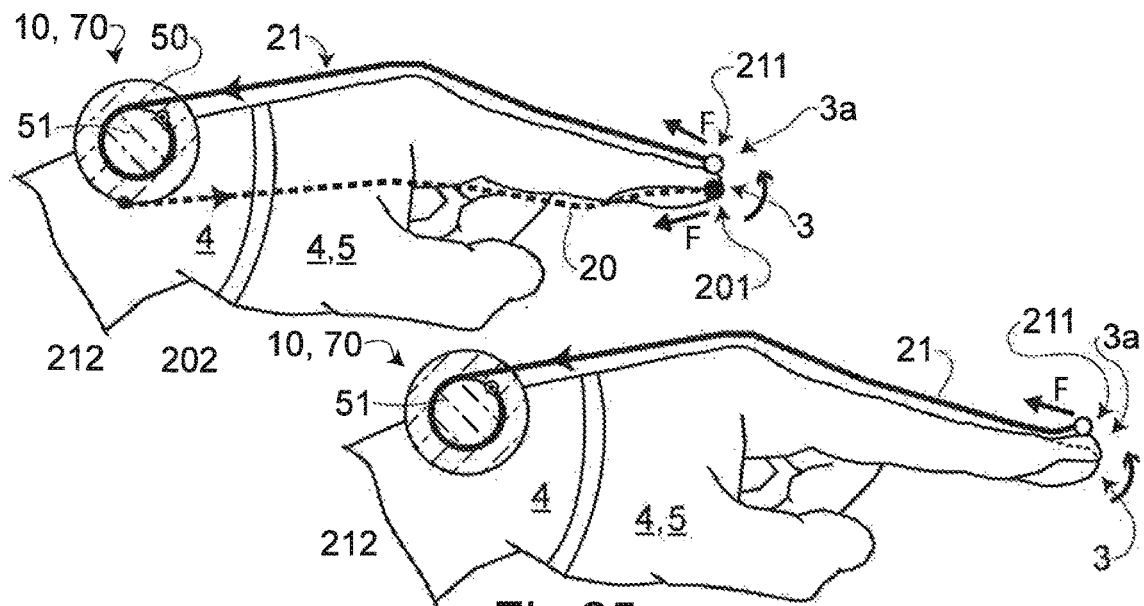
FIG. 25 shows two views of yet one more aspect of the device according to the invention with one or more of all inventive features. Here, the design and functionality of this aspect of the device is visualised in two side views, i.e. the upper view shows the inventive functionality and design of the device while the lower view shows an example of another design of a device that is not workable when the device is placed/arranged and used on a hand/body member.
Figure 26:
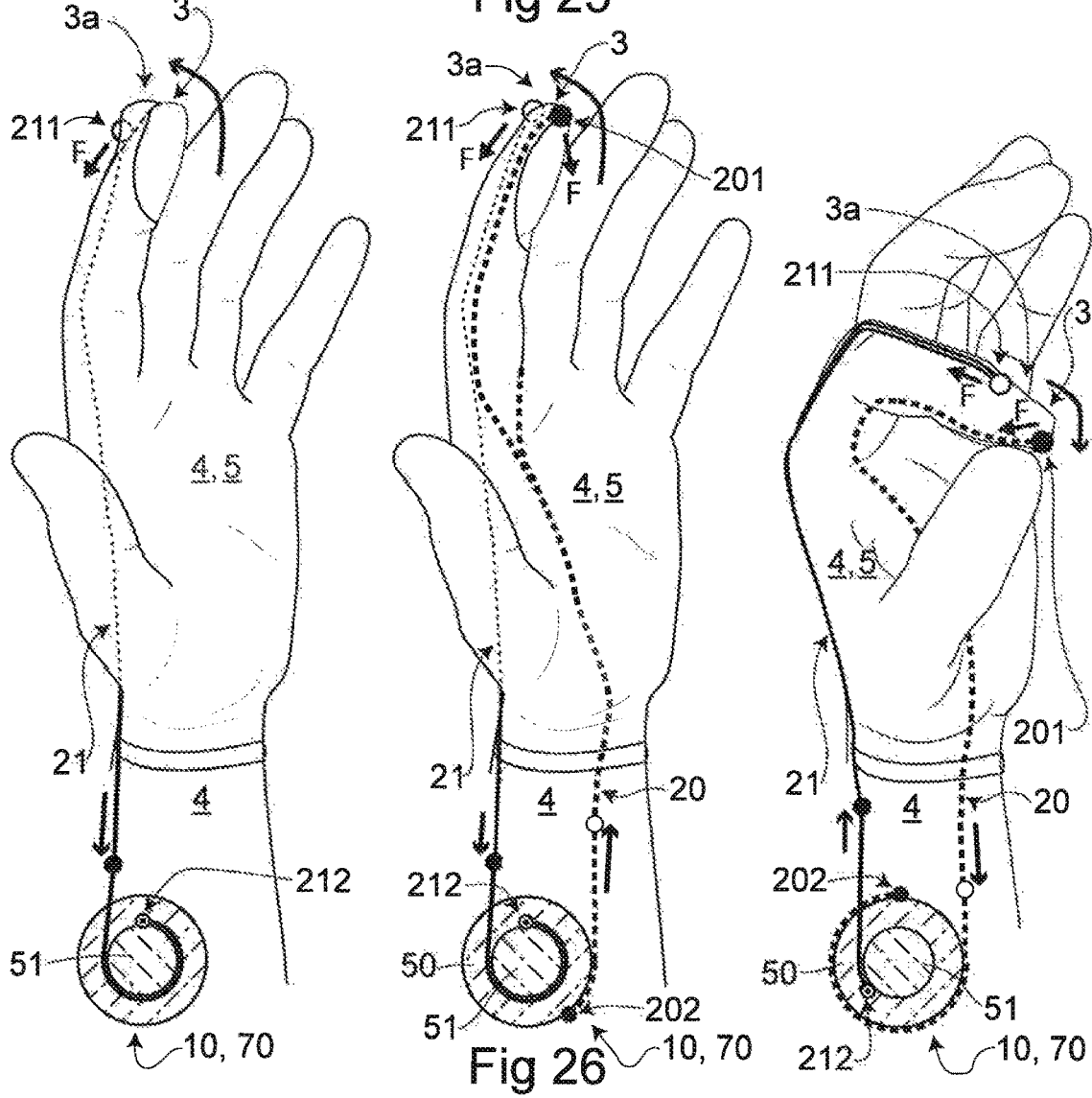
FIG. 26 shows two views of the device as shown in the upper view of FIG. 25 in perspective to the right while the leftmost view shows the non-workable device in perspective. Here, the design and functionality of this aspect of the device is visualised in the two right views, i.e. the middle view shows the inventive functionality and design of the device in one mode and the rightmost view shows that this device works by not loosing its grip of a fingertip of the hand when the device is actuated in another mode to move the fingertip away from a thumb.

In FIGS. 25 and 26, the device 10 is shown with all its modules I to V but not with the motor for simplicity, even though the motor moves the tendons 20, 21, and with at least one or more or all of the module functionalities as explained above. Here, for each of the actuated fingers 2 there are one or more tendons 20, 21 on each of the two opposing sides 2a, 2b of the finger 2 corresponding to the directions that the finger will be bent. The opposing tendons 20, 21 will follow each other's movements and never be slacked due to the design as explained above with different diameters of the spools for the opposing tendons. This fact is used to design the glove 5 with significantly big openings for the fingertips 3, 3a, and even to leave the whole inside/underside of the finger 2 open or bare. This is because the tendons 20, 21, which are fastened in the tip 3a of the finger part 3 of the glove 5, always holds the finger part of the glove in place when the tendons follow each other's movements. For example, if the tip 3a of the finger's upper side 2b is tensioned to straighten the finger 2, the glove's finger part 3a would most likely jump off the finger 2 if no tendons 20 where on the underside 2a of the finger 2 holding the glove's finger part or coverage 3a in place. This is proven, i.e. as long as the tendons are held on the top and the underside of the finger 2 unslacked, the glove's finger part coverage 3a does not jump off the finger, even though the underside 2a of the finger is not covered with the finger part coverage 3a of the glove 5.

In FIGS. 25 and 26, and other figures, the arrows, both without the letter F and with it, following the tendons 20, 21 and the fingertip 3, 3a visualise the movement of tendons (and directions of forces) and the body member 2, i.e. fingertip 3 and the fingertip coverage 3a to clarify the holding or keeping in place effect using at least two tendons 20, 21 and not only one tendon 21 that would pull off the fingertip coverage 3a. However, the inventive design of the laying out and placing of both tendons 20, 21 in the device 10 eliminate this risk of undesired pulling off of the fingertip coverage 3a.

Moreover, the size of the free wheel movement visualised by angle α depends on the dimensions, sizes, i.e. diameters of the pulleys 50, 51 and the length of the rotary arms 60, 61, whereby this angle could be of any other size than the defined ones, e.g. be between 5° to 350°.

In one aspect, the device 10 comprises two pairs of pulleys 50, 51, i.e. one pair of pulleys 50, 51 and another pair of pulleys 50, 51, each pair being a set of pulleys. These two pairs or sets of pulleys 50, 51 could be assembled together side-by-side or stapled together similar to plates stapled together with a common or mutual rotary axis and a common or mutual free wheel function or one free wheel member 140 for each set or pair of pulleys 50, 51, such that each pulley pair or set of pulleys is freely rotatable in relation to each other and the free wheel member about or around a common axis.

NOMENCLATURE

1: Joint. 2: Arm/Finger. 2a: First/other/lower side and/or under-/inside of body member/part/arm/finger/limb. 2b: Second/Dorsal/Upper side of body member/arm/finger. 3: Proximal/Free end of arm/finger. 3a: Fingertip/nail coverage. 4: Body member/Hand. 5: Glove. 10: Device. 20: First tendon. 20': Elongation/Additional tendon part/section associated with first tendon (via tackle). 201: One/First end of first tendon. 201': First end of prolonging first tendon part. 202: Other/One/Second end of first tendon. 202': Second end of prolonging first tendon part. 21: Second or third or fourth or fifth (or more) tendon. 211: One/First end of second tendon. 212: Other/One/Second end of second/third tendon. 22: Tendon tension sensor/unit/feedback signal. 30: Driving mechanism/Self-inhibiting gear, e.g. worm gear/worm gear unit/worm reduction gear. 31: Worm screw. 32: Motor for powering the driving mechanism, e.g. electrically driven linearly or rotationally. 321: Motor controller. 33: Worm wheel. 331: Slot at inside of worm wheel for engagement with outer biasing member end 41. 34: Sun gear. 35: Ring gear. 36: Planetary gear carrier. 37: Planetary gear. 38: Outer casing 39: Gear wheels. 381: Bottom/Lower plate of casing 38. 382: Upper plate of casing 38. 383: Middle/Intermediary plate of casing 38. 40: Bias or Biasing mechanism/member/organ. 41: One/First/Outer end of bias/biasing mechanism or member or organ 40. 42: Another/Second/Inner end of bias/biasing mechanism/member/organ. 43: Casing for biasing member. 44: Flexible part/member/section of tendon. 45: Adjustment spring. 451: First or inner end of adjustment spring. 452: Second/Outer end of adjustment spring. 46: Pressure/Wave spring. 47: First bearing. 48: Second bearing. 50: First/Primary/Large pulley. 501: Pin for engaging free wheel member 140. 51: Second or secondary/Small pulley. 511: Pin for engaging free wheel member 140. 52: Spools/Pulley core or hub. 53, 54: Spline joints on pulley core to engage spline joints on pulleys. 55, 56: Recesses/Dents/Dimples in pulley for rings 131,132/balls 133 to engage/disengage. 60: One/First/Primary/Long rotary arm. 601: One/First end of first arm. 602: Other/One/Second end of first arm. 61: Another/Second/Secondary/Short rotary arm. 611: One/First end of second arm. 612: Other/Second end of second arm. 70: Control unit for device 10. 71: Signal acquisition/activation signal. 72: Micro controller (MCU). 73: Control application. 74: Position controller. 75: Velocity controller. 76: Current controller. 77: Current feedback. 78: Velocity feedback. 79: Motor position feedback. 80: First sensor, e.g. optical encoder, on pulley/spool/arm 50, 51, 60, 61. 81: Second/Third sensor, e.g. optical encoder on motor 32 and/or worm gear 30. 82: Control unit for detection/control of relative position between winding part 31/bias member 40. 83: Fourth/Fifth sensor, e.g. laser sensor on motor and/or bias mechanism to enable measure movement and/or tension of biasing organ. 90: Rack for transfer of linear movement of driving mechanism to gear wheel. 91: Nut transferring rotary movement from screw linearly to worm wheel. 92: Linkage/Arm/Linkage arm/member (stiff): 93: Joint (pivot/rotary). 94: Static joint between arms 60, 61 about which both arms rotate. 100: Tackle. 110: Fixed/Attachment point for first/second/additional tendon part/section. 120: Centre axis/point of tackle. 130: Torque limiter. 131: Large torque limiter ring. 132: Small torque limiter ring. 133: Torque limiter balls. 134: Torque limiter springs. 135: Spline joint on ring 131 to engage spline joint 53 on pulley core 52. 136: Spline joint on ring 132 to engage pulley core joint 54. 137: Spline joint on ring 131 to engage pulley recess 55. 138: Spline joint on ring 132 to engage pulley recess 56. 140: Free wheel member/axle/plate. 141: First/Upper/Outer end/side of free wheel member. 142: Second/Lower/Inner end/side of free wheel member. 143: Slot at second free wheel member end/side for engaging biasing member end 42. 144: Protrusion on first free wheel member for engaging pulley 50, 51 or arm 60, 61.

The invention claimed is:

1. A device for pivoting a distal portion of an elongated body member around a joint, said joint being included in the elongated body member, said elongated member comprising a proximal portion and the distal portion, which are arranged on opposite sides of the joint in a longitudinal direction of the elongated body member, the device comprising:
   a driving mechanism configured for arrangement at the proximal portion of the elongated body member;
   a motor for driving the driving mechanism; and
   an actuation device, which is connected to the driving mechanism and operable to generate a torque around the joint;
   wherein the actuation device comprises a first artificial tendon that has a proximal end and a distal end, the distal end being configured for arrangement at the distal portion of the elongated body member, and the proximal being attached to the driving mechanism, the first artificial tendon thereby extending in a first path along the elongated body member across the joint;
   wherein the actuation device comprises a second artificial tendon that has a proximal end and a distal end, the distal end being configured for arrangement at the distal portion of the elongated body member, and the proximal end being is attached to the driving mechanism, the second artificial tendon thereby extending in a second path along the elongated body member across the joint; and
   wherein the driving mechanism comprises a driving wheel operatively coupled to the motor, the driving wheel being operatively arranged between the motor and each proximal end of the first and second artificial tendons;
   wherein the driving mechanism is arranged, when operated by the motor to move the driving wheel, to pull the first artificial tendon to generate a first torque in a first direction around the joint and perform a first movement while simultaneously enabling the second artificial tendon to follow the first movement of the first artificial tendon, and to pull the second artificial tendon to generate a second torque in a second direction around the joint and perform a second movement while simultaneously enabling the first artificial tendon to follow the second movement of the second artificial tendon;
   wherein the driving mechanism is arranged to provide a bi-directional pivoting movement of the distal portion of the elongated body member around the joint with the first artificial tendon and the second artificial tendon, respectively, being kept taut when it follows the movement of the second artificial tendon and the first artificial tendon, respectively;
   wherein a biasing member is arranged between the driving wheel of the driving mechanism and each proximal end of the first and second tendons,
   wherein the driving mechanism comprises at least one pulley or rotary arm to which the proximal end of at least the first artificial tendon is attached,
   wherein the at least one pulley or rotary arm is operatively arranged between the biasing member and the proximal end of the first artificial tendon,
   wherein the first artificial tendon is non-elastic; and
   wherein the first artificial tendon is configured for being attached with its distal end to the distal portion of the elongated body member by a fingertip coverage, and wherein the second artificial tendon is configured for being attached with its distal end to the distal portion of the elongated body member by said fingertip coverage, which at least partly covers the dorsal side of a fingertip on the elongated body member.

2. The device according to claim 1, wherein the proximal ends of at least the first artificial tendon and the second artificial tendon are individually attached to said at least one pulley or rotary arm.

3. The device according to claim 1, wherein the first path is configured for being arranged at a first side of the joint and the second path is configured for being arranged at a second side of the joint at least partly opposite the first side.

4. The device according to claim 1, further comprising a self-inhibiting drive member, which is arranged between the motor and the driving wheel of the driving mechanism, wherein the self-inhibiting drive member is immobile when the motor is not operated.

5. The device according to claim 1, further comprising a first sensor for sensing a position of the motor and a second sensor for sensing a linear movement or an angle of rotation of said at least one pulley or rotary arm in response to movement of each of the first and second artificial tendons and, wherein the position of the motor and the linear movement or angle of rotation are used to determine a position of the elongated body member and to determine biasing of the biasing member and thereby a pulling force in each of the first and second artificial tendons.

6. The device according to claim 1, further comprising a free wheel member, which is arranged such that when the first artificial tendon is pulled, the at least one pulley or rotary arm is moved freely without engaging the biasing member until a certain magnitude of free movement is reached.

7. The device according to claim 6, wherein the free wheel member is arranged such that when any of the first and second artificial tendons is pulled, an associated pulley or rotary arm is moved freely without engaging the biasing member until the certain magnitude of free movement is reached.

8. The device according to claim 6, wherein the free wheel member is arranged between the biasing member and the at least one pulley or rotary arm.

9. The device according to claim 6, wherein the free wheel member has a first end in engagement with the biasing member and a second end arranged to be in engagement with the at least one pulley or rotary arm only in two separated angular positions for the at least one pulley or rotary arm, said separated angular positions resulting from movement of at least one of the first and second artificial tendons in the first and second directions.

10. The device according to claim 9, wherein the separated angular positions comprises a first angular position and a second angular position, wherein the second end of the free wheel member is adapted to only be in engagement with the at least one pulley or rotary arm in the first angular position of the at least one pulley or rotary arm when the first artificial tendon has been moved a first distance in one direction among the first and second directions and only be in engagement with the at least one pulley or rotary arm in a second angular position when the first artificial tendon has been moved a second distance in an opposite direction among the first and second directions, whereby the at least one pulley or rotary arm is moved freely between the first and second angular positions.

11. A device for pivoting a distal portion of an elongated body member around a joint, said joint being included in the elongated body member, said elongated member comprising a proximal portion and the distal portion, which are arranged on opposite sides of the joint in a longitudinal direction of the elongated body member, the device comprising:

a driving mechanism configured for arrangement at the proximal portion of the elongated body member;

a motor for driving the driving mechanism;

an actuation device, which is connected to the driving mechanism and operable to generate a torque around the joint;

wherein the actuation device comprises a first artificial tendon that has a proximal end and a distal end, the distal end being configured for arrangement at the distal portion of the elongated body member, and the proximal being attached to the driving mechanism, the first artificial tendon thereby extending in a first path along the elongated body member across the joint;

wherein the actuation device comprises a second artificial tendon that has a proximal end and a distal end, the distal end being configured for arrangement at the distal portion of the elongated body member, and the proximal end being is attached to the driving mechanism, the second artificial tendon thereby extending in a second path along the elongated body member across the joint; and wherein the driving mechanism comprises a driving wheel operatively coupled to the motor, the driving wheel being operatively arranged between the motor and each proximal end of the first and second artificial tendons;

wherein the driving mechanism is arranged, when operated by the motor to move the driving wheel, to pull the first artificial tendon to generate a first torque in a first direction around the joint and perform a first movement while simultaneously enabling the second artificial tendon to follow the first movement of the first artificial tendon, and to pull the second artificial tendon to generate a second torque in a second direction around the joint and perform a second movement while simultaneously enabling the first artificial tendon to follow the second movement of the second artificial tendon;

wherein the driving mechanism is arranged to provide a bi-directional pivoting movement of the distal portion of the elongated body member around the joint with the first artificial tendon and the second artificial tendon, respectively, being kept taut when it follows the movement of the second artificial tendon and the first artificial tendon, respectively;

wherein a biasing member is arranged between the driving wheel of the driving mechanism and each proximal end of the first and second tendons, wherein the driving mechanism comprises at least one pulley or rotary arm to which the proximal end of at least the first artificial tendon is attached, wherein the at least one pulley or rotary arm is operatively arranged between the biasing member and the proximal end of the first artificial tendon, wherein the first artificial tendon is non-elastic;

wherein the device further comprises a free wheel member, which is arranged such that when the first artificial tendon is pulled, the at least one pulley or rotary arm is moved freely without engaging the biasing member until a certain magnitude of free movement is reached; and wherein the free wheel member has a first end in engagement with the biasing member and a second end arranged to be in engagement with the at least one pulley or rotary arm only in two separated angular positions for the at least one pulley or rotary arm, said separated angular positions resulting from movement of at least one of the first and second artificial tendons in the first and second directions.

12. The device according to claim 11, wherein the proximal ends of at least the first artificial tendon and the second artificial tendon are individually attached to said at least one pulley or rotary arm.

13. The device according to claim 11, wherein the first path is configured for being arranged at a first side of the joint and the second path is configured for being arranged at a second side of the joint at least partly opposite the first side.

14. The device according to claim 11, further comprising a self-inhibiting drive member, which is arranged between the motor and the driving wheel of the driving mechanism, wherein the self-inhibiting drive member is immobile when the motor is not operated.

15. The device according to claim 11, further comprising a first sensor for sensing a position of the motor and a second sensor for sensing a linear movement or an angle of rotation of said at least one pulley or rotary arm in response to movement of each of the first and second artificial tendons and, wherein the position of the motor and the linear movement or angle of rotation are used to determine a position of the elongated body member and to determine biasing of the biasing member and thereby a pulling force in each of the first and second artificial tendons.

16. The device according to claim 11, wherein the free wheel member is arranged such that when any of the first and second artificial tendons is pulled, an associated pulley or rotary arm is moved freely without engaging the biasing member until the certain magnitude of free movement is reached.

17. The device according to claim 11, wherein the free wheel member is arranged between the biasing member and the at least one pulley or rotary arm.

18. The device according to claim 11, wherein the separated angular positions comprises a first angular position and a second angular position, wherein the second end of the free wheel member is adapted to only be in engagement with the at least one pulley or rotary arm in the first angular position of the at least one pulley or rotary arm when the first artificial tendon has been moved a first distance in one direction among the first and second directions and only be in engagement with the at least one pulley or rotary arm in a second angular position when the first artificial tendon has been moved a second distance in an opposite direction among the first and second directions, whereby the at least one pulley or rotary arm is moved freely between the first and second angular positions.

19. The device according to claim 11, wherein the first artificial tendon is configured for being attached with its distal end to the distal portion of the elongated body member by a fingertip coverage, and wherein the second artificial tendon is configured for being attached with its distal end to the distal portion of the elongated body member by said fingertip coverage, which at least partly covers the dorsal side of a fingertip on the elongated body member.

* * * * *